United States Patent
McKee et al.

(10) Patent No.: US 10,155,789 B2
(45) Date of Patent: *Dec. 18, 2018

(54) SUBSTRATES AND INHIBITORS OF PROLYL OLIGOPEPTIDASE AND METHODS OF USE THEREOF

(71) Applicant: The Board of Regents of the University of Oklahoma, Norman, OK (US)

(72) Inventors: Patrick A. McKee, Oklahoma City, OK (US); Kenneth W. Jackson, Edmond, OK (US); Victoria J. Christiansen, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/602,709

(22) Filed: May 23, 2017

(65) Prior Publication Data

US 2017/0260231 A1    Sep. 14, 2017

Related U.S. Application Data

(63) Continuation of application No. 14/398,886, filed as application No. PCT/US2013/039543 on May 3, 2013, now Pat. No. 9,688,722.

(60) Provisional application No. 61/793,183, filed on Mar. 15, 2013, provisional application No. 61/643,001, filed on May 4, 2012.

(51) Int. Cl.

| | |
|---|---|
| *C07K 5/11* | (2006.01) |
| *A61K 38/18* | (2006.01) |
| *A61K 38/21* | (2006.01) |
| *A61K 38/28* | (2006.01) |
| *A61K 38/30* | (2006.01) |
| *C07K 5/09* | (2006.01) |
| *C07K 7/06* | (2006.01) |
| *C07K 5/02* | (2006.01) |
| *C07K 5/093* | (2006.01) |
| *C07K 5/097* | (2006.01) |
| *C07K 5/078* | (2006.01) |
| *C07K 5/072* | (2006.01) |
| *C07K 5/062* | (2006.01) |
| *C07K 5/068* | (2006.01) |
| *A61K 38/00* | (2006.01) |

(52) U.S. Cl.
CPC ........ *C07K 5/1019* (2013.01); *A61K 38/1825* (2013.01); *A61K 38/1858* (2013.01); *A61K 38/21* (2013.01); *A61K 38/28* (2013.01); *A61K 38/30* (2013.01); *C07K 5/0202* (2013.01); *C07K 5/06043* (2013.01); *C07K 5/06069* (2013.01); *C07K 5/06086* (2013.01); *C07K 5/06095* (2013.01); *C07K 5/06104* (2013.01); *C07K 5/06113* (2013.01); *C07K 5/06147* (2013.01); *C07K 5/0815* (2013.01); *C07K 5/0817* (2013.01); *C07K 5/0819* (2013.01); *C07K 5/0821* (2013.01); *C07K 7/06* (2013.01); *A61K 38/00* (2013.01)

(58) Field of Classification Search
CPC ............ A61K 2300/00; A61K 38/1825; A61K 38/1858; A61K 38/21; A61K 38/28; A61K 38/30; A61K 38/00; C07K 5/0202; C07K 5/06043; C07K 5/06069; C07K 5/06086; C07K 5/06095; C07K 5/06104; C07K 5/06113; C07K 5/06147; C07K 5/0815; C07K 5/0817; C07K 5/0819; C07K 5/0821; C07K 5/1019; C07K 7/06
See application file for complete search history.

(56) References Cited

U.S. PATENT DOCUMENTS

| | | | |
|---|---|---|---|
| 4,161,522 A | 7/1979 | Hamburger | |
| 4,935,493 A | 6/1990 | Bachovchin | |
| 7,208,579 B2 | 4/2007 | Watson | |
| 7,399,869 B2 | 7/2008 | Cohen | |
| 8,933,201 B2 * | 1/2015 | McKee | ............ C07K 14/8121 530/300 |
| 9,688,722 B2 * | 6/2017 | McKee | ............ A61K 38/1825 |
| 2002/0061839 A1 | 5/2002 | Scharpe et al. | |

(Continued)

FOREIGN PATENT DOCUMENTS

| | | |
|---|---|---|
| WO | 199411502 A2 | 5/1994 |
| WO | 2006100096 A2 | 9/2006 |

(Continued)

OTHER PUBLICATIONS

Christiansen, et al.; "Targeting Inhibition of Fibroblast Activation Protein-α and Prolyl Oligopeptidase Activities on Cells Common to Metastatic Tumor Microenvironments," Neoplasia, (2013); vol. 15, No. 4, pp. 348-358.

(Continued)

*Primary Examiner* — Marcela M Cordero Garcia
(74) *Attorney, Agent, or Firm* — Dunlap Codding, P.C.

(57) ABSTRACT

Inhibitors of fibroblast activation protein alpha (FAP) and Prolyl Oligopeptidase (POP) are disclosed, along with their use in various therapies related to conditions, diseases, and disorders involving abnormal cell proliferation such as malignancies and angiogenesis, and in neural disorders such as Alzheimer's disease. Stalk portions of the inhibitor molecules, and substrates of FAP and POP, are also disclosed and may be used, for example, in screening methods for identifying such inhibitors.

20 Claims, 11 Drawing Sheets
(7 of 11 Drawing Sheet(s) Filed in Color)
Specification includes a Sequence Listing.

(56) References Cited

U.S. PATENT DOCUMENTS

2008/0057491 A1 3/2008 McKee et al.
2011/0144037 A1* 6/2011 McKee ............. C07K 14/8121
514/21.6

FOREIGN PATENT DOCUMENTS

WO 2006125227 A2 11/2006
WO 2009040083 A2 4/2009
WO 2011014025 A2 2/2011

OTHER PUBLICATIONS

Lee, et al.; "Enhancement of Fibrinolysis by Inhibiting Enzymatic Cleavage of Precursor α2-antiplasmin: reply to a rebuttal"; J. Thromb. Haemost.; (2011); vol. 9, pp. 1268-1269.
International Search Report, dated Sep. 25, 2013, in PCT/US2013/039543, filed May 3, 2013.
Written Opinion of the International Search Report, dated Sep. 25, 2013, in PCT/US2013/039543, filed May 3, 2013.
EP13784728.1; Extended European Search Report, dated Jan. 27, 2016, 23 pages.
U.S. Appl. No. 14/398,886, McKee, et al.; Office Action dated Mar. 22, 2106.
Common Bond Energies (D) and lengths (r), accessed online on Mar. 17, 2016 at http://www.wiredchemist.com/chemistry/data/bond_energies_lengths.html, 9 pages.
Lee, et al.; "Enhancement of Fibrinolysis by Inhibiting Enzymatic Cleavage of Precursor α2-antiplasmin," J. Thromb. Haemost.; (2011); vol. 9, pp. 987-996.
U.S. Appl. No. 14/398,886, McKee, et al.; Examiner-Initiated Interview and Office Action dated Aug. 30, 2016.
U.S. Appl. No. 14/398,886, McKee, et al.; Final Office Action dated Dec. 12, 2016.
Patsialas, et al.; "Peptide Analogues of 1811-1818 Loop of the A3 Subunit of the Light Chain A3—C1—C2 of FVIII of Blood Coagulation: Biological Evaluation," Amino Acids (2010), vol. 39, pp. 481-488.
Kisselev et al.; "Monitoring Activity and Inhibition of 26S Proteasomes with Fluorogenic Peptide Substrates. Proteasome," Methods of Enzymology (2005), vol. 398, pp. 364-378.
U.S. Appl. No. 14/398,886, McKee, et al.; Notice of Allowance, dated Jan. 19, 2017.

* cited by examiner

1   MKTWKIVPG VATSAVLALL VMCIVLRPSR VHNSEENTMR ALTLKDILNG TFSIKTFFPN WISGQEYLRQ SADNNIVLYN IETGQSYTIL SNRTMKSVNA

101 SNYGLSPDRQ FVYLESDYSK LWRYSYTATY YIYDLSNGEF VRGNELPRPI QYLCWSPVGS KLAVYYQNNI YLKQRPGDPP FQITFNGREN KIPNGIPDWV

201 YEEEMLATKY ALWNSPNGKF LAYAEFNDTD IPVTAYSYYG DEQYPRTINI PYPRAGAKNP VVRIFTIDTT YPAYVGPQEV PVPANIASSD YYFSWLTWVT

301 DERVCLQWLK RVQNVSVLSI CDPREDWQTW DCPKTQEHIE ESRTGWAGGF FVSTPVPSYD AISYYKIFSD KDGIKHIHYI KDTVENAIQI TSGKWEAINI

401 FRVTQDSLFY SSMEFEEYPG RRNIYRISIG SYPPSRKCVT CHLRKERCQY YTASFSDYAK YYACVCYGPG IPISTLNDGR TDQEIKILEB NKRLENALKN

501 IQLPKEEIKK LEVDEITLWY KMILPPQPDR SKKYPLLIQV YGGPCSQSVR SVFAVMWISY LASKEGNVIA LVDGRGTAPQ GDKLLYAVYR RLGVYEVEDQ

601 ITAVRKFIEM GFIOERKTAI WGMSYGGYVS SLALASGTGL FKCGIAVAPV SSNEYYASVY TERFNGLPTK DQNLEHYKNS TVMARAEYFR NVDYILLIHGT

701 ADDNVHFQNS AQTARAKVNA QVDFQAMWYS DQMHGLSGLS TMHLYTHMTH FLRQCFSLSD

Figure 2

SEQUENCE LISTING

```
<160> NUMBER OF SEQ ID NOS: 1

<210> SEQ ID NO 1
<211> LENGTH: 760
<212> TYPE: PRT
<213> ORGANISM: Homo sapiens

<400> SEQUENCE: 1

Met Lys Thr Trp Val Lys Ile Val Phe Gly Val Ala Thr Ser Ala Val
1               5                   10                  15

Leu Ala Leu Leu Val Met Cys Ile Val Leu Arg Pro Ser Arg Val His
                20                  25                  30

Asn Ser Glu Glu Asn Thr Met Arg Ala Leu Thr Leu Lys Asp Ile Leu
        35                  40                  45
```

-continued

```
Asn Gly Thr Phe Ser Tyr Lys Thr Phe Pro Asn Trp Ile Ser Gly
 50                  55                  60

Gln Glu Tyr Leu His Gln Ser Ala Asp Asn Ile Val Leu Tyr Asn
 65                  70                  75                  80

Ile Glu Thr Gly Gln Ser Tyr Thr Ile Leu Ser Asn Arg Thr Met Lys
                 85                  90                  95

Ser Val Asn Ala Ser Asn Tyr Gly Leu Ser Pro Asp Arg Gln Phe Val
                100                 105                 110

Tyr Leu Glu Ser Asp Tyr Ser Lys Leu Trp Arg Tyr Ser Tyr Thr Ala
            115                 120                 125

Thr Tyr Tyr Ile Tyr Asp Leu Ser Asn Gly Glu Phe Val Arg Gly Asn
    130                 135                 140

Glu Leu Pro Arg Pro Ile Gln Tyr Leu Cys Trp Ser Pro Val Gly Ser
145                 150                 155                 160

Lys Leu Ala Tyr Val Tyr Gln Asn Asn Ile Tyr Leu Lys Gln Arg Pro
                165                 170                 175

Gly Asp Pro Pro Phe Gln Ile Thr Phe Asn Gly Arg Glu Asn Lys Ile
            180                 185                 190

Phe Asn Gly Ile Pro Asp Trp Val Tyr Glu Glu Met Leu Ala Thr
    195                 200                 205

Lys Tyr Ala Leu Trp Trp Ser Pro Asn Gly Lys Phe Leu Ala Tyr Ala
210                 215                 220

Glu Phe Asn Asp Thr Asp Ile Pro Val Ile Ala Tyr Ser Tyr Tyr Gly
225                 230                 235                 240

Asp Glu Gln Tyr Pro Arg Thr Ile Asn Ile Pro Tyr Pro Lys Ala Gly
                245                 250                 255

Ala Lys Asn Pro Val Val Arg Ile Phe Ile Ile Asp Thr Thr Tyr Pro
            260                 265                 270

Ala Tyr Val Gly Pro Gln Glu Val Pro Val Pro Ala Met Ile Ala Ser
    275                 280                 285

Ser Asp Tyr Tyr Phe Ser Trp Leu Thr Trp Val Thr Asp Glu Arg Val
290                 295                 300

Cys Leu Gln Trp Leu Lys Arg Val Gln Asn Val Ser Val Leu Ser Ile
305                 310                 315                 320

Cys Asp Phe Arg Glu Asp Trp Gln Thr Trp Asp Cys Pro Lys Thr Gln
                325                 330                 335

Glu His Ile Glu Glu Ser Arg Thr Gly Trp Ala Gly Gly Phe Phe Val
            340                 345                 350

Ser Thr Pro Val Phe Ser Tyr Asp Ala Ile Ser Tyr Tyr Lys Ile Phe
    355                 360                 365

Ser Asp Lys Asp Gly Tyr Lys His Ile His Tyr Ile Lys Asp Thr Val
370                 375                 380

Glu Asn Ala Ile Gln Ile Thr Ser Gly Lys Trp Glu Ala Ile Asn Ile
385                 390                 395                 400

Phe Arg Val Thr Gln Asp Ser Leu Phe Tyr Ser Ser Asn Glu Phe Glu
                405                 410                 415

Glu Tyr Pro Gly Arg Arg Asn Ile Tyr Arg Ile Ser Ile Gly Ser Tyr
            420                 425                 430

Pro Pro Ser Lys Lys Cys Val Thr Cys His Leu Arg Lys Glu Arg Cys
    435                 440                 445

Gln Tyr Tyr Thr Ala Ser Phe Ser Asp Tyr Ala Lys Tyr Tyr Ala Leu
450                 455                 460

Val Cys Tyr Gly Pro Gly Ile Pro Ile Ser Thr Leu His Asp Gly Arg
```

-continued

```
            465                 470                 475                 480
        Thr Asp Gln Glu Ile Lys Ile Leu Glu Glu Asn Lys Glu Leu Glu Asn
                            485                 490                 495

Ala Leu Lys Asn Ile Gln Leu Pro Lys Glu Glu Ile Lys Lys Leu Glu
                            500                 505                 510

Val Asp Glu Ile Thr Leu Trp Tyr Lys Met Ile Leu Pro Pro Gln Phe
                            515                 520                 525

Asp Arg Ser Lys Lys Tyr Pro Leu Leu Ile Gln Val Tyr Gly Gly Pro
                            530                 535                 540

Cys Ser Gln Ser Val Arg Ser Val Phe Ala Val Asn Trp Ile Ser Tyr
        545                 550                 555                 560

Leu Ala Ser Lys Glu Gly Met Val Ile Ala Leu Val Asp Gly Arg Gly
                            565                 570                 575

Thr Ala Phe Gln Gly Asp Lys Leu Leu Tyr Ala Val Tyr Arg Lys Leu
                            580                 585                 590

Gly Val Tyr Glu Val Glu Asp Gln Ile Thr Ala Val Arg Lys Phe Ile
                            595                 600                 605

Glu Met Gly Phe Ile Asp Glu Lys Arg Ile Ala Ile Trp Gly Trp Ser
                            610                 615                 620

Tyr Gly Gly Tyr Val Ser Ser Leu Ala Leu Ala Ser Gly Thr Gly Leu
        625                 630                 635                 640

Phe Lys Cys Gly Ile Ala Val Ala Pro Val Ser Ser Trp Glu Tyr Tyr
                            645                 650                 655

Ala Ser Val Tyr Thr Glu Arg Phe Met Gly Leu Pro Thr Lys Asp Asp
                            660                 665                 670

Asn Leu Glu His Tyr Lys Asn Ser Thr Val Met Ala Arg Ala Glu Tyr
                            675                 680                 685

Phe Arg Asn Val Asp Tyr Leu Leu Ile His Gly Thr Ala Asp Asp Asn
                            690                 695                 700

Val His Phe Gln Asn Ser Ala Gln Ile Ala Lys Ala Leu Val Asn Ala
        705                 710                 715                 720

Gln Val Asp Phe Gln Ala Met Trp Tyr Ser Asp Gln Asn His Gly Leu
                            725                 730                 735

Ser Gly Leu Ser Thr Asn His Leu Tyr Thr His Met Thr His Phe Leu
                            740                 745                 750

Lys Gln Cys Phe Ser Leu Ser Asp
                            755                 760
```

SUBSTRATES AND INHIBITORS OF PROLYL OLIGOPEPTIDASE AND METHODS OF USE THEREOF

CROSS-REFERENCE TO RELATED APPLICATIONS/INCORPORATION BY REFERENCE STATEMENT

The present application is a continuation of U.S. Ser. No. 14/398,886, filed Nov. 4, 2014; which is a national stage application under 35 USC § 371 of international application PCT/US2013/39543, filed May 3, 2013; which claims the benefit under 35 USC § 119(e) of U.S. Provisional Application Ser. No. 61/643,001, filed May 4, 2012, and U.S. Provisional Application Ser. No. 61/793,183, filed Mar. 15, 2013. The entire contents of each of the above-referenced applications are hereby expressly incorporated herein by reference.

STATEMENT REGARDING FEDERALLY SPONSORED RESEARCH OR DEVELOPMENT

This invention was made with government support under Contract Number W81XWH-081-0588 awarded by the Department of Defense (DOD) and Contract Number HL072995 awarded by the National Institutes of Health (NIH). The government has certain rights in the invention.

BACKGROUND $\alpha_2$-Antiplasmin ($\alpha_2$AP) is a glycoprotein in blood plasma that rapidly and specifically inhibits the enzyme, plasmin, which digests blood clots, whether presenting early as intravascular platelet-fibrin deposits or as partially or completely occlusive thrombi. Similarly, plasmin and $\alpha_2$AP activities are important to the development and survival of fibrin as occurs in inflammation, wound healing and virtually all forms of cancer and its metastases. Human $\alpha_2$-antiplasmin ($\alpha_2$AP), also known as $\alpha_2$-plasmin inhibitor, is the main inhibitor of plasmin. Plasmin plays a critical role in fibrin proteolysis and tissue remodeling. The inventors discovered antiplasmin-cleaving enzyme (APCE) in human plasma and showed that it is a soluble isoform or derivative of fibroblast activation protein-alpha (FAP). Like APCE, FAP is also a prolyl-specific enzyme that exhibits both endopeptidase and dipeptidyl peptidase activities.

FAP significantly over-expresses in >90% of epithelial-derived cancers [1-3]. FAP is produced transiently by activated stromal fibroblasts during embryogenesis [4] and wound healing [3], but other than an occasional normal fibroblast or pancreatic islet $\alpha$-cell, it is not expressed by normal adult tissues or benign tumors [2, 3, 5]. FAP is prominent on the membranes of proliferating fibroblasts in diseases where fibrous tissue growth is a conspicuous feature, such as primary pulmonary fibrosis [6]; chronic hepatitis [7]; certain bone-associated malignancies [8, 9]; and the arthritides [10]. Selected parenchymatous cancer cells may also occasionally express FAP [11].

While a biologic substrate for the proteinase activity of FAP has not been definitively established, results indicate that FAP helps digest extracellular matrix (ECM) components as tissue is remodeled to accommodate cancer expansion [2, 16, 17]. Paradoxically, activated fibroblasts not only digest ECM, but also synthesize ECM components of the stromal scaffolding that support cell division and motility during neoplastic growth [18]. FAP has been considered a potential target in the diagnosis and therapy of cancer, with inhibition of FAP proteinase activity posed as possibly therapeutically useful [19, 20]. Santos et al. [21] have shown that genetic deletion or pharmacologic inhibition of FAP by glutamyl-proline boronic acid (Glu-boroPro) decreased stromal growth in mouse models of lung and colon cancer. However, Glu-boroPro has an exceptionally short plasma half-life before cyclizing and losing inhibitory activity [22]. Moreover, it also inhibits dipeptidyl peptidase IV (DPPIV), which is important in plasma glucose regulation and immune function [23]. Hence, despite inhibiting FAP and suppressing tumor growth, Glu-boroPro is not likely to be therapeutically useful in cancer [24].

The measurement of cellular FAP activity and inhibition is confounded by another prolyl endopeptidase: namely, Prolyl Oligopeptidase (POP) which is elevated in many cancers [25]. POP is a prolyl-specific serine proteinases, which cleaves peptides of less than about 30 amino acids in length. The enzyme is present in most tissues, but is noted to be more abundant in selected organs, e.g., brain and kidney. Recently POP has been indicated as making secondary cleavages of thymosin-$\beta$4 to yield the derivative peptide, acetyl-serine-asparagine-lysine-proline, which appears to be a potent stimulator of angiogenesis [26]. Both FAP and POP activities are commonly measured using non-specific substrates such as Z-Gly-Pro-AMC or succinyl-Gly-Pro-AMC, neither of which distinguishes between the two activities [27]. Consequently, total prolyl-specific endopeptidase activity, which is often attributed to FAP alone, may also include POP activity. This complicates interpretations about the effects of inhibiting either enzyme on cancer growth. Pre-clinical studies have suggested other promising applications of POP inhibition for managing memory, learning disorders and depression, but development of relatively benign, highly effective POP inhibitors for in vivo testing have been elusive. The results, newly described herein, indicate that POP is expressed in significant amounts by a variety of cancer cells grown in culture.

Certain compounds which specifically inhibit either one or both of FAP and POP and therefore can be used to treat various conditions which involve these proteins are desirable. Thus, the presently disclosed and claimed inventive concept(s) is directed to, but not limited to, substrates and inhibitors of FAP and/or POP, and to methods of using FAP and/or POP inhibitors for treating conditions such as but not limited to, cancers, neural disorders, and angiogenesis, and to screening methods for identifying such inhibitors, that overcome the disadvantages and defects of the prior art.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 2 shows the amino acid sequence of FAP (SEQ ID NO:1) and corresponding tryptic FAP peptides isolated from four human cell types. Protein was purified by immunoprecipitation and SDS-polyacrylamide gel electrophoresis followed by sequence determination by LC/MS/MS. Correspondence to FAP protein is indicated: Human mesenchymal stem cells (-) 51% (coverage FAP sequence); WI-38 fibroblasts (■■■), 42%; MDA-MB436 cancer cells (☉☉☉☉), 41%; and HMVEC-d endothelial cells deprived of hydrocortisone (✖✖✖✖), 6.4%. In each case, the FAP-containing region of the gel was located by reference to a 100 kDa protein standard band in an adjacent lane.

DETAILED DESCRIPTION

Figure 1:
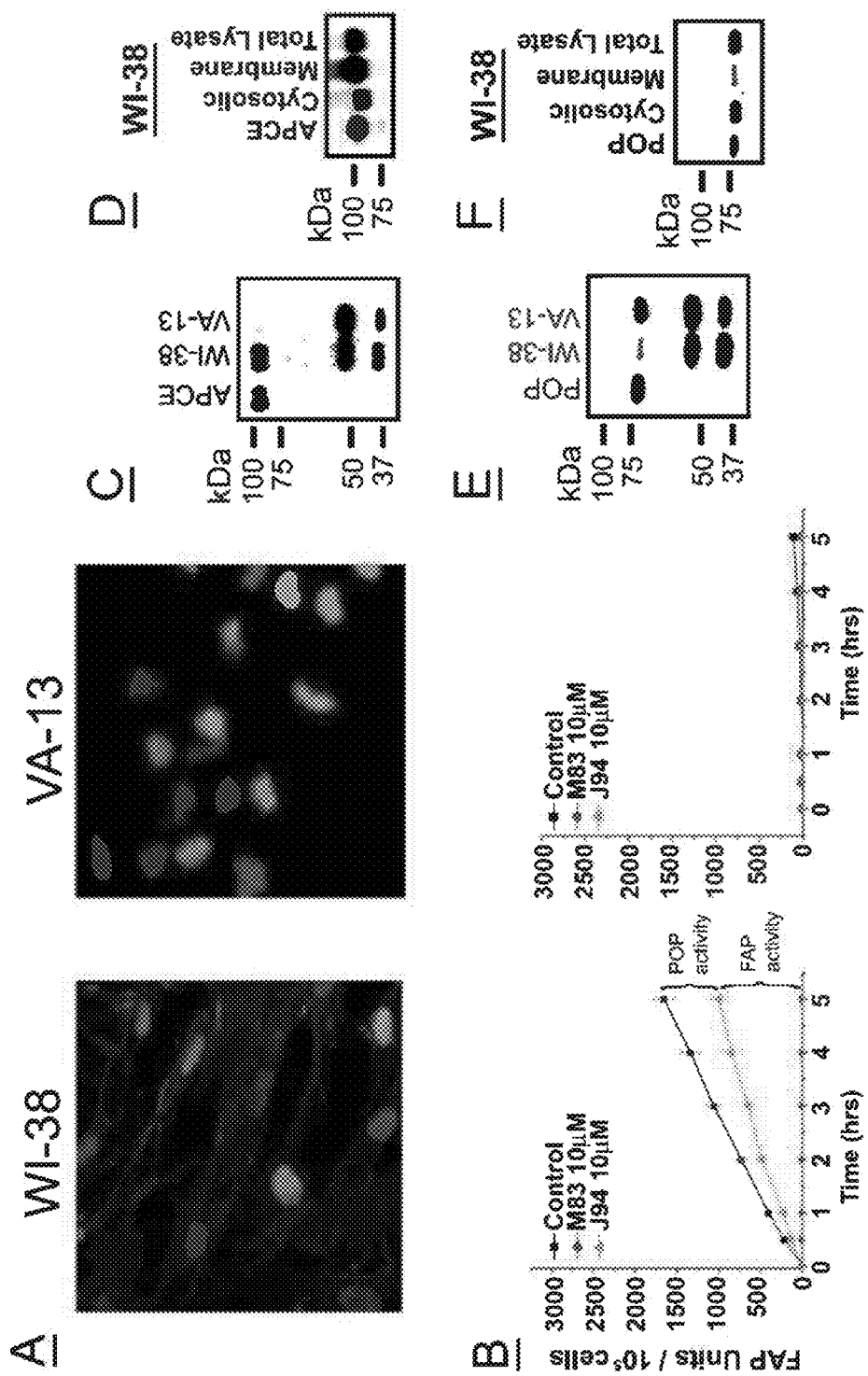
FIG. 1 is a characterization of FAP and POP in fibroblasts. Panel A. Confocal images of permeabilized WI-38 and VA-13 fibroblasts grown on plastic slides and labeled with mouse anti-FAP mAb F19 followed by anti-mouse-AlexaFluor 568 (red) and the DNA stain DAPI (green). Panel B. FAP and POP activities of fibroblasts grown on plastic wells as measured by cleavage of a fluorescent substrate designated as "C95" (acetyl-Arg-AEEA-Gly-Pro-AMC), and using a POP specific inhibitor compound designated as "J94" (acetyl-Lys-Leu-Arg-(L)boroPro) to separate the two activities. One FAP unit=$\Delta$ fluorescence/min on cleavage of C95 by one ng APCE. Panel C. Immunostains of cell lysates from fibroblast cultures using mouse anti-FAP mAb 6D2. One ng APCE served as a positive control while intracellular contents of α-tubulin (50 kDa) and actin (43 kDa) were used for standardizing the amount of cell lysate protein applied in each lane. Panel D. Immunostains of cell lysates and membrane and cytosol fractions from WI-38 fibroblast cultures using mouse anti-FAP mAb 6D2. One ng APCE served as a positive control. Panel E. Immunostains of cell lysates from fibroblast cultures using goat anti-POP. One ng of POP served as a positive control, while α-tubulin (50 kDa) and actin (43 kDa) were used for standardizing loads. Panel F. Immunostains of cell lysates and membrane and cytosol fractions from WI38 fibroblast cultures using goat anti-POP. One ng of POP served as a positive control.

Before explaining the at least one non-limiting embodiment of the inventive concept(s) disclosed herein in detail, it is to be understood that the presently disclosed and claimed inventive concept(s) is not limited in its application to the details of examples, experiments, exemplary data, and/or methods or steps as set forth in the following description, or illustrated in the drawings. The presently disclosed and claimed inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

In the following detailed description of embodiments of the presently disclosed and claimed inventive concept(s), numerous specific details are set forth in order to provide a more thorough understanding of the inventive concept(s). However, it will be apparent to one of ordinary skill in the art that the inventive concept(s) within the disclosure may be practiced without these specific details. In other instances, well-known features have not been described in detail to avoid unnecessarily complicating the present disclosure.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference. In particular, the present application contains subject matter which is related to U.S. Ser. No. 12/969,161, filed Dec. 15, 2010; 61/286,558, filed Dec. 15, 2009; Ser. No. 11/811,002, filed Jun. 6, 2007; 60/811,568, filed Jun. 7, 2006; and 60/836,365, filed Aug. 8, 2006. The entire contents of each of these applications are hereby expressly incorporated herein by reference in its entirety. Also, U.S. Ser. Nos. 10/774,242; 11/810,997; 11/986,058; and 60/445,774 are hereby expressly incorporated herein by reference in their entireties.

All of the compositions and/or methods disclosed and claimed herein can be made and executed without undue experimentation in light of the present disclosure. While the compositions and methods of the inventive concept(s) have been described in terms of particular embodiments, it will be apparent to those of skill in the art that variations may be applied to the compositions and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope and concept of the inventive concept(s) as defined by the appended claims.

In order that the presently disclosed and claimed inventive concept(s) may be more readily understood, certain term are first defined. Additional definitions are set forth throughout the detailed description. Unless defined otherwise, all technical and scientific terms used herein have the same meanings as commonly understood by one skilled in the art to which the presently disclosed and claimed inventive concept(s) pertains (e.g., amino acids may be referred to by their commonly used abbreviations).

APCE is Antiplasmin-Cleaving Enzyme. FAP is Fibroblast Activation Protein-alpha. POP is Prolyl Oligopeptidase. DPPIV is Dipeptidyl peptidase IV. $\alpha_2$AP is $\alpha_2$-Antiplasmin. AEEA is 2-(2-(2-aminoethoxy) ethoxy) acetic acid, also referred to herein as 8-amino-3,6-dioxaoctanoic acid. AMC is 7-amido-4-methylcoumarin. L-boroPro is L-boronyl proline. M83 is acetyl-Arg-AEEA-(D)Ala-(L)boroPro. C95 is acetyl-Arg-AEEA-Gly-Pro-AMC. J94 is acetyl-Lys-Leu-Arg-(L)boroPro. L96 is acetyl-Lys-Leu-Arg-Pro-AMC. Abz is aminobenzoyl. Ac is acetyl. Bz is benzoyl. Z is benzyloxycarbonyl. Boc is t-Butyloxycarbonyl. Fa is Furylacryloyl. MeOSuc is methoxysuccinyl. Pyr is pyroglutamate. AFC is 7-amino-trifluoromethylcoumarin. OEt is ethyl ester. OMe is methyl ester (OMe). 2NA is 2-Naphthylamide (2NA). p-NA is p-Nitroanilide. ONp is p-Nitrophenyl ester. SBzl is Thiobenzyl ester. "Tic" refers to 1,2,3,4 tetrahydro isoquinoline-3-carboxylic acid. HCC, HCC1419 breast cancer cells; HMVEC-d, human microvascular endothelial cells from dermis; MCF12A, normal breast cells; MDA, MDA-MB436 breast cancer cells; MSC, mesenchymal stem cells; VA-13, WI-38 VA-13 2RA SV-40 viral transformed fibroblast cells; WI-38, fibroblast cells.

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by ±20% or ±10%, or ±5%, or ±1%, or ±0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, "pharmaceutically acceptable" refers to those properties and/or substances, which are acceptable to the patient from a pharmacological/toxicological point of view including bioavailability and patient acceptance or to the manufacturing chemist from a physical-chemical point of view regarding composition, formulation, stability and isolatability. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically-acceptable carrier" as used herein means a pharmaceutically-acceptable material, composition, or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

As used herein, a "therapeutically effective amount" the inhibitor or chemotherapeutic agent of the presently disclosed and claimed inventive concept(s) refers to an amount of a compound that is effective, upon single- or multiple-dose administration to the subject, e.g., a patient, at enhancing the inhibition of the growth or proliferation, or inducing the killing, of hyperproliferative cells, e.g., cancer cells by a chemotherapeutic compound or by radiation treatment. The term, for example, "therapeutically effective amount" refers to an amount of an inhibitory compound of the presently disclosed and claimed inventive concept(s) that is administered, e.g., coadministered, (i.e., sequentially or concomitantly) with one or more cytotoxic agents such that the inhibitory compound and the cytotoxic agent, are effective, upon single- or multiple-dose administration to the subject, e.g., a patient, at inhibiting the growth or proliferation, or inducing the killing, of hyperproliferative or angiogenic cells. Such growth inhibition or killing can be reflected as a prolongation of the survival of the subject, e.g., a patient beyond that expected in the absence of such treatment, or any improvement in the prognosis of the subject relative to the absence of such treatment. As used herein, the term "carcinomas" refers to lesions that are cancerous. As used herein, the term "neoplasm" refers to both precancerous and cancerous lesions. As used herein, the terms "inhibit" or "inhibiting," mean decreasing FAP, POP, or APCE activity, or tumor cell growth rate or other targeted activity from the rate that would occur without treatment of the inhibitor compound and/or causing tumor mass to decrease. Inhibiting also includes causing a complete regression of the tumor. Thus the compounds of the presently disclosed and claimed inventive concept(s) can be either cytostatic or cytotoxic to the tumor cells, when used alone or in combination with other therapies.

As used herein, the terms "cytotoxic agent", "chemotherapeutic agent", "anticancer agent", and "antitumor agent" are used interchangeably herein and refer to agents that have the property of inhibiting the growth or proliferation (e.g., a cytostatic agent), or inducing the killing, of hyperproliferative cells. As used herein, "chemosensitization" and "chemosensitizing effect" are used interchangeably and refer to the enhancement of radiation or chemotherapy efficacy by the compound. "Chemosensitizer" refers to the agent that enhances the efficacy of another agent, such as the cytotoxic agent or radiation.

The term "a drug or compound for overcoming a resistance to an anticancer drug or an anticancer-drug-resistance overcoming drug" or "a pharmaceutical composition for overcoming a resistance to an anticancer drug or an anticancer-drug-resistance overcoming pharmaceutical-composition" refers to a drug which has no carcinostatic activity itself but has a function of reducing a resistance of cancer cells to an anticancer drug. In other words, it means a drug having a function for increasing sensitivity to an anticancer drug of cancer cells having an acquired resistance to the anticancer drug. In this case, the increase of the sensitivity means not only to increase an effect of an anticancer drug to anticancer-drug resistant cells in a higher level than that to anticancer-drug sensitive cells but also to increase the effect of the anticancer drug to the anticancer-drug resistant cells in approximately the same level as that to the anticancer-drug sensitive cells. Further, another term equivalent to "overcoming a resistance" may include "restraining or inhibiting a resistance", "releasing resistance", "releasing tolerance" or "increasing or enhancing a sensitivity".

The term "administrating together with" in the presently disclosed and claimed inventive concept(s) means administering two kinds of drugs simultaneously, continuously or at intervals. The two kinds of drugs may be administered as a mixture or as separate drugs. When administering as separate drugs, each administering route may be or may be not the same. As defined herein, treating cancer (i.e., with an anticancer therapy) in a patient includes achieving, partially or substantially, one or more of the following: arresting the growth or spread of a cancer, reducing the extent of a cancer (e.g., reducing size of a tumor or reducing the number of affected sites). Inhibiting the growth rate of a cancer, and ameliorating or improving a clinical symptom or indicator associated with a cancer (such as tissue or serum components). The term "treatment" as used herein is also intended to encompass prophylaxis, therapy and cure.

Also, where used herein, the terms "heterocycle" or "heterocyclic" refer to ring structures, particularly 4, 5, 6, or 7-membered ring structures, and more particularly 5- to 6-membered rings, whose ring structures include one to four heteroatoms such as nitrogen, sulfur, or oxygen. Heterocyclic groups include, but are not limited to, thiophene, furan, pyran, pyrrole, imidazole, pyrazole, isothiazole, isoxazole, pyridine, pyrazine, pyrimidine, and pyridazine. The heterocyclic ring can be substituted at one or more positions with such substituents as, for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, $CF_3$, CN, or the like. Where used herein, the term "carbocycle" or "carbocyclic" refers to an aromatic or non-aromatic ring in which each atom of the ring is carbon and may particularly comprise 4, 5, 6 or 7 carbons per ring, such as 5 or 6 carbons per ring.

The term "stalk" or "stalk portion" as used herein will be understood to refer to portions of the compounds disclosed herein, such as but not limited to, Formulas I-IV, that are missing the Cyc groups thereof.

Additionally, the proline analogs and derivatives or other amino acids of the peptidomimetic compounds of the presently disclosed and claimed inventive concept(s) may exist in particular geometric or stereoisomeric forms. The presently disclosed and claimed inventive concept(s) includes all such compounds, including cis- and trans-isomers, R- and S-enantiomers, diastereomers, (D)-isomers, (L)-isomers, the racemic mixtures thereof, and other mixtures thereof, as falling within the scope of the presently disclosed and claimed inventive concept(s). Additional asymmetric carbon atoms may be present in a substituent such as, but not limited to, an alkyl group. All such isomers, as well as mixtures thereof, are intended to be included in the presently disclosed and claimed inventive concept(s).

Turning now to the presently disclosed and claimed inventive concept(s), inhibitors of prolyl oligopeptidase (POP) and fibroblast activation protein-alpha (FAP) are provided, as are substrates of APCE, FAP, or POP. The presently disclosed and claimed inventive concept(s) also includes, but is not limited to, methods of using such inhibitors to treat, inhibit, and/or ameliorate conditions and/or diseases involving FAP and/or POP, such as, but not limited to, epithelial-derived cancers, angiogenesis (such as angiogenesis which occurs during formation of tumors or in diabetes), Alzheimer's disease, atherosclerosis, and thrombus disorders and conditions involving abnormal cell proliferation, as well as other cancers and disorders identified herein. Substrates of APCE, FAP, and POP may also be used, for example, in screening methods for identifying inhibitors of FAP and POP.

Thus, the presently disclosed and claimed inventive concept(s) is directed to (but not limited to) methods and compounds for treating conditions characterized by abnormal cell proliferation, angiogenesis, and/or neural disorders, including, but not limited to, cancer and metastasis, and Alzheimer's disease, by using the inhibitors of the present disclosure to inhibit the enzymatic activity of FAP and POP in vivo. In one embodiment, the presently disclosed and claimed inventive concept(s) provides a method for treating a subject having a condition characterized by abnormal mammalian cell proliferation and/or angiogenesis. In the method, an agent is administered to a subject in need of such treatment in an amount effective to inhibit cell proliferation and/or angiogenesis. The agent is, or comprises, a compound having at least one of Formula I and Formula II as described herein.

The inventors discovered the circulating antiplasmin-cleaving enzyme (APCE) and showed it to be either a derivative of fibroblast activation protein (FAP) or a slight variant thereof due to gene splicing differences [1,2]. Except for the absence of an about 26-residue amino terminal peptide constituting the transmembrane and intracytosolic domains, APCE is otherwise identical to FAP in molecular structure and function. FAP is over expressed by stromal cells in >90% of epithelial-derived malignancies, but not by normal tissues or benign tumors, hence causing FAP to be viewed as having major potential as a unique diagnostic and therapeutic target in a wide array of human cancers.

Subsequent research indicated that POP, another member of the Glade of prolyl-specific serine proteinases, had proteolytic activity which overlapped that of FAP when conventionally available synthetic substrates such as Z-Gly-Pro-AMC were used for FAP activity measurments. Although the principal inhibitor of FAP manifested both high selectivity and sensitivity, it also inhibited POP, and this has been a consistent problem in trying to separate and quantitate the activity of each of these enzymes. Very effective and specific inhibitors of POP have thus been designed and synthesized, as described herein. It has also been discovered that the POP inhibitor very rapidly and effectively blocked capillary-like tube formation by human dermal endothelial cells. Thus, in one aspect of the presently disclosed and claimed inventive concept(s), the POP inhibitors described herein can be used as anti-angiogenic agents and as effective, high affinity, sensitive inhibitors of POP in certain mammalian diseases, particularly where therapeutic effectiveness has been limited due to problems of inhibitor solubility and/or inhibition of other enzymes where such inhibition was undesireable and carried potential for adverse pharmacologic outcomes.

Figure 10A:
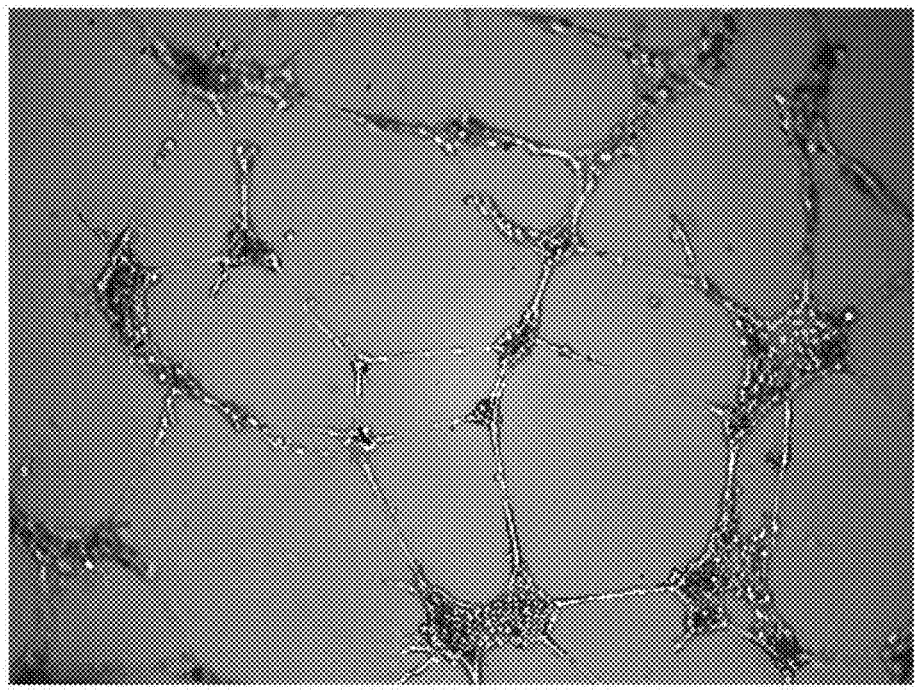
FIGS. 10A and B are micrographs which demonstrate that application of 50 μm of compound J94 inhibited formation of capillary-like tubes in Matrigel™.
Figure 10B:
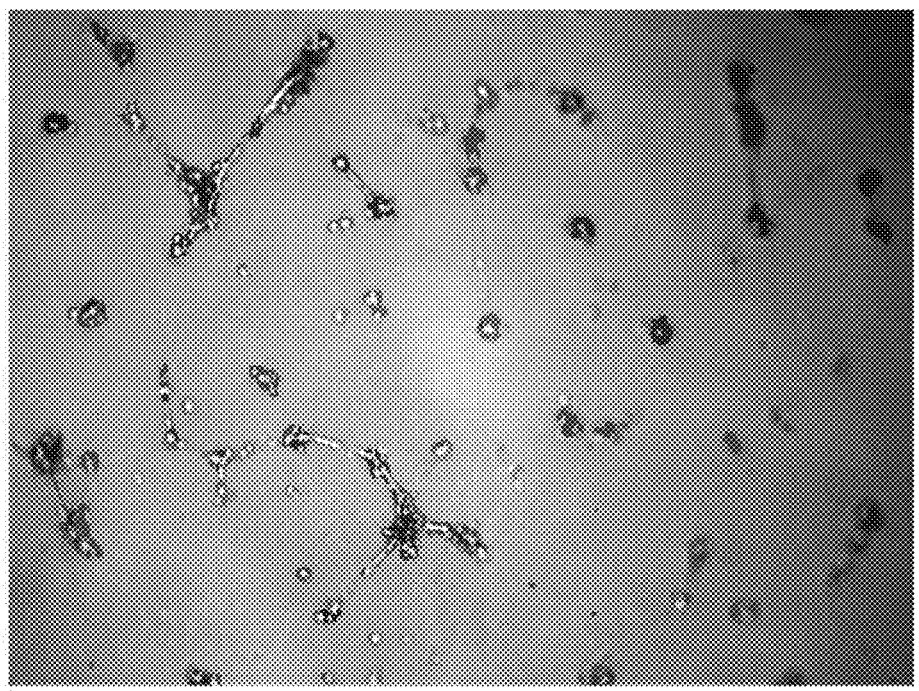

Further, it has been discovered that POP is extensively expressed by activated fibroblasts that characteristically participate in the development of scaffolding over which cancer cells grow as the tumor expands. One embodiment of the presently disclosed and claimed inventive concept(s) is a pseudo-peptide, acetyl-Lys(K)-Leu(L)-Arg(R), which forms a stalk of a very specific, sensitive fluorescent substrate for the POP enzyme, namely acetyl-KLRP-AMC (designated herein as L96), which has been shown to be cleaved by POP with a $K_m$ of 30±3 μM and $k_{cat}$=2.4±0.1 $s^{-1}$. Neither DPPIV nor APCE/FAP cleaved this substrate. The substrate can be used to assess POP activity from a variety of sources including, but not limited to, human plasma, tissue, and culture media. In another embodiment, the acetyl-Lys(K)-Leu(L)-Arg(R) peptide is used as a stalk of another pseudo-peptide, acetyl-KLR-(L)-boroPro, and alternate versions thereof as represented by Formula II, which proved to be a very highly sensitive, selective POP inhibitor ($K_1 \ll 100$ nM), and useful for separating the activities of POP and ACE/FAP. Using standard tissue culture methods for growing blood vessel capillaries in vitro, it is also demonstrated that POP is also expressed by human endothelial cells as they became confluent and progress to capillary-like tube formation. It has also been demonstrated that application of 50 µM POP inhibitor (J94) abrogated the genesis of capillary-like tubes (FIG. 10). Hence one of the potent effects of the inhibitor described here is that it disrupts angiogenesis by instantaneously inhibiting POP activity. Given the obligatory need of microcirculation to enable tissue growth, the inhibition of POP by the inhibitor indicates its ability to abrogate undesirable tissue expansion, i.e., malignant growth, by blocking the development of a requisite microcirculation.

To date, many of the POP inhibitors designed and invented by others have not been used clinically for inhibiting angiogenesis. An important advantage of the novel inhibitors described herein is the high degree of solubility manifested under aqueous conditions, which is a requirement for use in tissues where water is the overwhelming physiologic solvent, and counters the significant negative of previous inhibitors that are incompletely soluble under in vivo conditions.

In one embodiment, the presently disclosed and claimed inventive concept(s) is directed to the use of these POP inhibitors for the treatment of human disorders and diseases, such as various mood, memory, and behavioral disorders, as well as learning disorders, and also for blocking angiogenesis by specifically and selectively inhibiting POP. In certain embodiments, the presently disclosed and claimed inventive concept(s) is particularly directed to those human diseases where formation of new blood vessels is essential for disease progression, as in malignancies (specifically epithelial-derived malignancies), in retinal blood vessel proliferation, in sickle cell disease, and in diabetes mellitus.

In one embodiment, inhibition of FAP or POP is defined herein as at least 50% inhibition of activity of FAP or POP, respectively, for example, at an inhibitor concentration of 20 µM. Examples of the inhibitors are described below, and in one embodiment comprise a boroPro linked to the stalk unit. Groups which may substitute for boroPro (boronyl proline), include, but are not limited to, other boronic acid derivatives, carbocyclic groups, heterocyclic groups, carbonitriles, carboxynitriles, or nitrilic-containing compounds, where the Arg (or other positively-charged N-terminal amino acid) may or may not be blocked with a protecting group such as, but not limited to, succinyl, acetyl, benzoyl, benzyloxycarbonyl, or other protecting group commonly used for blocking peptides from attack by proteases.

The FAP inhibitors of the presently disclosed and claimed inventive concept(s) can be used in treatment of various cancers and/or other FAP-related conditions or other conditions involving abnormal cell proliferation, as described in further detail below. With respect to FAP, inhibition of this enzyme will limit or obviate the ability of epithelial-derived cancers to invade the surrounding extracellular matrix, thereby limiting the cancer's spread and allowing more effective use of chemotherapy or radiation therapy. Without wishing to be bound by theory, the FAP inhibitors described herein are effective, highly efficient inhibitors which prevent, inhibit, and/or reduce the expansion of extracellular space by digestion of FAP's substrate proteins, e.g., type I collagen within the extracellular matrix (ECM). This will then abrogate subsequent movement of activated fibroblasts for remodeling ECM space with new stromal scaffolding to which malignant cells adhere for migration and mitosis. As a consequence, the neoplasm will then atrophy and undergo necrosis, or be arrested to an extent that radiation and/or chemotherapy measures, desirably at lower than standard doses, will eradicate the malignancy. Previously a number of studies of metastatic cancer indicated that Val-boroPro, a dipeptide containing a boronic acid derivative of proline (for example, as described in U.S. Pat. No. 7,399,869), inhibits FAP, and as a consequence, cancer growth. Unfortunately, however, Val-boroPro also non-selectively inhibits most prolylpeptidases such as dipeptidyl peptidases (such as DPPIV) and up-regulates cytokine and chemokine-5 activities. Several other prolyl boronic acid derivatives have been developed and reported as putative selective inhibitors for FAP, but their instability in aqueous environments at physiologic pH and their non-specific reactivities with other enzymes due to the electrophilic property of boronic acid has complicated progress in their use.

POP activity has been shown to be elevated in subjects with neurological disorders such as, but not limited to, bipolar disorder, autism, schizophrenia, various stress-related disorders, memory loss, and memory deficits (such as those characteristic of Alzheimer's disease). Without wishing to be bound by theory, POP appears to be involved in cognitive functions via the cleavage of neuropeptides. Increased levels of POP may lead to reduced levels of key neuropeptides, which may be restored by administration of POP inhibitors. In any event, by whatever mechanism POP has its effect, inhibition of POP can be used as a treatment of these diseases, disorders, and conditions (see, for example, references 55-58 and U.S Published Patent Applications 2003/0096392, 2005/0020677, 2007/0060550, and 2008/0269313, in regard to the use of POP inhibitors in the treatment of such neural conditions; the entirety of each of these references being expressly incorporated herein by reference).

Prior to the presently disclosed and claimed inventive concept(s), there were no effective inhibitors of FAP or POP that have sufficient specificity to allow exploration of effects on the pathogenesis and/or therapy of chronic diseases such as atherosclerosis or a variety of different cancers. For example, various dipeptide boronyl-proline constructs (e.g., "val-boroPro") have been used in efforts to inhibit FAP, but as noted above, these constructs also inhibited several other prolyl peptidases, some of the latter being critical for important metabolic functions. Moreover, the design of these amino acid boroProline inhibitors did not prevent or slow their cyclization and inactivation that occurs within a few minutes in aqueous environments. The inhibitors of the presently disclosed and claimed inventive concept(s) avoid these pitfalls.

Further, the presently disclosed inhibitor compounds with high specificity for FAP and/or POP can be used in in vitro assays based on cancer cell lines to determine the role of FAP at various stages of pathogenesis of FAP-related cancers. The exact mode of how FAP operates in specific cancer etiologies is still under study, and an inhibitor molecule for selectively inhibiting FAP can be most useful.

FAP and POP Inhibitors

Certain embodiments of the presently disclosed and claimed inventive concept(s) include APCE-inhibitory, FAP-inhibitory, and/or POP-inhibitory peptidomimetics. The peptidomimetics may have up to 28 amino acids or more, as well as less than 28 amino acids. The peptidomimetics comprise proline analogs and derivatives thereof for use as a $P_1$ proline substitute, including, but not limited to, the proline analogs and derivatives shown in Table 1 or discussed or described elsewhere herein. The peptidomimetics (inhibitors) particularly may comprise 2, 3, 4, 5, 6, 7, 8, 9, 10, 11, 12, 13, 14, 15, 16, 17, 18, 19, 20, 21, 22, 23, 24, 25, 26, 27, or 28 amino acids, and the peptidomimetics may further comprise a spacer compound (which may be an amino acid) for separating certain amino acids of the compound, or compounds which may be bound or complexed thereto, for extending the serum life of the peptide. Such spacers are discussed further below.

Inhibitors of the presently disclosed and claimed inventive concept(s) may possess a charged residue (positively-charged in the case of FAP inhibitors) at a distance corresponding to the length of two to seven residues upstream of the proline analog (0.3 nm-2.4 nm) and can be used as a rapid, tightly binding and effective inhibitor of APCE, FAP, and/or POP. Such inhibitors can be useful for the treatment of disorders relating to FAP and POP, for example, as described elsewhere herein.

In certain embodiments, the inhibitors and/or substrates include a sequence having 2, 3, 4, 5, 6, or 7 amino acids in the N-terminal direction from the proline or proline substitute. In the case of FAP inhibitors and/or substrates, these 2, 3, 4, 5, 6, or 7 amino acids include a positively-charged amino acid such as, but not limited to, α,β-diaminopropionic acid, α,γ-diaminobutyric acid, ornithine, β-homoornithine, arginine, β-homoarginine, homoarginine, lysine, homolysine, β-homolysine, and histidine, and a glycine, D-alanine, D-serine, or D-threonine at the $P_2$ position. In the case of POP inhibitors and/or substrates, these 2, 3, 4, 5, 6, or 7 amino acids include at least one positively-charged or negatively-charged amino acid, such as but not limited to, α,β-diaminopropionic acid, α,γ-diaminobutyric acid, ornithine, β-homoornithine, arginine, β-homoarginine, homoarginine, lysine, homolysine, β-homolysine, histidine, aspartic acid, or glutamic acid, and a positively-charged amino acid at $P_2$, such as but not limited to, α,β-diaminopropionic acid, α,γ-diaminobutyric acid, ornithine, β-homoornithine, arginine, β-homoarginine, homoarginine, lysine, homolysine, β-homolysine, or histidine. The inhibitors and/or substrates may also comprise a negatively-charged or aromatic amino acid (e.g., asn, gln, asp, glu, trp, tyr, and phe) at a position downstream (C-terminal direction) from the proline or proline substitute.

In one embodiment of the presently disclosed and claimed inventive concept(s), the inhibitor and/or substrate compounds comprise a spacer (linker or filler) group between the $P_2$ group and the positively-charged amino acid (e.g., arginine) on the N-terminal side. The positively-charged amino acid, e.g., arg, his, or lys or other listed herein, may be in a position equivalent to $P_7$, $P_6$, $P_5$, or $P_4$. The spacer (i.e., linker or filler) between the $P_2$ group and the positively-charged amino acid in one or more of the $P_4$, $P_5$, $P_6$ or $P_7$ positions may for example comprise one or more neutral, non-charged amino acids, e.g., glycine, alanine, leucine, isoleucine, valine, proline, methionine, tryptophan, tyrosine, threonine, serine, β-alanine, γ-amino butyric acid, epsilon amino caproic acid; or $PEG_n$ (n=1-6), $PPG_n$ (n=1-6), amino-$PEG_n$-carboxy group (n=1-6), including for example, 8-amino-3,6-dioxaoctanoic acid, 11-amino-3,6,9-trioxaundecanoic acid, and 14-amino-3, 6, 9, 12-tetraoxatetradecanoic acid, and amino-$PPG_n$-carboxy oligomers (e.g., n=1-6). These individual spacer molecules may be the same (e.g., all glycine, alanine, etc., or other single amino acid or molecule) or different (e.g., more than one type of amino acid, ethylene glycol/propylene glycol, or a hybrid amino acid/amino-$PEG_n$-carboxy or amino-$PPG_n$-carboxy where n=1-6), and may be in a range of 3.0-21 Å (0.3 nm-2.1 nm, or 1 to 7 amino acids) in length. The spacer may be comprised of neutral monomers comprising ethylene glycol for example, or other similar monomer units (e.g., propylene glycol) each having a length of about 0.3 nm, which together have a length of 3.0-21 Å (0.3 nm-2.1 nm) such that the spacer places the positively charged amino acid (or, in the case of a POP substrate and/or inhibitor, a negatively- or positively-charged amino acid) within about 5-25 Å (0.5 nm-2.5 nm) of the proline or proline substitute, analog, or derivative at the $P_1$ position. The inhibitors optionally comprise a blocking group on the N-terminal end for inhibiting protease degradation of the inhibitor.

FAP Inhibitors

In one embodiment, FAP inhibitors of the presently disclosed and claimed inventive concept(s) comprise compounds having Formula I as shown below:

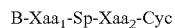   (Formula I).

In Formula I, $Xaa_1$ may be a positively-charged amino acid, including but not limited to, α,β-diaminopropionic acid, α,γ-diaminobutyric acid, ornithine, β-homoornithine, arginine, β-homoarginine, homoarginine, lysine, homolysine, β-homolysine, or histidine, and $Xaa_2$ is glycine, D-alanine, D-serine, or D-threonine. Alternatively, $Xaa_1$ may be absent such that the compound comprises the Formula Ia:

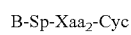   (Formula Ia).

B is a blocking (protecting) group. Examples of such protecting groups include, but are not limited to, aminobenzoyl (Abz), acetyl (Ac), benzoyl (Bz), carbobenzoxy, benzyloxycarbonyl (Z), t-Butyloxycarbonyl (Boc), Furylacryloyl (Fa), Methoxysuccinyl (MeOSuc), Pyroglutamate (Pyr), Pyrazine, Phenylalanine, peptides comprising any combination of 1-3 natural amino acids, and Succinyl (Suc). Where present, the blocking group B may have a molecular weight <400 Da, such as a molecular weight <300 Da. In other embodiments, B may be absent such that the compound comprises the Formula Ib:

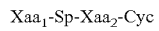   (Formula Ib).

Sp is a spacer molecule, which has a length in a range of 0.3 nm to 0.6 nm to 0.9 nm to 1.2 nm to 1.5 nm to 1.8 nm to 2.1 nm to 2.5 nm (including any subrange therein, such as 0.3 nm to 1.5 nm). Examples of such spacer molecules include, but are not limited to, γ-aminobutyric acid, ε-aminocaproic acid, 8-amino-3,6-dioxaoctanoic acid, 11-amino-3, 6,9-trioxaundecanoic acid, 14-amino-3,6,9,12-tetraoxatetradecanoic acid; α-aminobutyric acid; 5-aminopentanoic acid; 6-aminohexanoic acid; 7-aminoheptanoic acid; 8-aminooctanoic acid; 3-(aminooxy)acetic acid, β-alanine, gly, ala, thr, trp, tyr, met, leu, ile, val, ser, proline, a $PEG_n$; $PPG_n$, an aminocarboxy $PEG_n$ or $PPG_n$, or a combination of any of the above wherein Sp has a length of 0.3 nm to 2.5 nm, and wherein n=1-6.

Cyc is a carbocyclic or heterocyclic ring. The carbocyclic ring may comprise 4, 5, 6, or 7 carbon atoms, for example. The heterocyclic ring may comprise 4, 5, 6, or 7 atoms, for example, wherein at least one atom is a heteroatom such as nitrogen or other atom as discussed elsewhere herein. Alternatively, Cyc may be absent such that the compound comprises the Formula Ic:

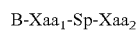   (Formula Ic).

The compound may further comprise one or more amino acids extending upstream from the Cyc group, including, but not limited to, aspartic acid, glutamic acid, glutamine, aspargine, serine, threonine, histidine, tyrosine, alanine, phenylalanine, glycine, valine, leucine, isoleucine, methionine, tyrosine, tryptophan, or any negatively-charged or aromatic amino acid. Examples of Cyc include, but are not limited to, those shown in Table 1 and desirably comprise boronyl prolines (L, D, or D/L), carbonitrile prolines, or nitrile pyrrolidines. Non-limiting examples of various FAP inhibitor compounds of the presently disclosed and claimed inventive concept(s) having the structure of Formula I are shown in Table 2. These FAP inhibitors are generally also inhibitors of POP.

POP Inhibitors

In one embodiment, POP inhibitors of the presently disclosed and claimed inventive concept(s) comprise compounds having Formula II as shown below:

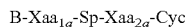

B-Xaa$_{1a}$-Sp-Xaa$_{2a}$-Cyc    (Formula II).

In this embodiment Xaa$_{1a}$ is a negatively- or positively-charged amino acid, including but not limited to, α,β-diaminopropionic acid, α,γ-diaminobutyric acid, ornithine, β-homoornithine, arginine, β-homoarginine, homoarginine, lysine, homolysine, β-homolysine, histidine, aspartic acid, or glutamic acid. Alternatively, Xaa$_{1a}$ may be absent such that the compound comprises the Formula IIc:

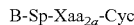

B-Sp-Xaa$_{2a}$-Cyc    (Formula IIc).

Xaa$_{2a}$ is a positively-charged amino acid, including but not limited to, α,β-diaminopropionic acid, α,γ-diaminobutyric acid, ornithine, β-homoornithine, arginine, β-homoarginine, homoarginine, lysine, homolysine, β-homolysine, or histidine. Xaa$_{1a}$ and Xaa$_{2a}$ may be the same when both are positively-charged.

B is a blocking (protecting) group. Examples of such protecting groups include, but are not limited to, aminobenzoyl (Abz), acetyl (Ac), benzoyl (Bz), carbobenzoxy, benzyloxycarbonyl (Z), t-Butyloxycarbonyl (Boc), Furylacryloyl (Fa), Methoxysuccinyl (MeOSuc), Pyroglutamate (Pyr), Pyrazine, Phenylalanine, peptides comprising any combination of 1-3 natural amino acids, and Succinyl (Suc). Where present, the blocking group B may have a molecular weight <400 Da, such as a molecular weight <300 Da. In other embodiments, B may be absent such that the compound comprises the Formula IIa:

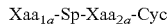

Xaa$_{1a}$-Sp-Xaa$_{2a}$-Cyc    (Formula IIa).

Sp is a spacer molecule which may have a length in a range of 0.3 nm to 0.6 nm to 0.9 nm to 1.2 nm to 1.5 nm to 1.8 nm to 2.1 nm to 2.5 nm (including any subrange therein, such as 0.3 nm to 1.5 nm). Examples of such spacer molecules include, but are not limited to, γ-aminobutyric acid; ε-aminocaproic acid; 8-amino-3,6-dioxaoctanoic acid; 11-amino-3,6,9-trioxaundecanoic acid; 14-amino-3,6,9,12-tetraoxatetradecanoic acid; α-aminobutyric acid; 5-aminopentanoic acid; 6-aminohexanoic acid; 7-aminoheptanoic acid; 8-aminooctanoic acid; 3-(aminooxy)acetic acid; β-alanine, glycine, alanine, threonine, tryptophan, tyrosine, methionine, leucine, isoleucine, valine, serine, or proline; PEG$_n$ (wherein n=1-6); PPG$_n$ (wherein n=1-6); an aminocarboxy PEG$_n$ or PPG$_n$ (wherein n=1-6); or a combination of any of the above, so long as Sp has a length of 0.3 nm to 2.5 nm, and. Particular versions of Sp are leucine, isoleucine, valine, and alanine.

Cyc is a carbocyclic or heterocyclic ring. The carbocyclic ring may comprise 4, 5, 6, or 7 carbon atoms, for example. The heterocyclic ring may comprise 4, 5, 6, or 7 atoms, for example wherein at least one atom is a heteroatom such as nitrogen or other atom as discussed elsewhere herein. The compound may further comprise one or more amino acids extending upstream from the Cyc group, including, but not limited to aspartic acid, glutamic acid, glutamine, aspargine, serine, threonine, histidine, tyrosine, alanine, phenylalanine, glycine, valine, leucine, isoleucine, methionine, tyrosine, tryptophan, or any negatively-charged or aromatic amino acid. Examples of Cyc include, but are not limited to, those shown in Table 1 and desirably comprise boronyl prolines (L, D, or D/L), carbonitrile prolines or nitrile pyrrolidines. Non-limiting examples of various POP inhibitor compounds of the presently disclosed and claimed inventive concept(s) having the structure of Formula II are shown in Tables 3-5.

In a particular embodiment, the inhibitor compounds of the presently disclosed and claimed inventive concept(s) are non-immunogenic (i.e., induce no antibody response) and have zero cell membrane permeability, as well as a solubility in water of at least 5 mg/ml.

The inhibitors described herein may comprise isostere bonds. For example but not by way of limitation, in a compound comprising acetyl-arginyl-amino-PEG$_2$-carboxy-D-alanyl-L-boroproline, the carbonyl of the carboxyl group of the arginine moiety may be reduced to a methylene group to form a reduced isostere bond between the residual arginine group and the amino-PEG$_2$-carboxy spacer group. Any of the inhibitor compounds of the presently disclosed and claimed inventive concept(s) may comprise such a reduced isostere bond, or may be formed with the regular peptide bond, between the arginine (or other charged amino acid) and the spacer group, i.e., between Xaa$_1$ (or Xaa$_{1a}$) and Sp. The reduced isostere bond is effective in further reducing peptidase activity upon the compound.

The compound may further comprise, with, or in place of B, an N-terminal oligopeptide having 1 to 10 amino acids extending in an N-terminal direction from Xaa$_1$ or Xaa$_{1a}$ and/or a C-terminal oligopeptide having 1-10 amino acids extending in a C-terminal direction from Cyc, wherein the N-terminal oligopeptide and C-terminal oligopeptide may comprise one or more of the 20 naturally-occurring amino acids in any combination.

In certain embodiments of a FAP inhibitor compound of the presently disclosed and claimed inventive concept(s), D-ala replaces gly, because it was observed in a surprising result that this unnatural amino acid significantly amplified inhibitory selectivity of the compound for FAP or APCE versus DPPIV. D-ser and D-thr may also substitute for gly. For example, as shown in Table 7, an inhibitor compound comprising D-ala-L-boroPro had an APCE K$_i$ of 5.7 nM and DPPIV Ki of 6130 nM, while a compound comprising gly-boroPro had an APCE K$_i$ of 1.8 nM and DPPIV K$_i$ of 440 nM. Unlike FAP, DPPIV is expressed by normal tissues and is involved in normal physiologic reactions; therefore, a high K$_i$ (low affinity) for DPPIV is greatly desired. The D-amino acid-containing inhibitors may inhibit APCE with a K$_i$ in the low nM range (e.g., such as <100 nM, <50 nM, <20 nM, <15 nM, or <10 nM) and do not significantly inhibit DPPIV (e.g., >5,000 nM), unless used at unacceptable and unusually high concentrations. In a particular version of the presently disclosed and claimed inventive concept(s), the inhibitor compounds are highly selective for APCE and FAP versus DPPIV. For example, the ratio of K$_i$ (DPPIV): K$_i$ (APCE/FAP) may be >200, such as >500, or >600, or >700, or >800, or >900, or >1,000. The K$_i$ (DPPIV) may be >200 nM, such as >500 nM, >1,000 nM, >2,500 nM, >4,000 nM, >5,000 nM, >6,000 nM, >7,500 nM, or >10,000 nM. The molecular weight of the inhibitor compound of the presently disclosed and claimed inventive concept(s) may be <1000 Da, such as <800 Da, or <600 Da. The inhibitors which are specific for POP may have a $K_i$ (POP)<100 nM while the $K_i$ (FAP) is >200 nM or >500 μM. The inhibitors of POP may have a Ki (DPPIV)>200 nM, such as >500 nM, >1,000 nM, >2,500 nM, >4,000 nM, >5,000 nM, >6,000 nM, >7,500 nM, or >10,000 nM.

The inhibitors described herein exhibit very good to excellent selectivity and are highly water soluble; in addition, given this length and the lack of exposed amino-terminal amino group, the inhibitors are not prone to cyclization with resultant loss of activity. In certain embodiments, a chemotherapeutic agent, such as described below, can be linked to the inhibitor molecule, directly via an exposed amino or carboxy group or via a linking group. In an alternative embodiment, the presently disclosed and claimed inventive concept(s) includes a compound which comprises the "stalk" portion of the compound of Formula I, i.e., B-Xaa$_1$-Sp-Xaa$_2$ (Formula Ic), wherein Xaa$_1$ is a positively-charged amino acid, such as but not limited to, α,β-diaminopropionic acid, α,γ-diaminobutyric acid, ornithine, β-homoornithine, arginine, β-homoarginine, homoarginine, lysine, homolysine, β-homolysine, or histidine (or is absent), and Xaa$_2$ is glycine, D-alanine, D-serine, or D-threonine. The presently disclosed and claimed inventive concept(s) also include the stalk portion of Formula II, i.e., B-Xaa$_{1a}$-Sp-Xaa$_{2a}$ (Formula IIb), wherein Xaa$_{1a}$ is a negatively- or positively-charged amino acid, such as but not limited to, α,β-diaminopropionic acid, α,γ-diaminobutyric acid, ornithine, β-homoornithine, arginine, β-homoarginine, homoarginine, lysine, homolysine, β-homolysine, histidine, aspartic acid, or glutamic acid, and Xaa$_{2a}$ is a positively-charged amino acid, such as but not limited to, α,β-diaminopropionic acid, α,γ-diaminobutyric acid, ornithine, β-homoornithine, arginine, β-homoarginine, homoarginine, lysine, homolysine, β-homolysine, or histidine (or is absent). Xaa$_{1a}$ and Xaa$_{2a}$ may be the same when both are positively-charged. The "stalks" may be used as precursors of the inhibitor compounds, or linked to a targeting agent or delivery agent, to deliver a "warhead" (i.e., Cyc, or other compound) to FAP or POP, respectively, for example. The presently disclosed and claimed inventive concept(s) is thus directed to compounds comprising or otherwise based on these "stalks" as a component, and to the use of these compounds in any therapeutic, diagnostic, or assay method described, contemplated, or enabled herein. The compound may be disposed in a pharmaceutically-acceptable carrier as described elsewhere herein.

FAP and POP Substrates

Embodiments of the presently disclosed and claimed inventive concept(s) include substrates for APCE, FAP, and/or POP, and particularly substrates which are specific for POP.

FAP Substrates

In one embodiment, the presently disclosed and claimed inventive concept(s) includes substrates of FAP (and APCE) having Formula III as shown below:

     (Formula III).

B is a blocking (protecting) group. Examples of such protecting groups include, but are not limited to, aminobenzoyl (Abz), acetyl (Ac), benzoyl (Bz), carbobenzoxy, benzyloxycarbonyl (Z), t-Butyloxycarbonyl (Boc), Furylacryloyl (Fa), Methoxysuccinyl (MeOSuc), Pyroglutamate (Pyr), Pyrazine, Phenylalanine, peptides comprising any combination of 1-3 natural amino acids, and Succinyl (Suc). Where present, the blocking group B may have a molecular weight <400 Da, such as a molecular weight <300 Da. In other embodiments, B may be absent such that the compound comprises the Formula IIIa:

     (Formula IIIa).

In Formula III, Xaa$_1$ is a positively-charged amino acid such as, but not limited to, α, β-diamino propionic acid, α,γ-diaminobutyric acid, ornithine, β-homoornithine, arginine, β-homoarginine, homoarginine, lysine, homolysine, β-homolysine, or histidine. Xaa$_2$ is glycine, D-alanine, D-serine, or D-threonine.

Sp is a spacer molecule comprising one or more of γ-aminobutyric acid; ε-aminocaproic acid; 8-amino-3,6-dioxaoctanoic acid; 11-amino-3,6,9-trioxaundecanoic acid; 14-amino-3,6,9,12-tetraoxatetradecanoic acid; α-aminobutyric acid; 5-aminopentanoic acid; 6-aminohexanoic acid; 7-aminoheptanoic acid; 8-aminooctanoic acid; 3-(aminooxy)acetic acid; 3-alanine; alanine, threonine, tryptophan, tyrosine, methionine, leucine, isoleucine, valine, serine, proline; PEG$_n$ (n=1-6); PPG$_n$ (n=1-6); aminocarboxy PEG$_n$ (n=1-6); aminocarboxy PPG$_n$ (n=1-6); or a combination of any of the above, so long as Sp has a length in a range of 0.3 nm to 0.6 nm to 0.9 nm to 1.2 nm to 1.5 nm to 1.8 nm to 2.1 nm to 2.5 nm (including any subrange therein, such as 0.3 nm to 1.5 nm).

Pro is proline or a proline analog which can form a $P_1$-$P_1'$ bond which is cleavable by FAP. Rep may be absent, or is a reporter group such as, but not limited to, at least one of 7-amido-4-methylcoumarin (AMC), 7-amino-trifluoromethylcoumarin (AFC), ethyl ester (OEt), methyl ester (OMe), 2-Naphthylamide (2NA), p-Nitroanilide (p-NA), p-Nitrophenyl ester (ONp), or Thiobenzyl ester (SBzl). The substrate may further comprise peptide(s) (n=1-10) extending from the N-terminal amino acid and/or from the C-terminal amino acid thereof. The compounds of Formula III generally are also substrates of POP.

POP Substrates

In another embodiment, the presently disclosed and claimed inventive concept(s) includes substrates of POP having Formula IV as shown below:

     (Formula IV).

B is a blocking (protecting) group. Examples of such protecting groups include, but are not limited to, aminobenzoyl (Abz), acetyl (Ac), benzoyl (Bz), carbobenzoxy, benzyloxycarbonyl (Z), t-Butyloxycarbonyl (Boc), Furylacryloyl (Fa), Methoxysuccinyl (MeOSuc), Pyroglutamate (Pyr), Pyrazine, Phenylalanine, peptides comprising any combination of 1-3 natural amino acids, and Succinyl (Suc). Where present, the blocking group B may have a molecular weight <400 Da, such as <300 Da. In other embodiments, B may be absent such that the compound comprises the Formula IVa:

     (Formula IV).

In Formula IV, Xaa$_{1a}$ is a negatively- or positively-charged amino acid, such as but not limited to, α,β-diaminopropionic acid, α,γ-diaminobutyric acid, ornithine, β-homoornithine, arginine, β-homoarginine, homoarginine, lysine, homolysine, β-homolysine, histidine, aspartic acid, or glutamic acid.

Xaa$_{2a}$ is a positively-charged amino acid, such as but not limited to, α,β-diaminopropionic acid; α,γ-diaminobutyric acid; ornithine; β-homoornithine; arginine; β-homoarginine; homoarginine; lysine; homolysine; β-homolysine; or histidine. Xaa$_{1a}$ and Xaa$_{2a}$ may be the same when both are positively-charged.

Sp is a spacer molecule comprising one or more of γ-aminobutyric acid; ε-aminocaproic acid; 8-amino-3,6-dioxaoctanoic acid; 11-amino-3,6,9-trioxaundecanoic acid; 14-amino-3,6,9,12-tetraoxatetradecanoic acid; α-aminobutyric acid; 5-aminopentanoic acid; 6-aminohexanoic acid; 7-aminoheptanoic acid; 8-aminooctanoic acid; 3-(aminooxy)acetic acid; β-alanine; alanine, threonine, tryptophan, tyrosine, methionine, leucine, isoleucine, valine, serine, proline; $PEG_n$ (n=1-6); $PPG_n$ (n=1-6); aminocarboxy $PEG_n$ (n=1-6); aminocarboxy $PPG_n$ (n=1-6); or a combination of any of the above, so long as Sp has a length in a range of 0.3 nm to 0.6 nm to 0.9 nm to 1.2 nm to 1.5 nm to 1.8 nm to 2.1 nm to 2.5 nm (including any subrange therein, such as 0.3 nm to 1.5 nm).

Pro is proline or a proline analog which can form a $P_1$-$P_1'$ bond which is cleavable by POP. Rep may be absent, or is a reporter group such as, but not limited to, at least one of 7-amido-4-methylcoumarin (AMC), 7-amino-trifluoromethylcoumarin (AFC), ethyl ester (OEt), methyl ester (OMe), 2-Naphthylamide (2NA), p-Nitroanilide (p-NA), p-Nitrophenyl ester (ONp), or Thiobenzyl ester (SBzl). The substrate may further comprise peptides (n=1-10) extending from the N-terminal amino acid and/or from the C-terminal amino acid.

Screening for APCE, FAP and POP Inhibitors

Certain embodiments of the presently disclosed and claimed inventive concept(s) also include methods of screening for inhibitors of APCE, FAP, and/or POP. In the method, at least one of an APCE, FAP, or POP enzyme substrate such as is contemplated herein is provided; the substrate may particularly comprise a reporter group. A quantity of at least one of APCE, FAP, and POP if provided, and the enzyme is exposed to an inhibitor candidate to form a test mixture. The test mixture is combined with the substrate, and the fluorescence emission from the test mixture is measured to identify when the activity of the enzyme is inhibited by the enzyme inhibitor candidate. Any cleavable substrate of APCE, FAP, and/or POP which produces an observable signal (fluorescence or other signal), such as discussed elsewhere herein, may be used. In one embodiment, the presently disclosed and claimed inventive concept(s) is directed to a method of screening for inhibitors of POP. In the method, a substrate compound of Formula IV which is cleavable by POP, and which has signaling activity when cleaved by the POP, is obtained along with quantity of POP. The POP is then exposed to a POP inhibitor candidate to form a test mixture, and the test mixture is combined with the substrate compound. The signal emitted from the test mixture/substrate compound mixture is measured to identify a POP inhibitor which inhibits the activity of the POP.

In one particular embodiment, the presently disclosed and claimed inventive concept(s) is directed to a compound (and to a composition containing the compound) having the formula:

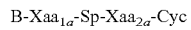

B-$Xaa_{1a}$-Sp-$Xaa_{2a}$-Cyc    (Formula II).

B is defined as a protecting group or is absent. $Xaa_{1a}$ is a positively-charged or negatively-charged amino-acid, or is absent. Sp is a spacer molecule having a length in the range of 0.3 nm to 2.5 nm. $Xaa_{2a}$ is a positively-charged amino acid. Cyc is a carbocyclic or heterocyclic compound.

$Xaa_{1a}$ may be, for example, α,β-diaminopropionic acid, α,γ-diaminobutyric acid, ornithine, β-homoornithine, arginine, β-homoarginine, homoarginine, lysine, homolysine, β-homolysine, histidine, aspartic acid or glutamic acid. $Xaa_{2a}$ may be, for example, α,β-diaminopropionic acid, α,γ-diaminobutyric acid, ornithine, β-homoornithine, arginine, β-homoarginine, homoarginine, lysine, homolysine, β-homolysine, or histidine. Sp may be selected from the group consisting of, for example, γ-aminobutyric acid; ε-aminocaproic acid; 8-amino-3,6-dioxaoctanoic acid; 11-amino-3,6,9-trioxaundecanoic acid; 14-amino-3,6,9,12-tetraoxatetradecanoic acid; α-aminobutyric acid; 5-aminopentanoic acid; 6-aminohexanoic acid; 7-aminoheptanoic acid; 8-aminooctanoic acid; 3-(aminooxy)acetic acid; β-alanine; glycine; alanine; threonine; tryptophan; tyrosine; methionine; leucine; isoleucine; valine; serine; proline; ethylene glycol; $PEG_n$ (wherein n=1-6); propylene glycol; $PPG_n$ (wherein n=1-6); amino-$PEG_n$-carboxy (wherein n=1-6); amino-$PPG_n$-carboxy (wherein n=1-6); and combinations thereof. B may be, for example, at least one of aminobenzoyl (Abz), acetyl (Ac), benzoyl (Bz), benzyloxycarbonyl (Z), t-Butyloxycarbonyl (Boc), Furylacryloyl (Fa), Methoxysuccinyl (MeOSuc), Pyroglutamate (Pyr), Pyrazine, Phenylalanine, a 1-3 mer peptide, and Succinyl (Suc).

Cyc may be, for example, a 4, 5, 6, or 7-member carbon carbocycle. Cyc may be, for example, a 4, 5, 6, or 7-member carbon heterocycle, and may comprise a nitrogen heteroatom. Cyc may comprise, for example, a boronylproline, proline carbonitrile, nitrile pyrrolidone, or cyanopyrrolidine. Sp may be selected from the group consisting of, for example, ethylene glycol, $PEG_n$ (wherein n=1-6), propylene glycol, 8-amino-3,6-dioxaoctanoic acid, $PPG_n$ (wherein n=1-6)), amino-$PEG_n$-carboxy group (wherein n=1-6), an amino-$PPG_n$-carboxy group (wherein n=1-6), and combinations thereof. The compound may comprise an isostere bond between $Xaa_{1a}$ and Sp. $Xaa_{1a}$ may comprise, for example, a methylene group in substitution for the carbonyl group adjacent Sp. Sp may have a length in a range of 0.6 nm to 1.75 nm. Sp may be, for example, leucine, isoleucine, valine, or alanine. The compound may further comprise a 1-10mer peptide or oligopeptide extending from Cyc in the C-terminal direction.

In one embodiment, the compound is capable of binding to the active site of POP at a $K_i$<100 nM, <50 nM, or <20 nM, for example, and capable of binding to DPPIV at a Ki>500 nM, or >1000 nM or greater and/or has a Ki (DPPIV):Ki (POP) ratio >500. In one embodiment B is an acetyl or pyrazine; $Xaa_{1a}$ is lysine; $Xaa_{2a}$ is arginine; and Cyc is L-boroproline. In one embodiment the compound is combined with a pharmaceutically-acceptable carrier or vehicle to form a pharmaceutical composition.

In another particular embodiment of the presently disclosed and claimed inventive concept(s), a pharmaceutical composition is provided that includes any of the compounds described herein disposed within or otherwise combined with a pharmaceutically-acceptable carrier or vehicle. In one embodiment, the compound is the compound of Formula II as described herein above. In particular embodiments, $Xaa_{1a}$ of the compound is lysine, and the Sp of the compound is leucine, isoleucine, valine, or alanine.

Yet another particular embodiment of the presently disclosed and claimed inventive concept(s) is directed to a method of inhibiting activity of prolyl oligopeptidase (POP) in a POP-expressing cell or tissue, comprising administering to the POP-expressing cell or tissue any of the compounds described herein. In one embodiment, the compound is the compound of Formula II as described herein. The POP-expressing cells or tissues to which the compound is administered may be cancer cells and/or activated fibroblast cells. The compound may be administered to cells and/or tissues in vitro or in vivo. For example, the compound may be administered to a patient, such as but not limited to, a mammalian patient. In one embodiment of the method, formation of acetyl-ser-asp-lys-pro is inhibited upon administration of the compound to the cells or tissues.

Another particular embodiment of the presently disclosed and claimed inventive concept(s) is directed to a method of inhibiting angiogenesis in a tissue. In the method, a pharmaceutically acceptable amount of any of the compounds described herein is administered to a tissue exhibiting angiogenesis and/or having the potential to exhibit angiogenesis, thereby inhibiting angiogenesis in the tissue. In one embodiment, the compound is the compound of Formula II as described herein above. The tissue exhibiting angiogenesis and/or having the potential to exhibit angiogenesis to which the compound is administered may comprise cancer cells and/or activated fibroblast cells. The compound may be administered to cells and/or tissues in vitro or in vivo. For example, the compound may be administered to a patient, such as but not limited to, a mammalian patient. In one embodiment of the method, formation of acetyl-ser-asp-lys-pro is inhibited upon administration of the compound to the cells or tissues.

Yet another particular embodiment of the presently disclosed and claimed inventive concept(s) is directed to a method of treating cancer in a subject. In the method, a therapeutically-effective amount of any of the compounds described herein is administered to a subject in need of such therapy. In one embodiment, the compound is the compound of Formula II as described herein above.

Another particular embodiment of the presently disclosed and claimed inventive concept(s) is directed to a compound (and to a composition containing the compound) having the formula:

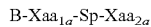

B-Xaa$_{1a}$-Sp-Xaa$_{2a}$     (Formula IIb).

B is defined as a protecting group or is absent. Xaa$_{1a}$ is a positively-charged or negatively-charged amino-acid, or is absent. Sp is a spacer molecule having a length in the range of 0.3 nm to 2.5 nm. Xaa$_{2a}$ is a positively-charged amino acid.

The presently disclosed and claimed inventive concept(s) is further directed to a method of inhibiting activity of prolyl oligopeptidase (POP) in a subject suffering from a disorder for which inhibition of POP provides a therapeutically-effective benefit. In the method, any of the POP inhibitors described herein is administered to a subject in need of such therapy. In one embodiment, the therapeutically-effective benefit is the inhibition of angiogenesis. In one embodiment, the compound is the compound of Formula II or Formula IIb as described herein above.

Certain embodiments of the presently disclosed and claimed inventive concept(s) include FAP and POP inhibitor compounds described herein which are conjugated to carrier compounds which are able to pass through the cell membrane, including, but not limited to, protein transduction domains (PTDs). PTDs are positively charged peptides or peptide-like molecules that permeate cell membrane lipid bilayers. Typically PTDs contain several arginine residues and can be used to deliver other agents, such as peptides, proteins, oligonucleotides or small molecules through a cell membrane and into the cytosol. One PTD is a highly efficient molecular transporter formed by synthesizing an oligomer of arginines alternating with εACAs. PTDs are well-known in the art. Examples of PTDs which may be used herein are shown, for example, in U.S. Pat. Nos. 7,166,692; 7,217,539; 7,053,200; 6,835,810; 6,645,501; and Published US Patent Applications 2002/0009491; 2003/0032593; 2003/0162719; 2006/0159719; 2006/0293234; and 2007/0105775, each of which is expressly incorporated herein in its entirety by reference.

Similarly, based on the results showing that the inhibitors likewise inhibit FAP with high sensitivity and specificity, the inhibitors can be used to selectively inhibit the proteolytic activity of FAP on cell surfaces of fibroblasts and cancer cells towards collagen within the extracellular matrix, and without impacting other prolyl-specific proteinases (e.g., DPPIV) for which it has no specificity thus enabling analysis of various characteristics of the sample with other prolyl-specific proteinases present while FAP is inhibited. Further, the high aqueous solubility of the particular inhibitors (>500 μg/ml) indicates they will not permeabilize the universal highly lipophilic, hydrophobic nature of cell membranes.

Utility

Further to, and in addition to the utilities already described hereinabove, in one embodiment, a subject may be treated with a compound described herein in a manner and in an amount so as to treat any of the conditions, diseases or disorders described herein. For example, the compounds can be used to inhibit proliferation of a primary tumor, or to inhibit metastatic spread or growth while minimizing the potential for systemic toxicity. In certain embodiments, the abnormal mammalian cell proliferation is manifested as a tumor. Some conditions intended to be treated by the present methods using the present compounds include benign (i.e., non-cancerous), pre-malignant and malignant (i.e., cancerous) tumors especially those characterized by angiogenesis. In some embodiments, the condition characterized by abnormal mammalian cell proliferation is further characterized by the presence of reactive stromal fibroblasts. Inhibitors of POP described herein are intended to inhibit angiogenesis, particularly angiogenesis which is related to such malignancies. Inhibitors of POP and FAP described herein may also be used to treat conditions which exhibit excessive or undesirable stromal growth such as idiopathic pulmonary fibrosis, rheumatoid arthritis, and peritoneal and pleural adhesions. Effective treatment is defined in at least one embodiment as resulting in reduced tumor growth and/or tumor shrinkage, defined, for example, as a reduction in tumor volume of at least a 10%, or at least 25%, or at least 50% after a predetermined course of treatment.

In other embodiments, the abnormal mammalian cell proliferation treated with the presently described inhibitors is a carcinoma, a sarcoma, or a melanoma or others described elsewhere herein. More particularly, the condition may be, but is not limited to, a breast cancer, colorectal cancer, ovarian cancer, prostate cancer, pancreatic cancer, kidney cancer, lung cancer, melanoma, or fibrosarcoma, or bone and connective tissue sarcomas, including, but not limited to, osteosarcoma and fibrosarcoma. The abnormal mammalian cell proliferation may be epithelial cell-derived, meaning that it is epithelial cells which are abnormally proliferating. Some conditions characterized by abnormal mammalian epithelial cell proliferation include adenomas of epithelial tissues such as the breast, colon, pancreas, lung, and prostate, as well as malignant tumors identified above. According to other embodiments of the presently disclosed and claimed inventive concept(s), a method is provided for treating a subject having a metastasis of epithelial origin.

According to some embodiments of the presently disclosed and claimed inventive concept(s), the inhibitor (agent) is administered locally. In some embodiments, the agent is targeted to a tumor. This can be achieved by the particular mode of administration. For example, certain more easily accessible tumors such as breast or prostate tumors may be targeted by direct needle injection to the site of the lesion. Lung tumors may be targeted, for example, by the use of inhalation as a route of administration.

In some embodiments, the agents may be administered in a systemic manner, via administration routes such as, but not limited to, oral, intravenous, intramuscular and intraperitoneal administration. Systemic administration routes may be desired, for example, if the subject has metastatic lesions. In other embodiments, the agent is administered in a sustained release formulation.

In administering the present compounds to subjects, dosing amounts, dosing schedules, routes of administration and the like may be selected so as to affect the other known activities of these compounds. For example, amounts, dosing schedules and routes of administration can be selected as described herein, whereby therapeutically effective levels for inhibiting proliferation are provided, yet are provided at levels which do not affect other proteins (e.g., enzymes necessary for healthy function such as DPPIV) in the subject. In some embodiments of the presently disclosed and claimed inventive concept(s), a method is provided in which the inhibitor is administered in combination with surgery (before, during, or after) to remove an abnormal proliferative cell mass.

In another aspect, the FAP and/or POP inhibitors as described herein may be used in treatment for inhibiting angiogenesis in a subject having a condition characterized by abnormal mammalian cell proliferation, such as a cancer, comprising administering to a subject in need of such treatment, an agent in an amount effective to inhibit angiogenesis in an abnormal proliferative cell mass, wherein the agent is an inhibitor as described herein.

In one embodiment, an inhibitor having Formula I or II, or a combination thereof, is provided along with at least one other anti-cancer compound (i.e., an anti-cancer compound other than a compound having Formula I or Formula II or as otherwise contemplated herein), and a pharmaceutically acceptable carrier. In another aspect, a pharmaceutical preparation is provided which comprises a compound having Formula I or Formula II, or a combination thereof, at least one other anti-angiogenic compound (i.e., an anti-angiogenic compound other than a compound of Formula I or Formula II, or as otherwise contemplated herein), and a pharmaceutically acceptable carrier.

In other embodiments, anti-cancer cocktails containing an inhibitor compound of the presently disclosed and claimed inventive concept(s) and other anti-proliferative compounds and/or other anti-angiogenic compounds as described herein are also provided. In still other embodiments, compounds having the Formula I or Formula II, or combinations thereof, are used in the preparation of a medicament for treating subjects having conditions characterized by abnormal mammalian cell proliferation.

In still other embodiments, the inhibitory compound may be targeted to a cell mass (e.g., a tumor) through the use of a targeting compound specific for a particular tissue or tumor type. In some embodiments, the inhibitors may be targeted to primary or in some instances, secondary (i.e., metastatic) lesions through the use of targeting compounds which preferentially recognize a cell surface marker.

As described herein, the inhibitors and substrates of the presently disclosed and claimed inventive concept(s) comprise peptides or peptidomimetics which may include non-amino acid residues such as saccharides, fatty acids, sterols, isoprenoids, purines, pyrimidines, derivatives or structural analogs of the above, or combinations thereof and the like. In particular, as described herein, it is possible to substitute non-naturally occurring amino acids as described herein for the "$P_1$" proline residue. In one embodiment, the $P_1$ group is an analog of proline in which the carboxylate group (COOH) is replaced with a boronyl group ($BOH_2$). Alternative compounds of the presently disclosed and claimed inventive concept(s) have an analogous structure in which the boronyl group is replaced by, for example, a nitrile, a carbonitrile, carboxynitrile, a phosphonate or a fluoroalkylketone, alphaketos, N-peptiolyl-O-(acylhydroxylamines), azapeptides, azetidines, fluoroolefins dipeptide isoesters, peptidyl (alpha-aminoalkyl) phosphonate esters, aminoacyl pyrrolidine-2-nitriles and 4-cyanothiazolidides, or other structures for example as shown in Table 1.

As noted herein, certain embodiments of the presently disclosed and claimed inventive concept(s) include methods for treating a subject having a condition characterized by an abnormal cell proliferation or other conditions described herein. As used herein, the term subject is intended to refer to a mammal including, but not limited to, humans, apes, monkeys, other nonhuman primates, dogs, cats, sheep, llamas, goats, horses, cattle, zoo animals, pigs, and rodents. As used herein, the terms subject and patient are used interchangeably. An abnormal mammalian cell proliferation disorder or condition, as used herein, refers to a localized region of cells (e.g., a tumor) which exhibit an abnormal (e.g., increased) rate of division as compared to their normal tissue counterparts.

In one aspect, as noted, the presently disclosed and claimed inventive concept(s) includes methods for treating a subject having a condition characterized by an abnormal epithelial cell proliferation. Epithelial cells are cells occurring in one or more layers which cover the entire surface of the body and which line most of the hollow structures of the body, excluding the blood vessels, lymph vessels, and the heart interior which are lined with endothelium, and the chest and abdominal cavities which are lined with mesothelium. Examples of such epithelial cells include, but are not limited to, cells of the anterius corneae, anterior epithelium of cornea, Barrett's epithelium, capsular epithelium, ciliated epithelium, columnar epithelium, corneal epithelium, cubical epithelium, cuboidal epithelium, epithelium eductus semicircularis, enamel epithelium, false epithelium, germinal epithelium, gingival epithelium, glandular epithelium, glomerular epithelium, laminated epithelium, epithelium of lens, epithelium lentis, mesenchymal epithelium, olfactory epithelium, pavement epithelium, pigmentary epithelium, pigmented epithelium, protective epithelium, pseudostratified epithelium, pyramidal epithelium, respiratory epithelium, rod epithelium, seminiferous epithelium, sense epithelium, sensory epithelium, simple epithelium, squamous epithelium, stratified epithelium, subcapsular epithelium, sulcular epithelium, tessellated epithelium, and transitional epithelium.

One category of conditions characterized by abnormal epithelial cell proliferation is proliferative dermatologic disorders. These include, but are not limited to, conditions such as keloids, seborrheic keratosis, papilloma virus infection (e.g., producing verruca vulbaris, verruca plantaris, verruca plana, condylomata, etc.) and eczema. An epithelial precancerous lesion is a skin lesion which has a propensity to develop into a cancerous condition. Epithelial precancerous skin lesions also arise from other proliferative skin disorders such as hemangiomas, keloids, eczema, and papilloma virus infections producing verruca vulbaris, verruca plantaris and verruca planar. The symptoms of the epithelial precancerous lesions include skin-colored or red-brown macule or papule with dry adherent scales. Actinic keratosis is the most common epithelial precancerous lesion among fair skinned individuals. It is usually present as lesions on the skin which may or may not be visually detectable. The size and shape of the lesions varies. This is a photosensitive disorder and may be aggravated by exposure to sunlight. Bowenoid actinic keratosis is another form of an epithelial precancerous lesion. In some cases, the lesions may develop into an invasive form of squamous cell carcinoma and may pose a significant threat of metastasis. Other types of epithelial precancerous lesions include, but are not limited to, hypertrophic actinic keratosis, arsenical keratosis, hydrocarbon keratosis, thermal keratosis, radiation keratosis, viral keratosis, Bowen's disease, erythroplaquia of queyrat, oral erythroplaquia, leukoplakia, and intraepidermal epithelialoma.

As noted above, another category of conditions characterized by abnormal epithelial cell proliferation is tumors of epithelial origin. Epithelial tumors are known to those of ordinary skill in the art and include, but are not limited to, benign and premalignant epithelial tumors, such as breast fibroadenoma and colon adenoma, and malignant epithelial tumors. Malignant epithelial tumors include primary tumors, also referred to as carcinomas, and secondary tumors, also referred to as metastases of epithelial origin. Carcinomas intended for treatment with the methods of the presently disclosed and claimed inventive concept(s) include, but are not limited to, acinar carcinoma, acinous carcinoma, alveolar adenocarcinoma (also called adenocystic carcinoma, adenomyoepithelioma, cribriform carcinoma and cylindroma), carcinoma adenomatosum, adenocarcinoma, carcinoma of adrenal cortex, alveolar carcinoma, alveolar cell carcinoma (also called bronchiolar carcinoma, alveolar cell tumor and pulmonary adenomatosis), basal cell carcinoma, carcinoma basocellulare (also called basaloma, or basiloma, and hair matrix carcinoma), basaloid carcinoma, basosquamous cell carcinoma, breast carcinoma, bronchioalveolar carcinoma, bronchiolar carcinoma, bronchogenic carcinoma, cerebriform carcinoma, cholangiocellular carcinoma (also called cholangioma and cholangiocarcinoma), chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epibulbar carcinoma, epidermoid carcinoma, carcinoma epitheliale adenoides, carcinoma exulcere, carcinoma fibrosum, gelatiniform carcinoma, gelatinous carcinoma, giant cell carcinoma, gigantocellulare, glandular carcinoma, granulosa cell carcinoma, hair-matrix carcinoma, hematoid carcinoma, hepatocellular carcinoma (also called hepatoma, malignant hepatoma and hepatocarcinoma), Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, lenticular carcinoma, carcinoma lenticulare, lipomatous carcinoma, lymphoepithelial carcinoma, carcinoma mastitoides, carcinoma medullare, medullary carcinoma, carcinoma melanodes, melanotic carcinoma, mucinous carcinoma, carcinoma muciparum, carcinoma mucocellulare, mucoepidermoid carcinoma, carcinoma *mucosum*, mucous carcinoma, carcinoma myxomatodes, nasopharyngeal carcinoma, carcinoma *nigrum*, oat cell carcinoma, carcinoma ossificans, osteoid carcinoma, ovarian carcinoma, papillary carcinoma, periportal carcinoma, preinvasive carcinoma, prostate carcinoma, renal cell carcinoma of kidney (also called adenocarcinoma of kidney and hypernephroid carcinoma), reserve cell carcinoma, carcinoma sarcomatodes, scheinderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squarrous carcinoma, squamous cell carcinoma, string carcinoma, carcinoma telangiectaticum, carcinoma telangiectodes, transitional cell carcinoma, carcinoma *tuberosum*, tuberous carcinoma, verrucous carcinoma, carcinoma vilosum. In certain embodiments, the methods of the inventive concept(s) are used to treat subjects having cancer in at least one or more of the breast, cervix, ovary, prostate, lung, colon, rectum, pancreas, stomach and kidney.

Other conditions characterized by an abnormal mammalian cell proliferation to be treated by the methods described herein include, but are not limited to, sarcomas. Sarcomas are rare mesenchymal neoplasms that arise in bone and soft tissues. Different types of sarcomas are recognized and these include: liposarcomas (including myxoid liposarcomas and pleiomorphic liposarcomas), leiomyosarcomas, rhabdomyosarcomas, malignant peripheral nerve sheath tumors (also called malignant schwannomas, neurofibrosarcomas, or neurogenic sarcomas), Ewing's tumors (including Ewing's sarcoma of bone, extraskeletal Ewing's sarcoma, and primitive neuroectodermal tumor), synovial sarcoma, angiosarcomas, hemangiosarcomas, lymphangiosarcomas, Kaposi's sarcoma, hemangioendothelioma, fibrosarcoma, desmoid tumor (also called aggressive fibromatosis), dermatofibrosarcoma protuberans, malignant fibrous histiocytoma, hemangiopericytoma, malignant mesenchymoma, alveolar soft-part sarcoma, epithelioid sarcoma, clear cell sarcoma, desmoplastic small cell tumor, gastrointestinal stromal tumor (also known as GI stromal sarcoma), osteosarcoma (also known as osteogenic sarcoma)-skeletal and extraskeletal, and chondrosarcoma.

The methods of the presently disclosed and claimed inventive concept(s) also include the treatment of subjects with melanoma. Melanomas are tumors arising from the melanocytic system of the skin and other organs. Examples of melanoma include lentigo maligna melanoma, superficial spreading melanoma, nodular melanoma, and acral lentiginous melanoma.

Conditions characterized by an abnormal mammalian cell proliferation as noted are cancers including, but not limited to, biliary tract cancer, endometrial cancer, esophageal cancer, gastric cancer, pancreatic cancer, intraepithelial neoplasms, including Bowen's disease and Paget's disease, liver cancer, oral cancer, including squamous cell carcinoma, sarcomas, including fibrosarcoma and osteosarcoma, skin cancer, including melanoma, Kaposi's sarcoma, testicular cancer, including germinal tumors (seminoma, non-seminoma (teratomas, choriocarcinomas)), stromal tumors and germ cell tumors, thyroid cancer, including thyroid adenocarcinoma and medullar carcinoma, and renal cancer including adenocarcinoma and Wilms tumor.

Further, certain embodiments of the presently disclosed and claimed inventive concept(s) include a method of treating a subject having an abnormal proliferation originating in bone, muscle or connective tissue. Exemplary conditions intended for treatment by the present methods include primary tumors (i.e., sarcomas) of bone and connective tissue. The methods also include treatment of subjects with metastatic tumors, for example metastatic tumors of epithelial origin. Carcinomas may metastasize to bone, as has been observed with breast cancer, and liver, as is sometimes the case with colon cancer. The methods of the presently disclosed and claimed inventive concept(s) are intended to treat metastatic tumors regardless of the site of the metastasis and/or the site of the primary tumor.

The presently disclosed and claimed inventive concept(s) includes methods for inhibiting POP and/or FAP in a subject having a pathology which involves angiogenesis. Angiogenesis is defined as the formation of new blood vessels. These disorders include conditions characterized by abnormal mammalian cell proliferation, such as cancerous conditions wherein overexpression of FAP and/or POP associated with the tumors stimulates angiogenesis and rapid tumor growth, as well as non-cancer conditions including diabetes, diabetic retinopathy, neovascular glaucoma and psoriasis. Thus, in particular embodiments, the present methods are aimed using the disclosed FAP and/or POP inhibitors to inhibit tumor and/or non-tumor angiogenesis. Tumor angiogenesis refers to the formation of new blood vessels in the vicinity or within a tumor mass. Solid tumor cancers require angiogenesis particularly for oxygen and nutrient supply. It has been previously shown that inhibition of angiogenesis in solid tumor can cause tumor regression in animal models. Thus in one aspect, the presently disclosed and claimed inventive concept(s) relates to methods for inhibiting angiogenesis by inhibiting the proliferation, migration or activation of endothelial cells and fibroblasts, wherein this angiogenesis is unrelated to wound healing in response to injury, infection or inflammation.

Thus, the present methods are intended for the treatment of diseases and processes that involve or are mediated by angiogenesis including, but not limited to, hemangioma, solid tumors, tumor metastasis, benign tumors, for example hemangiomas, acoustic neuromas, neurofibromas and trachomas, Osler-Webber Syndrome, telangiectasia, myocardial angiogenesis, angiofibroma, plaque neovascularization, coronary collaterals, ischemic limb angiogenesis, corneal diseases, rubiosis, neovascular glaucoma, diabetic retinopathy, retrolental fibroplasia, diabetic neovascularization, macular degeneration, keloids, ovulation, menstruation, placentation, and any cancer involving angiogenesis.

The compositions and methods of the presently disclosed and claimed inventive concept(s) in certain instances may be useful for replacing existing surgical procedures or drug therapies, although in most instances the methods are useful in improving the efficacy of existing therapies for treating such conditions. Accordingly combination therapy may be used to treat the subjects. For example, the inhibitors may be administered to a subject in combination with another anti-proliferative (e.g., an anti-cancer) therapy. Suitable anti-cancer therapies include, but are not limited to, surgical procedures to remove the tumor mass, chemotherapy or localization radiation. The other anti-proliferative therapy may be administered before, concurrent with, or after treatment with the inhibitors of the presently disclosed and claimed inventive concept(s). There may also be a delay of several hours, days and in some instances weeks between the administration of the different treatments, such that the inhibitor may be administered before or after the other treatment. As an example, the inhibitor may be administered in combination with surgery to remove an abnormal proliferative cell mass. As used herein, "in combination with surgery" means that the agent may be administered prior to, during or after the surgical procedure.

The subjects treated with the presently disclosed FAP and/or POP inhibitors may be treated in combination with other non-surgical anti-proliferative (e.g., anti-cancer) drug therapy. In one embodiment, the inhibitor may be administered in combination with an anti-cancer compound such as a cytostatic compound. A cytostatic compound is a compound (e.g., a nucleic acid, or a protein) that suppresses cell growth and/or proliferation. In some embodiments, the cytostatic compound is directed towards the malignant cells of a tumor. In yet other embodiments, the cytostatic compound is one which inhibits the growth and/or proliferation of vascular smooth muscle cells or fibroblasts.

The presently disclosed and claimed inventive concept(s) in one embodiment is directed to a method of treating cancer comprising administering to a patient in need thereof a cancer treatment comprising radiation and/or an effective amount of a chemotherapeutic composition, and administering at least one compound of the presently disclosed and claimed inventive concept(s), with pharmaceutical acceptable additives, diluents, carriers and excipients, and pharmaceutically acceptable salts thereof.

The presently disclosed and claimed inventive concept(s) also provides the use of compositions which comprise of one or more of the compounds of the presently disclosed and claimed inventive concept(s), their derivatives, metabolites, analogues and/or mimic molecules with pharmaceutical acceptable additives, diluents, carriers and excipients and pharmaceutically acceptable salts thereof, for the manufacture of a medicament for a cancerous condition. As noted elsewhere herein, the pharmaceutical formulations may be administered in combination (before or simultaneously) with other therapeutic treatments, such as radiation treatment or chemotherapeutic drugs.

The presently disclosed and claimed inventive concept(s) is exemplified in terms of in vitro and in vivo activity against various neoplastic cell lines. The test cell lines employed in the in vitro assays are well recognized and accepted as models for anti-tumor activity in animals. The term animals as used herein includes, but is not limited to, mice, rats, domesticated animals such as but is not limited to, cats, dogs, and other animals but is not limited to, cattle, sheep, pigs, horses, and primates such as but not limited to, monkeys, humans and more generally mammals.

In one aspect, certain embodiments of the presently disclosed and claimed inventive concept(s) feature the use of an inhibitory compound of the presently disclosed and claimed inventive concept(s) as a chemosensitizer, in combination with at least one other chemotherapeutic agent or radiation dosage. In a particular embodiment, the compound is co-administered with the chemotherapeutic agent, to a subject. In a particular embodiment, the compound is co-administered with repeated dosages of the same, or a different chemotherapeutic agent, to a subject. In a particular embodiment, the inhibitory compound of the presently disclosed and claimed inventive concept(s) enhances the efficacy of the chemotherapeutic agent, e.g., a cytotoxic agent or radiation dosage, relative to the effect of the cytotoxic agent or radiation dosage in the absence of the compound. The inhibitory compound may be used in combination therapy with conventional cancer chemotherapeutics or treatments. Conventional treatment regimens for tumors include radiation, antitumor agents, interferons, interleukins, tumor necrosis factors, or a combination of two or more of these agents, as well as other chemotherapeutic (cytotoxic) agents described herein.

Suitable anti-proliferative drugs or cytostatic compounds to be used in combination with the presently disclosed and claimed inhibitors include anti-cancer drugs. Numerous anti-cancer drugs which may be used are well known and include, but are not limited to: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Taxotere; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; and Zorubicin Hydrochloride.

Other anti-cancer drugs include, but are not limited to: 20-epi-1,25 dihydroxyvitamin D3; 5-ethynyluracil; abiraterone; acylfulvene; adecypenol; adozelesin; ALL-TK antagonists; ambamustine; amidox; amifostine; aminolevulinic acid; amrubicin; anagrelide; andrographolide; angiogenesis inhibitors; antagonist D; antagonist G; antarelix; anti-dorsalizing morphogenetic protein-1; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bisaziridinylspermine; bisnafide; bistratene A; breflate; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; casein kinase inhibitors (ICOS); castanospermine; cecropin B; cetrorelix; chlorins; chloroquinoxaline sulfonamide; cicaprost; cis-porphyrin; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; dehydrodidemnin B; deslorelin; dexifosfamide; dexrazoxane; dexverapamil; didemnin B; didox; diethylnorspermine; dihydro-5-azacytidine; dihydrotaxol, 9-; dioxamycin; diphenyl spiromustine; docosanol; dolasetron; doxifluridine; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; filgrastim; finasteride; flavopiridol; flezelastine; fluasterone; fludarabine; fluorodaunorunicin hydrochloride; forfenimex; formestane; fotemustine; gadolinium texaphyrin; gallium nitrate; galocitabine; ganirelix; gelatinase inhibitors; glutathione inhibitors; hepsulfam; heregulin; hexamethylene bisacetamide; hypericin; ibandronic acid; idoxifene; idramantone; ilmofosine; ilomastat; imidazoacridones; imiquimod; immunostimulant peptides; insulin-like growth factor-I receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anti cancer compound; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; saintopin; SarCNU; sarcophytol A; sargramostim; Sdi 1 mimetics; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temozolomide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; titanocene dichloride; topsentin; toremifene; totipotent stem cell factor; translation inhibitors; tretinoin; triacetyluridine; triciribine; tropisetron; turosteride; tyrosine kinase inhibitors; tyrphostins; UBC inhibitors; ubenimex; urogenital sinus-derived growth inhibitory factor; urokinase receptor antagonists; variolin B; vector system, erythrocyte gene therapy; velaresol; veramine; verdins; vinorelbine; vinxaltine; vitaxin; zanoterone; zilascorb; and zinostatin stimalamer.

Anti-cancer supplementary potentiating compounds include, but are not limited to: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{2+}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and multiple drug resistance reducing compounds such as Cremaphor EL.

Other compounds which are useful in combination therapy for the purposes of the presently disclosed and claimed inventive concept(s) include, but are not limited to, the antiproliferation compound Piritrexim Isethionate; the antiprostatic hypertrophy compound Sitogluside; the benign prostatic hyperplasia therapy compound Tamsulosin Hydrochloride; the prostate growth inhibitor Pentomone; radioactive compounds such as Fibrinogen I 125, Fludeoxyglucose F 18, Fluorodopa F 18, Insulin I 125, Insulin I 131, Iobenguane I 123, Iodipamide Sodium I 131, Iodoantipyrine I 131, Iodocholesterol I 131, Iodohippurate Sodium I 123, Iodohippurate Sodium I 125, Iodohippurate Sodium I 131, Iodopyracet I 125, Iodopyracet I 131, Iofetamine Hydrochloride I 123, Iomethin I 125, Iomethin I 131, Iothalamate Sodium I 125, Iothalamate Sodium I 131, Iotyrosine I 131, Liothyronine I 125, Liothyronine I 131, Merisoprol Acetate Hg 197, Merisoprol Acetate Hg 203, Merisoprol Hg 197, Selenomethionine Se 75, Technetium Tc 99m Antimony Trisulfide Colloid, Technetium Tc 99m Bicisate, Technetium Tc 99m Disofenin, Technetium Tc 99m Etidronate, Technetium Tc 99m Exametazime, Technetium Tc 99m Furifosmin, Technetium Tc 99m Gluceptate, Technetium Tc 99m Lidofenin, Technetium Tc 99m Mebrofenin, Technetium Tc 99m Medronate, Technetium Tc 99m Medronate Disodium, Technetium Tc 99m Mertiatide, Technetium Tc 99m Oxidronate, Technetium Tc 99m Pentetate, Technetium Tc 99m Pentetate Calcium Trisodium, Technetium Tc 99m Sestamibi, Technetium Tc 99m Siboroxime, Technetium Tc 99m Succimer, Technetium Tc 99m Sulfur Colloid, Technetium Tc 99m Teboroxime, Technetium Tc 99m Tetrofosmin, Technetium Tc 99m Tiatide, Thyroxine I 125, Thyroxine I 131, Tolpovidone I 131, Triolein I 125 and Triolein I 131.

According to the methods of the presently disclosed and claimed inventive concept(s), the inhibitors of FAP and/or POP may be administered prior to, concurrent with, or following the other anti-cancer compounds described herein (or others not listed). The administration schedule may involve administering the different agents in an alternating fashion. In other embodiments, the inhibitor may be delivered before and during, or during and after, or before and after treatment with other therapies. In some cases, the inhibitor is administered more than 24 hours before the administration of the other anti-proliferative treatment. In other embodiments, more than one anti-proliferative therapy may be administered to a subject. For example, the subject may receive the present inhibitors, in combination with both surgery and at least one other anti-proliferative compound. Alternatively, the inhibitor may be administered in combination with more than one anti-cancer drug.

Other compounds useful in combination therapies with the inhibitor compounds of the presently disclosed and claimed inventive concept(s) include, but are not limited to, anti-angiogenic compounds such as angiostatin, endostatin, fumagillin, non-glucocorticoid steroids and heparin or heparin fragments and antibodies to one or more angiogenic peptides such as α-FGF, β-FGF, VEGF, IL-8 and GM-CSF. These latter anti-angiogenic compounds may be administered along with the inhibitor compounds of the presently disclosed and claimed inventive concept(s) for the purpose of inhibiting proliferation or inhibiting angiogenesis in all of the aforementioned conditions as described herein. In certain embodiments, the inhibitors may be administered in combination with an anti-angiogenic compound and at least one of the anti-proliferative therapies described above including surgery or anti-proliferative drug therapy.

In yet other examples, the inhibitors according to the presently disclosed and claimed inventive concept(s) can be used to treat CNS maladies such as strokes, tumors, ischemia, Parkinson's disease, memory deficits, memory loss, eating disorders, senile dementia, hearing loss, vision loss, migraines, depression, brain injury, bipolar disorder, spinal cord injury, Alzheimer's disease, and amyotrophic lateral sclerosis (which has a CNS component) and can be used to improve learning and memory function.

The inhibitor compounds of the presently disclosed and claimed inventive concept(s) are administered in therapeutically effective amounts. An effective amount is a dosage of the inhibitor sufficient to provide a therapeutically or medically desirable result or effect in the subject to which the compound is administered. The effective amount will vary with the particular condition being treated, the age and physical condition of the subject being treated, the severity of the condition, the duration of the treatment, the nature of the concurrent or combination therapy (if any), the specific route of administration and like factors within the knowledge and expertise of the health practitioner. For example, in connection with methods directed towards treating subjects having a condition characterized by abnormal cell proliferation, an effective amount to inhibit proliferation would be an amount sufficient to reduce or halt altogether the abnormal cell proliferation so as to slow or halt the development of or the progression of a cell mass such as, for example, a tumor. As used in the embodiments, "inhibit" embraces all of the foregoing. In other embodiments, a therapeutically effective amount will be an amount necessary to extend the dormancy of micrometastases or to stabilize any residual primary tumor cells following surgical or drug therapy.

Generally, a therapeutically effective amount will vary with the subject's age, condition, and sex, as well as the nature and extent of the disease in the subject, all of which can be determined by one of ordinary skill in the art. The dosage may be adjusted by the individual physician or veterinarian, particularly in the event of any complication. A therapeutically effective amount is typically, but not limited to, an amount in a range from 0.1 µg/kg to about 2000 mg/kg, or from 1.0 µg/kg to about 1000 mg/kg, or from about 0.1 mg/kg to about 500 mg/kg, or from about 1.0 mg/kg to about 100 mg/kg, in one or more dose administrations daily, for one or more days. If desired, the effective daily dose of the active compound may be administered as two, three, four, five, six or more sub-doses for example administered separately at appropriate intervals throughout the day, optionally, in unit dosage forms. In some embodiments, the inhibitors are administered for more than 7 days, more than 10 days, more than 14 days and more than 20 days. In still other embodiments, the inhibitor is administered over a period of weeks, or months. In still other embodiments, the inhibitor is delivered on alternate days. For example, the agent is delivered every two days, or every three days, or every four days, or every five days, or every six days, or every week, or every month.

The inhibitor compounds of the presently disclosed and claimed inventive concept(s) can also be administered in prophylactically effective amounts, particularly in subjects diagnosed with benign or pre-malignant tumors or conditions likely to present pathogenic angiogenesis, such as diabetes. In these instances, the inhibitors are administered in an amount effective to prevent the development of an abnormal mammalian cell proliferative mass or to prevent angiogenesis in the solid tumor mass, depending on the embodiment. The inhibitors may also be administered in an amount effective to prevent metastasis of cells from a tumor to other tissues in the body. In these latter embodiments, the presently disclosed and claimed inventive concept(s) includes methods of preventing the metastatic spread of a primary tumor or angiogenesis related to pathogenic conditions.

According to another aspect of the presently disclosed and claimed inventive concept(s), a kit is provided. The kit is a package which houses a container which contains an inhibitor of the presently disclosed and claimed inventive concept(s) and also includes instructions for administering the inhibitor to a subject having a condition characterized by an abnormal mammalian cell proliferation or other condition described herein. The kit may optionally also contain one or more other anti-proliferative compounds or one or more anti-angiogenic compounds for use in combination therapies as described herein.

The compounds of the presently disclosed and claimed inventive concept(s) may be administered alone or in combination with the above-described drug therapies by a variety of administration routes available. The particular mode selected will depend, of course, upon the compound selected, the condition being treated, the severity of the condition, whether the treatment is therapeutic or prophylactic, and the dosage required for efficacy. The methods of the presently disclosed and claimed inventive concept(s), generally speaking, may be practiced using any mode of administration that is medically acceptable, meaning any mode that produces effective levels of the active compounds without causing clinically unacceptable adverse effects. The administration may, for example, be oral, intraperitoneal, intra-cavity such as rectal or vaginal, transdermal, topical, nasal, inhalation, mucosal, interdermal, or parenteral routes. The term "parenteral" includes subcutaneous, intravenous, intramuscular, or infusion. Intravenous or intramuscular routes may not particularly suitable for long term therapy and prophylaxis. In certain embodiments, however, it may be appropriate to administer the compound in a continuous infusion every several days, or once a week, or every several weeks, or once a month. Intravenous or intramuscular routes may be desired in emergency situations. Oral administration may be used for prophylactic treatment because of the convenience to the patient as well as the dosing schedule. Likewise, sustained release devices as described herein may be useful in certain embodiments for prophylactic or post surgery treatment, for example.

When using the compounds of the presently disclosed and claimed inventive concept(s) in subjects in whom the primary site of abnormal proliferation is well delineated and easily accessible, direct administration to the site may be desired, provided the tumor has not already metastasized. For example, administration by inhalation for lung tumors or by suppositories in the treatment of cervical, ovarian or rectal tumors may be desired. Likewise, melanoma, for example, may be treated with the compound via topical administration in and around the area of the lesion. In still other embodiments aimed at the treatment of subjects with breast, lung, pancreatic, or prostate cancer, for example, the compounds may be delivered by injection directly into the tissue with, for example, a biopsy needle and syringe.

Systemic administration may be desired in some instances such as, for example, if the subject is known to have or is suspected of having metastases. In this way, all tumor sites, whether primary or secondary, may receive the compound. Systemic delivery may be accomplished through for example, oral or parenteral administration. Inhalation may be used in either systemic or local delivery, as described herein.

Compositions of the compound for parenteral administration particularly include, but are not limited to, sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include, for example, sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating compounds, and inert gases and the like. The pharmaceutical compositions may conveniently be presented in unit dosage form and may be prepared by any of the methods well-known in the art of pharmacy.

Compositions suitable for oral administration may particularly comprise discrete units, such as capsules, tablets, lozenges, each containing a predetermined amount of the inhibitor. Other compositions include suspensions in aqueous liquids or non-aqueous liquids such as a syrup, elixir, or an emulsion. In yet other embodiments, the particular vehicle is a biocompatible microparticle or implant that is suitable for implantation into the mammalian recipient.

In other embodiments of the methods and compounds of the presently disclosed and claimed inventive concept(s), the compound is targeted to a site of abnormal cell proliferation, such as, a tumor, through the use of a targeting compound specific for a particular tissue or tumor type. The compounds of the presently disclosed and claimed inventive concept(s) may be targeted to primary or in some instances, secondary (i.e., metastatic) lesions through the use of targeting compounds which preferentially recognize a cell surface marker. The targeting compound may be directly conjugated to the compounds of the presently disclosed and claimed inventive concept(s) via a covalent linkage. The compound may be indirectly conjugated to a targeting compound via a linker. Alternatively, the targeting compound may be conjugated or associated with an intermediary compound such as, for example, a liposome within which the inhibitor is encapsulated. Liposomes are artificial membrane vessels which are useful as a delivery vector in vivo or in vitro. It has been shown that large unilamellar vessels (LUV), which range in size from 0.2-4.0 µm can encapsulate large macromolecules. Liposomes may be targeted to a particular tissue, such as the vascular cell wall, by coupling the liposome to a specific ligand such as a monoclonal antibody, sugar, glycolipid, or protein. In still other embodiments, the targeting compound may be loosely associated with the compounds of the presently disclosed and claimed inventive concept(s), such as within a microparticle comprising a polymer, the compound of the presently disclosed and claimed inventive concept(s) and the targeting compound.

Targeting compounds useful according to the methods of the presently disclosed and claimed inventive concept(s) are those which direct the compound to a site of abnormal proliferation such as a tumor site. The targeting compound of choice will depend upon the nature of the tumor or the tissue origin of the metastasis. In some instances it may be desirable to target the compound to the tissue in which the tumor is located. For example, the compounds can be delivered to breast epithelium by using a targeting compound specific for breast tissue. In particular embodiments, the target is specific for malignant breast epithelium. Examples of compounds which may localize to malignant breast epithelium include, but are not limited to, estrogen and progesterone, epithelial growth factor (EGF) and HER-2/neu ligand, among others. The HER-2/neu ligand may also be used to target compounds to ovarian cancers. Ovarian cancers are also known to express EGFR and c-fms, and thus could be targeted through the use of ligands for either receptor. In the case of c-fms which is also expressed by macrophages and monocytes, targeted delivery to an ovarian cancer may require a combination of local administration such as a vaginal suppository as well as a targeting compound. Prostate cancers can be targeted using compounds such as peptides (e.g., antibodies or antibody fragments) which bind to prostate specific antigen (PSA) or prostate specific membrane antigen (PSMA). Other markers which may be used for targeting of the agent to specific tissues include, for example, in liver: HGF, insulin-like growth factor I, II, insulin, OV-6, HEA-125, hyaluronic acid, collagen, N-terminal propeptide of collagen type III, mannose/N-acetylglucosamine, asialoglycoprotein, tissue plasminogen activator, low density lipoprotein, carcinoembryonic antigen; in kidney cells: angiotensin II, vasopressin, antibodies to CD44v6; in keratinocytes and skin fibroblasts: KGF, very low density lipoprotein, RGD-containing peptides, collagen, laminin; in melanocytes: kit ligand; in gut: cobalamin-intrinsic factor, heat stable enterotoxin of E. Coli; in breast epithelium: heregulin, prolactin, transferrin, cadherin-11. Other markers specific to particular tissues are available and would be known to one of ordinary skill in the art.

In still other embodiments, the compounds of the presently disclosed and claimed inventive concept(s) may be targeted to fibroblasts specifically, via ligands or binding partners for fibroblast specific markers. Examples of these markers include, but are not limited to fibroblast growth factors (FGF) and platelet derived growth factor (PDGF). In some embodiments, it is desirable to target the compound to FAP specifically through the use of binding peptides for FAP which do not interfere with inhibition by the compound of the presently disclosed and claimed inventive concept(s).

Other embodiments of the presently disclosed and claimed inventive concept(s) include pharmaceutically acceptable compositions which comprise a therapeutically-effective amount of one or more of the compounds described herein, formulated together with one or more pharmaceutically acceptable carriers (additives) and/or diluents. As described in detail below, the pharmaceutically acceptable compositions may be specially formulated for administration in solid or liquid form, including, but not limited to, those adapted for the following: (1) oral administration, for example, aqueous or non-aqueous solutions or suspensions, tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a cream or foam; (5) sublingually; (6) ocularly; (7) transdermally; or (8) nasally.

Some examples of materials which can serve as pharmaceutically-acceptable carriers include, but are not limited to: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set forth above, in certain embodiments, the compounds of the presently disclosed and claimed inventive concept(s) contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of the compounds. These salts can be prepared in situ in the administration vehicle or the dosage form manufacturing process, or by separately reacting a purified compound of the presently disclosed and claimed inventive concept(s) in its free base form with a suitable organic or inorganic acid, and isolating the salt thus formed during subsequent purification. Representative salts include, but are not limited to, the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

The pharmaceutically acceptable salts of the compounds of the presently disclosed and claimed inventive concept(s) include, but are not limited to, the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the presently disclosed and claimed inventive concept(s) may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the presently disclosed and claimed inventive concept(s). These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include, but are not limited to, the lithium, sodium, potassium, calcium, magnesium, and aluminum salts and the like. Representative organic amines useful for the formation of base addition salts include, but are not limited to, ethylamine, diethylamine, ethylenediamine, ethanolamine, diethanolamine, piperazine and the like.

Wetting agents, emulsifiers and lubricants, including, but not limited to, sodium lauryl sulfate and magnesium stearate, as well as coloring agents, release agents, coating agents, sweetening, flavoring and perfuming agents, preservatives and antioxidants can also be present in the compositions. Examples of pharmaceutically-acceptable antioxidants include, but are not limited to: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

As noted above, formulations of the compounds of the presently disclosed and claimed inventive concept(s) include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, such as from about 5 percent to about 70 percent, or from about 10 percent to about 30 percent.

In certain embodiments, a formulation of the compounds of the presently disclosed and claimed inventive concept(s) comprises an excipient selected from the group consisting of cyclodextrins, liposomes, micelle forming agents, e.g., bile acids, and polymeric carriers, e.g., polyesters and polyanhydrides.

Methods of preparing these formulations or compositions may include the step of bringing into association a compound of the presently disclosed and claimed inventive concept(s) with the carrier and, optionally, one or more accessory ingredients. In general, the formulations are prepared by uniformly and intimately bringing into association a compound of the presently disclosed and claimed inventive concept(s) with liquid carriers, or finely divided solid carriers, or both, and then, if necessary, shaping the product.

Formulations of the compounds of the presently disclosed and claimed inventive concept(s) suitable for oral administration may be, but are not limited to, the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the presently disclosed and claimed inventive concept(s) as an active ingredient. A compound of the presently disclosed and claimed inventive concept(s) may also be administered as a bolus, or paste.

In solid dosage forms of the compounds of the presently disclosed inventive concept(s) for oral administration (capsules, tablets, pills, powders, granules and the like), the compound or compounds are mixed with one or more pharmaceutically-acceptable carriers, including, but not limited to, sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the presently disclosed and claimed inventive concept(s), such as dragees, capsules, pills and granules, may optionally be scored or prepared with coatings and shells, such as enteric coatings and other coatings well known in the pharmaceutical-formulating art. They may also be formulated so as to provide slow or controlled release of the compound or compounds therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the presently disclosed and claimed inventive concept(s) include, but are not limited to, pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents. Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the compounds of the pharmaceutical compositions of the presently disclosed and claimed inventive concept(s) for rectal or vaginal administration may be presented as a suppository, which may be prepared by mixing one or more compounds of the presently disclosed and claimed inventive concept(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the presently disclosed and claimed inventive concept(s) which are suitable for vaginal administration also include, but are not limited to, tampons, creams, gels, pastes, foams or spray formulations containing such carriers as are known in the art to be appropriate. Dosage forms for the topical or transdermal administration of a compound of the presently disclosed and claimed inventive concept(s) include, but are not limited to, powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required. The ointments, pastes, creams and gels may contain, for example, in addition to an active compound of the presently disclosed and claimed inventive concept(s), excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, for example, in addition to a compound of the presently disclosed and claimed inventive concept(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the presently disclosed and claimed inventive concept(s) to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel. Ophthalmic formulations, eye ointments, powders, solutions and the like, are also contemplated as being within the scope of the presently disclosed and claimed inventive concept(s).

Pharmaceutical compositions of the compounds of the presently disclosed and claimed inventive concept(s) suitable for parenteral administration comprise one or more compounds of the presently disclosed and claimed inventive concept(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the presently disclosed and claimed inventive concept(s) include, but are not limited to, water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the presently disclosed and claimed inventive concept(s) are administered as pharmaceuticals, to human or animal subjects, they are generally given as a pharmaceutical composition containing, for example, 0.01% to 99.5% (such as 0.5 to 90%) of the compound (with or without other compounds given adjunctively in combination with a pharmaceutically acceptable carrier).

The preparations of the presently disclosed and claimed inventive concept(s) may be given, for example, orally, parenterally, topically, or rectally as explained above. They are of course given in forms suitable for each administration route. For example, they are administered in tablets or capsule form, by injection, inhalation, eye lotion, ointment, suppository, by injection, infusion or inhalation, topical by lotion or ointment, and rectal by suppositories. The phrases "parenteral administration" and "administered parenterally" as used herein means modes of administration other than enteral and topical administration, usually by injection, and includes, but is not limited to, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion. The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

Regardless of the route of administration selected, the compounds of the presently disclosed and claimed inventive concept(s), which may be used in a suitable hydrated form, and/or the pharmaceutical compositions of the presently disclosed and claimed inventive concept(s), are formulated into pharmaceutically-acceptable dosage forms by conventional methods known to those of skill in the art. Actual dosage levels of the active ingredients in the pharmaceutical compositions of the presently disclosed and claimed inventive concept(s) may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the presently disclosed and claimed inventive concept(s) employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the presently disclosed and claimed inventive concept(s) employed in the pharmaceutical composition at levels lower than that required in order to achieve the desired therapeutic effect and gradually increase the dosage until the desired effect is achieved. While it is possible for compounds of the presently disclosed and claimed inventive concept(s) to be administered alone, it may be desired to administer the compound as a pharmaceutical formulation (composition).

As noted, particular amounts and modes of administration are able to be determined by one skilled in the art. One skilled in the art of preparing formulations can readily select the proper form and mode of administration depending upon the particular characteristics of the compound selected, the disease state to be treated, the stage of the disease, and other relevant circumstances using formulation technology known in the art, described, for example, in *Remington's Pharmaceutical Sciences*, latest edition, Mack Publishing Co.

Pharmaceutical compositions can be manufactured utilizing techniques known in the art. Typically the therapeutically effective amount of the compound will be admixed with a pharmaceutically acceptable carrier as described elsewhere herein. In one embodiment, the half-life of the compounds described herein can be extended by their being conjugated to other molecules such as polymers using methods known in the art to form drug-polymer conjugates. For example, the molecules can be bound to molecules of inert polymers known in the art, such as a molecule of polyethylene glycol (PEG) in a method known as "PEGylation". Pegylation can therefore extend the in vivo lifetime and thus therapeutic effectiveness of the molecule.

PEG molecules can be modified by functional groups, for example as shown in Harris et al., "Pegylation, A Novel Process for Modifying Phararmacokinetics", *Clin Pharmacokinet,* 2001:40(7); 539-551, and the amino terminal end of the molecule, or cysteine residue if present, or other linking amino acid therein can be linked thereto, wherein the PEG molecule can carry one or a plurality of one or more types of molecules.

By "polyethylene glycol" or "PEG" is meant a polyalkylene glycol compound or a derivative thereof, with or without coupling agents or derviatization with coupling or activating moeities (e.g., with thiol, triflate, tresylate, azirdine, oxirane, or particularly with a maleimide moiety). Compounds such as maleimido monomethoxy PEG are exemplary or activated PEG compounds of the inventive concept(s). Other polyalkylene glycol compounds, such as polypropylene glycol, may be used in the presently disclosed and claimed inventive concept(s). Other appropriate polymer conjugates include, but are not limited to, non-polypeptide polymers, charged or neutral polymers of the following types: dextran, colominic acids or other carbohydrate based polymers, biotin deriviatives and dendrimers, for example. The term PEG is also meant to include other polymers of the class polyalkylene oxides.

The PEG can be linked to any N-terminal amino acid of the molecule described herein and/or can be linked to an amino acid residue downstream of the N-terminal amino acid, such as lysine, histidine, tryptophan, aspartic acid, glutamic acid, and cysteine, for example or other such amino acids known to those of skill in the art. The PEG carrier moiety attached to the peptide may range in molecular weight from about 200 to 20,000 MW. Particularly, the PEG moiety may be from about 1,000 to 8,000 MW, such as from about 3,250 to 5,000 MW, or about 5,000 MW. The actual number of PEG molecules covalently bound per molecule of the inventive concept(s) may vary widely depending upon the desired stability (i.e. serum half-life). Molecules contemplated herein can be linked to PEG molecules using techniques shown, for example (but not limited to), in U.S. Pat. Nos. 4,179,337; 5,382,657; 5,972,885; 6,177,087; 6,165,509; 5,766,897; and 6,217,869; the specifications and drawings each of which are hereby expressly incorporated herein by reference.

Alternatively, it is possible to entrap the molecules in microcapsules prepared, for example, by coacervation techniques or by interfacial polymerization (for example, hydroxymethylcellulose or gelatine-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are disclosed in the latest edition of *Remington's Pharmaceutical Sciences*.

U.S. Pat. No. 4,789,734 describes methods for encapsulating biochemicals in liposomes and is hereby expressly incorporated by reference herein. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", *Drug Carriers in Biology and Medicine*, pp. 287-341 (Academic Press, 1979). Microspheres formed of polymers or proteins are well known to those skilled in the art, and can be tailored for passage through the gastrointestinal tract directly into the blood stream. Alternatively, the agents can be incorporated and the microspheres, or composite of microspheres, implanted for slow release over a period of time, ranging from days to months. See, for example, U.S. Pat. Nos. 4,906,474; 4,925,673; and 3,625,214 which are incorporated by reference herein.

When the composition of the presently disclosed and claimed inventive concept(s) is to be used as an injectable material, it can be formulated into a conventional injectable carrier. Suitable carriers include biocompatible and pharmaceutically acceptable phosphate buffered saline solutions, which may be isotonic.

For reconstitution of a lyophilized product in accordance with the presently disclosed and claimed inventive concept(s), one may employ a sterile diluent, which may contain materials generally recognized for approximating physiological conditions and/or as required by governmental regulation. In this respect, the sterile diluent may contain a buffering agent to obtain a physiologically acceptable pH, such as sodium chloride, saline, phosphate-buffered saline, and/or other substances which are physiologically acceptable and/or safe for use. In general, the material for intravenous injection in humans should conform to regulations established by the Food and Drug Administration, which are available to those in the field. The pharmaceutical composition may also be in the form of an aqueous solution containing many of the same substances as described above for the reconstitution of a lyophilized product.

The compounds of the presently disclosed and claimed inventive concept(s) can also be administered as a pharmaceutically acceptable acid- or base-addition salt, formed by reaction with inorganic acids such as, but not limited to, hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

EXAMPLES

While the presently disclosed and claimed inventive concept(s) will now be described in connection with certain embodiments in the following examples so that aspects thereof may be more fully understood and appreciated, it is not intended to limit the inventive concept(s) to these particular examples. On the contrary, it is intended to cover all alternatives, modifications and equivalents as may be included within the scope of the presently disclosed and claimed inventive concept(s) as defined herein and in the appended claims. Thus, the following examples, which include particular embodiments will serve to illustrate the practice of the presently disclosed and claimed inventive concept(s), it being understood that the particulars shown are by way of example and for purposes of illustrative discussion of particular embodiments of the presently disclosed and claimed inventive concept(s) only and are presented in the cause of providing what is believed to be the most useful and readily understood description of compounds, methods of use, and formulation procedures as well as of the principles and conceptual aspects of the presently disclosed and claimed inventive concept(s).

EXPERIMENTAL

The following describes various experimental procedures used to synthesize examples of substrates and inhibitors and further experimentation based on these substrates and inhibitors.

Materials and Methods

Cell Culture:

Fibroblasts, WI-38 and WI-38 VA13 2RA (VA-13); breast cancer cells, MDA-MB436 (MDA) and HCC1419 (HCC); and normal breast cells, MCF-12A, were all purchased from American Type Culture Collection (ATCC). Human dermal microvascular endothelial cells (HMVEC-d) and mesenchymal stem cells (MSC) were purchased from Lonza. All cells were authenticated by the companies and used within six months of purchase or recovery from cryopreservation. WI-38 and VA-13 were grown in MEM (Mediatech Inc.) supplemented with 10% FCS (fetal calf serum, Gibco), 2 mM GlutaMAX-1 (Gibco) and 1 mM sodium pyruvate (Gibco). MDA and HCC were grown in DMEM (Mediatech Inc.) supplemented with 10% FCS. MCF-12A and HMVEC-d were grown in EGM2-MV (Lonza) with all provided supplements, unless otherwise specified. MSC were grown in MSCGM (Lonza).

Monoclonal Antibody Production:

Human antiplasmin-cleaving enzyme (APCE) was purified as previously described [28] and used as the antigen for monoclonal antibody (mAb) production. The hybridoma cells were produced at the Hybridoma Center for Agricultural and Biological Sciences at Oklahoma State University. After initial screening against pure APCE by direct ELISA, the positive cells were cloned three times by limited dilution. Selected antibodies were produced in serum free media (SFM, Gibco) in roller bottles, then purified using MEP Hypercel (Pall) chromatography and isotyped using the Pierce Rapid Isotyping kit (Thermo Scientific). Out of 24 mAbs identified, mAb 6D2, an IgG1κ antibody, which recognized both APCE and FAP by ELISA and Western blotting with the greatest sensitivity, was used in these studies. Mouse F19 mAb to FAP was produced and purified from cultures of hybridoma cells purchased from ATCC, and used for confocal imaging and immunoprecipitation (IP).

Immunostaining:

Selected normal or neoplastic cells were grown to confluency in 10 cm tissue culture dishes, rinsed in phosphate buffered saline (PBS) and lysed on the plate in 1 ml of 2× Laemmli denaturing sample buffer with DTT for whole cell lysate. Membrane and cytosolic fractions were prepared from confluent tissue culture dishes using the Mem-PER kit (Pierce) per manufacturer instructions. Whole cell lysates were electrophoresed under reducing conditions on 4-12% Bis-tris SDS-PAGE gels (Invitrogen) and transferred to nitrocellulose for Western blotting. After blocking with 3% bovine serum albumin (BSA)/TBS-Tween (TBST), blots were incubated with a combination of 0.5 µg/ml mAb 6D2, 0.1 µg/ml anti-α tubulin (Sigma #6199) and 0.1 µg/ml anti-actin (Abcam 2Q1055) all in 1% BSA/TBST, and then washed and incubated with 1:50,000 goat anti-mouse-HRP (Thermo-Fisher). Blots for POP were blocked with 3% BSA/TBST, then incubated with a combination of 0.1 µg/ml goat anti-POP (R & D Systems #AF4308), 0.1 µg/ml anti-α tubulin (Sigma #6199) and 0.1 µg/ml anti-actin (Abcam 2Q1055) in 1.5% BSA/0.5M NaCl/TBST. After washing in the same buffer, blots were incubated with 1:18,000 rabbit anti-goat-HRP (R & D Systems #HAF017) in 1.5% BSA/0.5M NaCl/TBST. ECL-Plus (Thermo-Fisher) was added and blots were visualized on RPI blue radiographic film (Amersham).

Confocal analysis of FAP protein in cells was accomplished first by growing cells to confluence on four-well glass chamber slides (Lab-Tek). The cells were fixed with 0.75% paraformaldehyde, blocked with 1% BSA/PBS, and then incubated with mouse F19 mAb 2 µg/ml or isotype control antibody, MOPC 21(Sigma), 2 µg/ml in 0.1% BSA/PBS, with 0.1% saponin. After washing, the slides were incubated with goat anti-mouse-Alexa Fluor 568 (Invitrogen) at 1:2000 in 0.1% BSA/PBS and then mounted in Prolong Gold/DAPI (Molecular Probes). Cells were visualized using a Leica TCS NT Microscope fitted with a 40× Plan Fluotar 1.0 NA oil immersion objective. Images were analyzed using Leica TCS and Volocity software.

Protein Characterization:

Cells of each type were grown to confluence in 10 cm tissue culture dishes, rinsed in PBS and then lysed in 1 ml ice-cold IP buffer containing 1% Triton/150 mM NaCl/10 mM Tris, pH 7.5/1 mM EDTA/1 mM EGTA/0.5% NP-40/ 10% sucrose with Complete Ultra protease inhibitor cocktail (Roche) added. Whole cell lysates were centrifuged to remove detergent-insoluble proteins. Five µg/ml of mAb F19 were added and allowed to bind overnight at 4° C. Then 25 µl of 75% slurry of Protein G beads (Amersham) in TBS were added and incubated for 1 hour at 4° C. Protein G beads were spun down, washed three times with IP buffer, resuspended in loading buffer and boiled for five minutes, after which the beads were removed by centrifugation and a portion of the supernatant was electrophoresed under reducing conditions on 4-12% Bis-tris SDS-PAGE gels. To confirm the presence of FAP, the regions of each lane corresponding to the molecular weight of FAP were excised and the proteins within each gel slice were reduced with Tris[2-carboxyethyl]phosphine, then alkylated with iodoacetamide, and digested with trypsin as described by the In-gel Tryptic Digestion Kit protocol (Thermo-Fisher). Each trypsin digest sample was analyzed by high performance liquid chromatography-tandem mass spectrometry (LC/MS/MS) on a nanoscale Dionex UltiMate 3000 HPLC equipped with an Acclaim PepMap C18 column (75 µm internal diameter×15 cm length with 3 µm particles) connected to an AB-Sciex QSTAR Elite mass spectrometer. The peptide molecular weights and MS/MS fragment ion spectra observed for each peptide were used to query an NCBI comprehensive nonidentical human protein database (updated Jan. 31, 2011) loaded on an in-house MASCOT database server (version 2.3).

Inhibitors and Substrates:

The pseudo-peptide inhibitor, M83 (acetyl-Arg-AEEA-(D)Ala-(L)boroPro), has dual FAP ($K_i$=5.7 nM) and POP ($K_i$=7.4 nM) inhibition. The specific POP inhibitor, J94 (acetyl-Lys-Leu-Arg-(L)boroPro ($K_i$<100 nM)); and the substrate, C95 (acetyl-Arg-AEEA-Gly-Pro-AMC), were designed, synthesized and characterized by us as previously reported [27]. All are soluble in aqueous buffers. The inhibitors (J94 and M83) were dissolved in Hanks Balanced Salt Solution (HBSS; Gibco) at 1 mM and stored at −20° C. The substrate (C95) was dissolved in HBSS at 2.5 mM and stored at 4° C. FAP and POP at equimolar concentrations cleaved C95 substrate at equivalent rates (data not shown). Tic-Pro-AFC, a prolyl-specific fluorescent substrate, was supplied by Vantia (Southampton, England).

APCE (~4 µg), DPPIV (~2 µg) or POP (~2 µg) was incubated in 25 mM sodium phosphate buffer, pH 7.5, containing 1.0 mM EDTA and 2% methanol in a total volume of 200 µl for 20 min at 22° C. Using Tic-Pro-AFC (10-300 µM for APCE, 5-200 µM for DPPIV, and 40-800 µM for POP), fluorescence was monitored with time at excitation/emission wavelengths of 400/508 nm, using a black-sided 96-well plate in a BIO-TEK FL600 fluorescence plate reader. For accurate assessment of kinetic parameters, saturating concentrations of substrate were used. For standard curves, dilutions of AFC (7-amino-4-trifluoromethylcoumarin) were prepared in the same assay buffer and corresponding fluorescence was measured. The substrate in five different concentrations (20, 40, 60, 80 & 160 µM) was mixed with four different concentrations of inhibitors around the preliminary apparent (app) $K_1$ values.

Whole Cell Activity Assays:

Cells were cultured in normal growth media unless otherwise stated. For cells grown in media with selected components either withheld or added, and depending on each experimental design as indicated in the Results section, growth times were chosen from 7 to 14 days in specific media before plating for activity assays. For activity assays, cells were plated into 96-well black-sided, clear bottom tissue culture plates (Costar) at densities selected for achieving confluency in three days as indicated in the Results section or each such experiment. Cell densities varied with cell type and the selected growth media; the number of cells necessary for plating was estimated from pilot experiments. After three days growth, cultures were washed with HBSS. The wash solution was replaced with 188 µl fresh buffer (HBSS) and either buffer or two µl of M83 or J94 inhibitor (10 µM final) was added. Ten µl of fluorescent substrate, C95 were added to give a final concentration of 125 µM, and fluorescence was measured with time at 360/460 nm excitation/emission wavelengths using an FL600 microplate fluorescence reader (Bio-tek Instruments). Fluorescence units were converted to FAP units/100,000 cells by using a conversion factor determined from an APCE standard curve of prolyl-specific endopeptidase activity, such that 1 FAP unit is equivalent to the fluorescence produced by 1 ng of APCE/min. Since FAP and POP cleave the C95 substrate at an equivalent rate, both FAP and POP activities are expressed as FAP units in all figures.

For tube formation assays, Matrigel™ (BD Biosciences, San Jose, Calif.) 80 µl was added to black-sided, clear bottom 96-well plates as above and allowed to gel at 37° C. for 30 minutes. Then 15,000 HMVEC-d in EC media without serum were added and allowed to settle for 1 hour. Either buffer, the M83 inhibitor or the J94 inhibitor (10 µM final) was added and the assay then started by adding the dual FAP/POP fluorescent C95 substrate. The reader was maintained at 37° C. and fluorescence was measured with time for 18 hours.

Results

FAP/APCE and POP are prolyl-specific serine endopeptidases, with the proteolytic activity of POP generally restricted to peptides having less than about 30 residues [31]. FAP appears to be membrane-inserted and POP membrane-associated [32, 33], while APCE circulates in blood, possibly as a shed soluble derivative or splice-variant of FAP [12]. Non-specific single amino acid and dipeptide prolyl boronic acid compounds or mutations of the serine active-site in FAP inhibit FAP proteolytic activity on cancer associated fibroblasts and diminishes cancer growth [17, 21]. POP, commonly expressed by neoplasms [7, 25, 33-35], manifests overlapping proteolytic activity with FAP/APCE when measured as usual with non-specific fluorescent peptide substrates such as Z-Gly-Pro-AMC or succinyl-Gly-Pro-AMC [27]. Efforts to use inhibitors to separate the two enzymatic activities have likewise been compromised by significant inhibition of both FAP and POP [27]. The problem of measuring FAP and POP activities separately in biologic or pathologic scenarios where either may play a critical role, had received scant attention prior to the present work.

Characterization of Tic-Pro-AFC as substrate: A new substrate, Tic-Pro-AFC, was used for assessing APCE/FAP, DPPIV and POP, each belonging to the same Glade of prolyl-specific serine proteinases and each with activity towards unique substrates. The typical synthetic substrate for APCE/FAP or POP is benzyloxycarbonyl (Z)-GP-AMC for which each enzyme exhibits a catalytic efficiency ($k_{cat}/K_m$) of $6.7\times10^3$ and $9.5\times10^5$ $M^{-1}$ $s^{-1}$, respectively. Z-GP-AMC is not cleaved by DPPIV; however, the latter does cleave GP-AMC ($k_{cat}/K_m=3.2\times10^4$ $M^{-1}$ $s^{-1}$). GP-AMC is a poor substrate for APCE/FAP ($k_{cat}/K_m=1.1\times10^3$ $M^{-1}$ $s^{-1}$) and is not cleaved by POP. Based on $K_i$, $K_m$ and $k_{cat}$ values in Tables 6 and 7, Tic-Pro-AFC was readily cleaved by each enzyme, with $k_{cat}/K_m$ for APCE/FAP being slightly higher than POP and slightly lower than DPPIV. Importantly, $k_{cat}/K_m$ values were in keeping with those determined using Gly-Pro-AMC or Z-Gly-Pro-AMC as substrates; however, Tic-Pro-AFC proved more sensitive and gave more reproducible results. Thus, Tic-Pro-AFC was chosen as the substrate for comparing the potency and selectivity of the inhibitors towards APCE/FAP, DPPIV, or POP.

In FIG. 1A, confocal microscopy of immunostained saponin-permeabilized WI-38 fibroblasts shows abundant FAP, most of which appears membrane-associated. As reported, FAP was absent in SV-40 transformed VA-13 fibroblasts [5]. FIG. 1B shows results for FAP and POP activity assays, using highly selective, specific substrates and inhibitors designed and synthesized in the inventors lab [27]. Overlying media was first removed from each cell culture after which cells were washed with physiologic buffer and overlaid with fresh buffer. FAP or POP inhibitor was added, and each culture assayed with time for both FAP and POP activity. By using the specific substrate C95, which is cleaved only by FAP or POP, and the high affinity POP inhibitor J94 which has strict specificity for POP, but none towards FAP, it was possible to measure each enzyme's activity [27]. For each cell type, total prolyl-specific endopeptidase activity on intact cell membranes was determined using C95 substrate, which is cleaved at equal rates by FAP or POP; on parallel cultures J94 inhibitor was added to block solely that activity due to POP, thereby defining the remaining endopeptidase activity as uniquely attributable to membrane-associated FAP (FIGS. 1B, 3, 4B, 5B, 6 & 8B). As expected, the dipeptidase, DPPIV, neither cleaved C95 substrate nor was it inhibited by M83 or J94. The previous studies showed that APCE and FAP have essentially identical activities [12], thereby allowing the use of an APCE standard curve to determine moles of active FAP on the cell surface and hence, the number of FAP proteinase molecules/cell. Therefore, knowing the FAP activity and number of WI-38 fibroblasts in a confluent well, each cell was estimated to have ~117,000 FAP molecules on its membrane surface. FIG. 1C demonstrates FAP by Western blot and FIG. 1D indicates that the majority of FAP is membrane-associated, with a lesser amount in the cytosol, which agrees with our confocal results. FIG. 1E shows POP by Western blot in both WI-38 and VA-13 fibroblasts, although the activity assay did not detect any surface accessible POP activity in VA-13 cells. The majority of POP is cytosolic with a significant fraction being membrane-associated, which agrees with our assay results of cell surface POP activity (FIG. 1F).

Neither FAP nor POP activity was found in media that had been in contact with cells for three days, indicating that neither enzyme was shed or released (data not shown). When fresh buffer was again placed over the cells, both FAP and POP activities were found to be unchanged and immediately detectable, thereby supporting the membrane location of both enzymes. As can be seen in FIG. 1B, WI-38 fibroblasts yielded higher FAP than POP activity. In FIG. 1C, immunoblot analyses of lysates derived from a specified number of cells of each cell type, using the cellular content of α-tubulin (50 kDa) and actin (43 kDa) as protein load controls, showed relative FAP levels in accord with those estimated by confocal microscopy of corresponding immunostained cells or by endopeptidase activity measurements. As shown in FIG. 2, amino acid sequence determinations for tryptic peptides of the isolated putative FAP protein band from each cell type ensured that the ~100 kDa band from WI-38 fibroblasts was indeed FAP.

Figure 3:
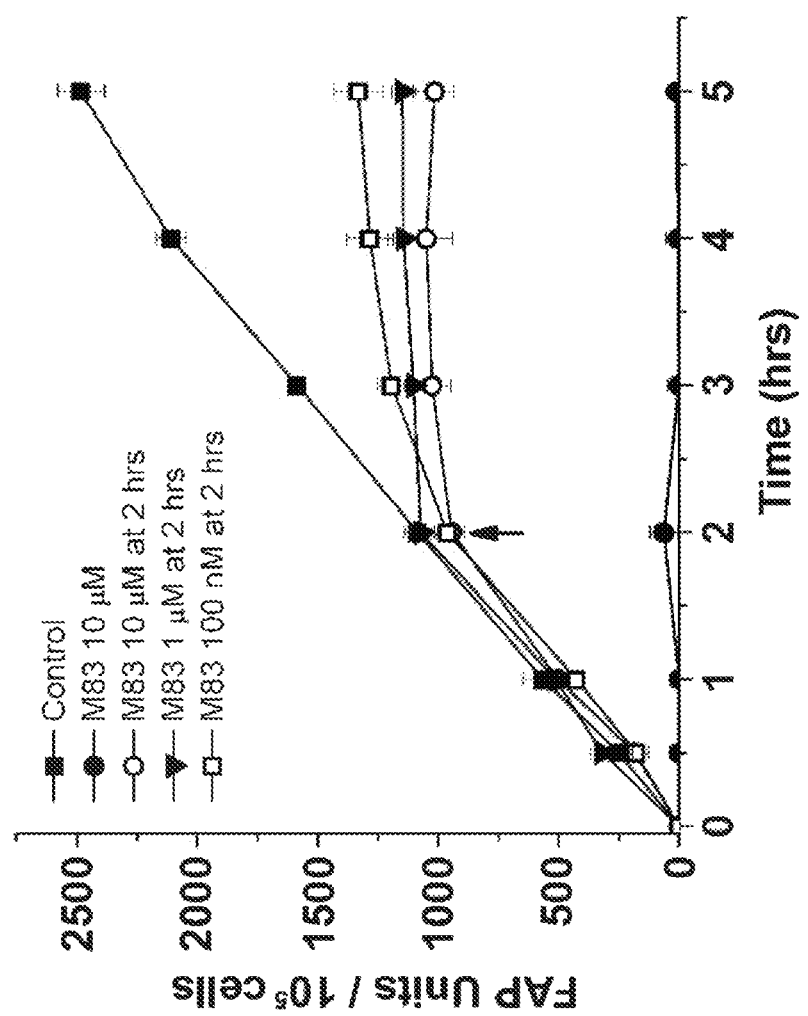
FIG. 3 shows the dose-response inhibition of FAP activity on WI-38 fibroblast surfaces by a FAP inhibitor compound designated as "M83" (acetyl-Arg-AEEA-(D)Ala-(L)boro-Pro). WI-38 fibroblasts were grown on plastic, washed once with HBSS, after which the M83 inhibitor 10 μM in HBSS was added at zero time to one set, and buffer only to the other four sets. The fluorescent substrate C95 was added to all sets of wells and Δ fluorescence/min, reflecting cleavage of C95 over time, was allowed to proceed for two hours when 10 μM, 1 μM or 100 nM of the M83 inhibitor was added to each of three sets of wells. As shown, each inhibitor concentration instantly, and essentially totally, inhibited the proteolytic activity of FAP on the cell surface.

FIG. 3 illustrates the effectiveness and rapidity of FAP and POP inhibition by the pseudo-peptide inhibitor construct, M83. Cultured W-I38 cells were exposed to the inhibitor at either the beginning of the assay, or after incubation for two hours with the substrate C95 that is cleaved by FAP or POP. After an increasing fluorescent signal indicated the accrual of significant proteolytic activity, the addition of even nanomolar concentrations of inhibitor M83 instantly abolished endopeptidase activity as evidenced by lack of further fluorescence increase.

Figure 4:
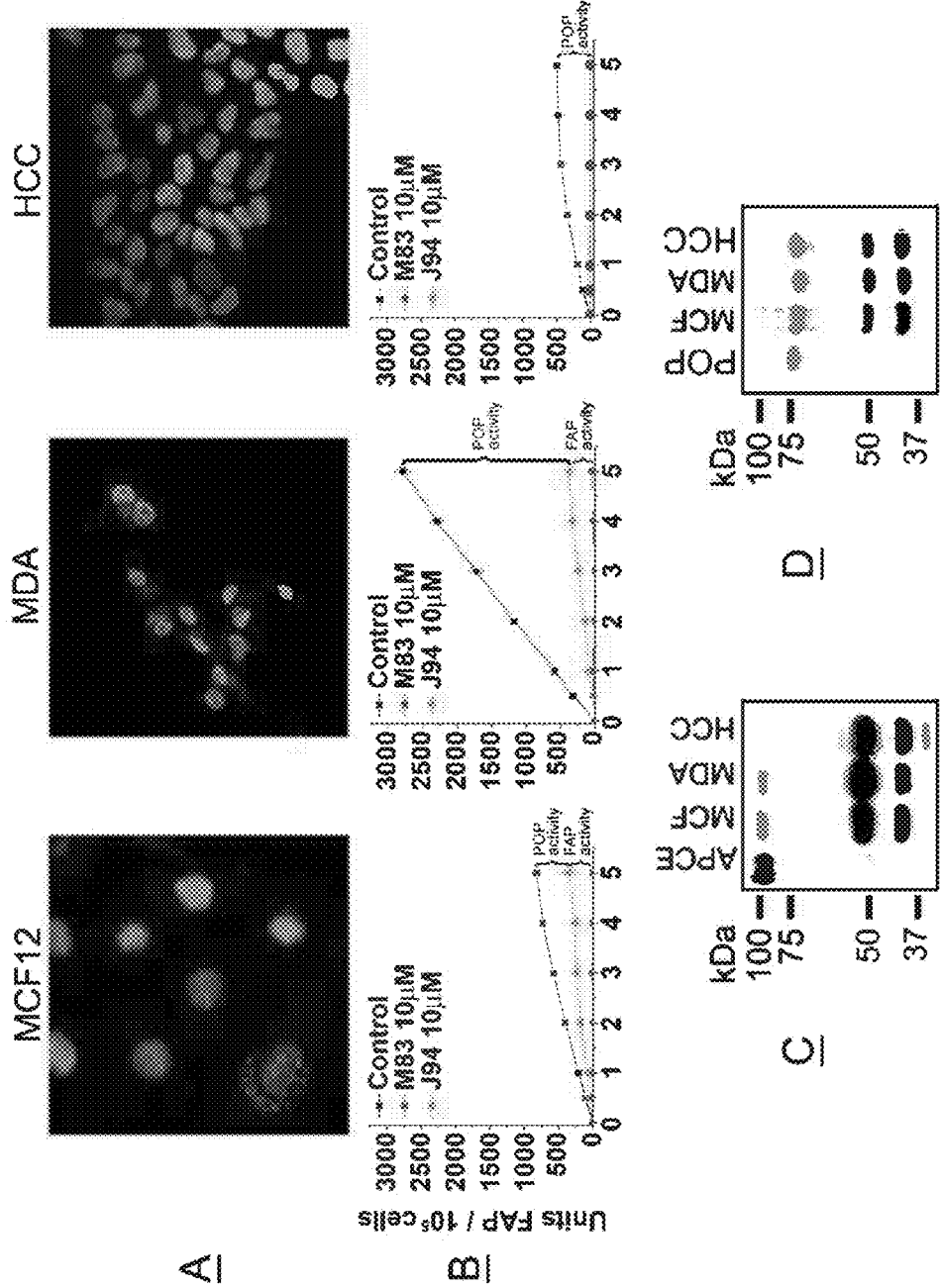
FIG. 4 is a characterization of FAP and POP in normal breast and breast cancer cells. Panel A. Confocal images of permeabilized MCF-12A (normal breast cells), MDA-MB436 or HCC1419 (breast cancer cells) grown on glass slides and labeled with mAb F19 to FAP followed by anti-mouse-AlexaFluor 568 (red) and DAPI (green). Panel B. FAP and POP activities on surfaces of normal and breast cancer cells grown on plastic wells as measured by cleavage of fluorescent substrate C95, and using the POP specific inhibitor J94 to separate the two activities. One FAP unit=Δ fluorescence/min on cleavage of C95 by one ng APCE. Panel C. Immunostains of cell lysates from normal and breast cancer cell cultures, using mAb 6D2 to FAP. APCE 1 ng was used as a positive control, while intracellular contents of α-tubulin (50 kDa) and actin (43 kDa) were used for standardizing the amount of cell lysate protein applied in each lane. Panel D. Immunostains of cell lysates from normal and breast cancer cell cultures using goat anti-POP. POP 1 ng was used as a positive control, while α-tubulin (50 kDa) and actin (43 kDa) served as load controls.

As shown in FIG. 4, three methods of assessment, namely: confocal microscopy, Western blotting, and endopeptidase activity, indicated that normal human MCF-12A breast cells or human breast carcinoma MDA-MB 436 cells contained far less FAP protein and FAP activity than observed for WI-38 activated fibroblasts (FIG. 1). While POP activity for MCF-12A cells and WI-38 fibroblasts was similar, human MDA-MB436 breast cancer cells had about five times that amount. Human HCC1419 breast cancer cells possessed about the same amount of POP activity as MCF-12A normal breast cells; however, HCC1419 cancer cells contained neither FAP protein nor FAP activity. Without wishing to be bound by theory, over-expression of POP in neoplasms has not been explained, but recent results of Myohanen et al. [36] suggest that POP is responsible for a second-step proteolytic cleavage in the autoregulation of thymosin-β4 that yields the derivative tetrapeptide, acetyl-SDKP, which is known to be a potent stimulator of angiogenesis.

Figure 5:
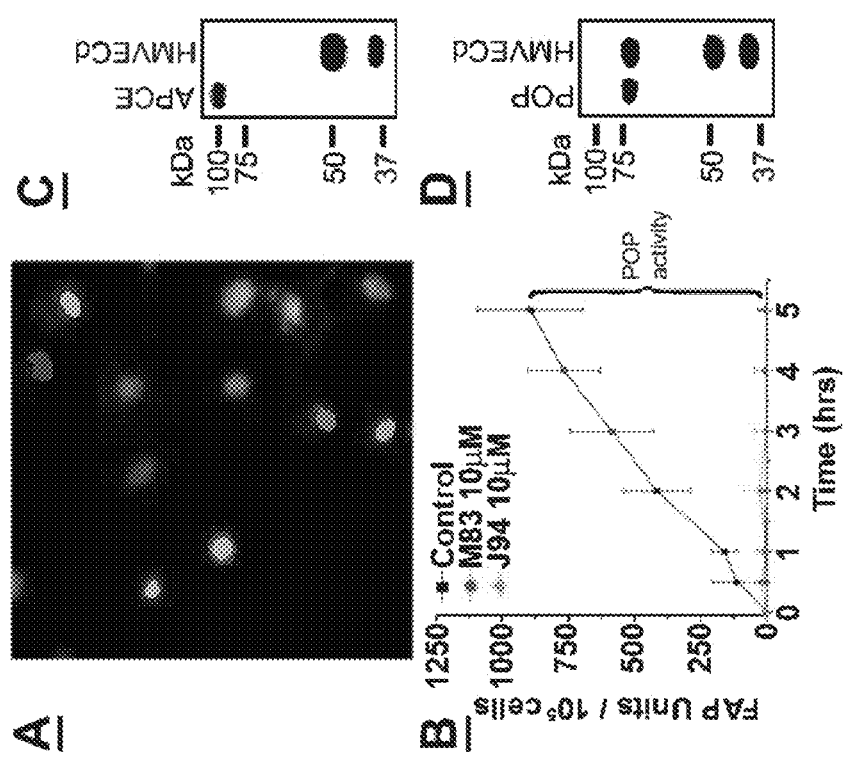
FIG. 5 is a characterization of FAP and POP in microvascular endothelial cells. Panel A. Confocal images of permeabilized HMVEC-d grown on glass slides and labeled with mAb F19 to FAP followed by anti-mouse-AlexaFluor 568 (red) and DAPI (green). Panel B. FAP and POP activities of endothelial cells grown on plastic wells measured by exactly the same methods described in FIGS. 1 and 4. Panel C. Immunostaining performed as described in FIGS. 1 and 4. Panel D. Immunostaining for POP performed as described in FIGS. 1 and 4.
Figure 6:
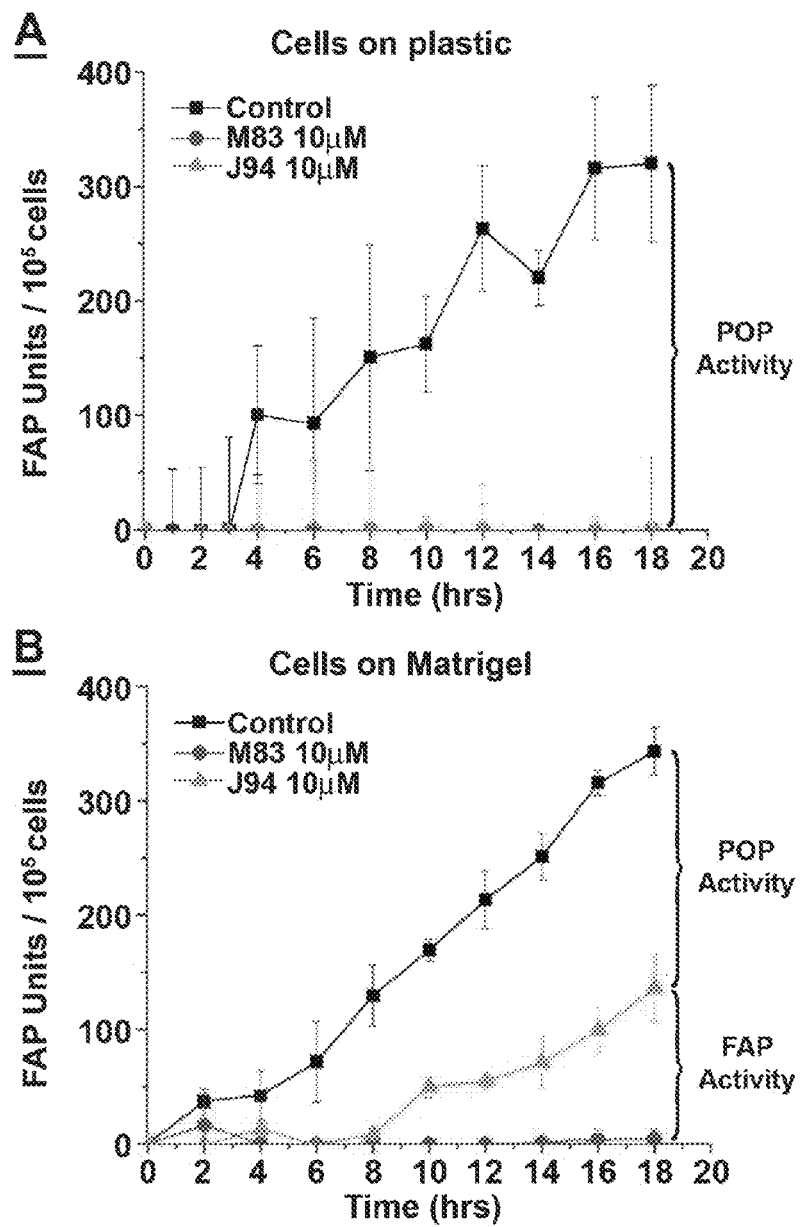
FIG. 6 shows FAP and POP activities in microvascular endothelial cells. Panel A. HMVEC-d cells plated on plastic wells allowed to settle for one hour, then inhibitors and substrates were added and fluorescence was measured over time for 18 hours. Panel B. HMVEC-d cells plated on Matrigel™ (BD Biosciences, San Jose, Calif.), allowed to settle for one hour to initiate tubule formation, and assayed for FAP and POP activities as in Panel A. Note that POP activity is detectable from the start in both assay conditions, but FAP activity only appears in the Matrigel™ assay at about four hours after tubule formation. Each point represents 15 readings over three separate experiments.

In FIG. 5A, confocal microscopy of cultured normal human dermal microvascular endothelial cells (HMVEC-d) on plastic demonstrated that cell-associated FAP was only occasionally encountered (panel A shows a field containing a rare positive cell). Western blotting of HMVEC-d lysates lacked a band consistent with FAP protein (FIG. 5C). Likewise, HMVEC-d were devoid of FAP activity, but HMVEC-d cultures did contain considerable POP activity, and as shown in FIG. 6B, when grown on Matrigel™ and allowed to form tubules over an 18-hr period, significant amounts of both FAP and POP activities were expressed and easily detectable. POP expression began just before capillary-like tubules started forming and continued as the complexity of the tubule network increased. Interestingly, detectable FAP expression as reflected by proteolytic activity began about 3-4 hours after tubule formation had clearly begun (i.e., 8 hours from plating HMVEC-d) and then continued to increase during the subsequent 18-hr. period of growth. These findings indicate the involvement of POP in the initiation and propagation of vessel formation, with the timing of FAP expression synchronized with ECM invasion by the forming capillary-type tubules. While FAP mRNA is up-regulated coincident with capillary formation [38], the observation that proteolytically active FAP protein becomes easily detectable and increases progressively with tubulogenesis has not been reported previously.

Figure 7:
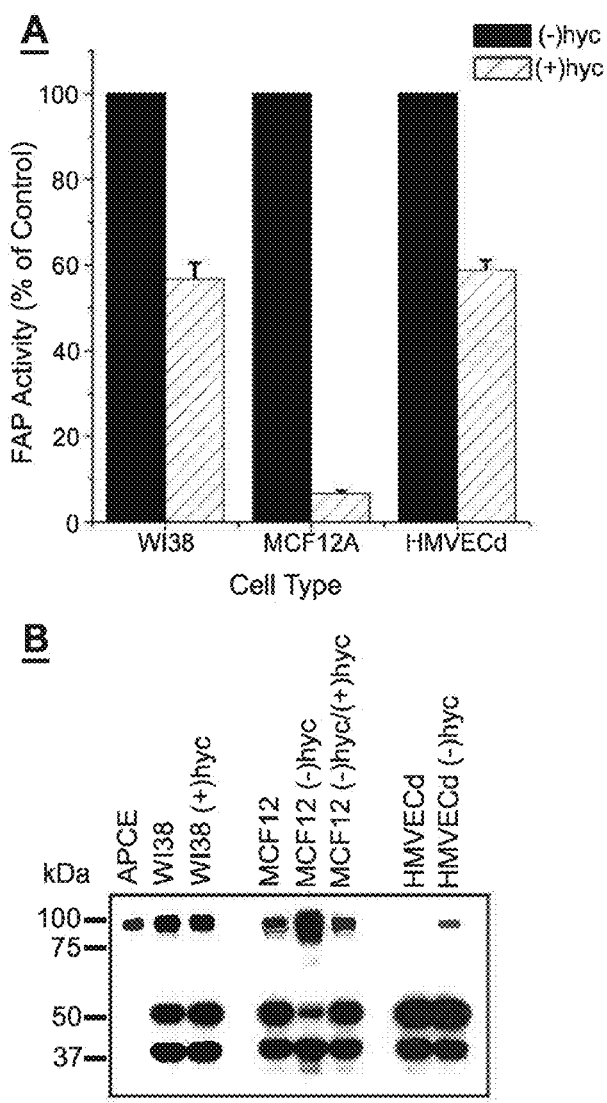
FIG. 7 shows FAP activity and FAP protein levels in stressed cells. WI-38 fibroblasts, MCF-12A normal breast cells, and HMVEC-d endothelial cells were grown in the presence of hydrocortisone (hyc) as customarily present in growth media, or in its absence. Cells were grown from 7 to 14 days as specified before assessing FAP activity and FAP protein levels. Panel A. FAP activity was measured as previously described. FAP activity in the absence of hydrocortisone was set at 100%, with the level of FAP activity in the presence of hydrocortisone expressed as a relative percent. Panel B. Immunostains of cell lysates from fibroblast, normal breast and endothelial cell cultures, using mAb 6D2 to FAP. APCE 1 ng is used as a positive control; α-tubulin (50 kDa) and actin (43 kDa) were used to standardize cell lysate protein amounts applied to each electrophoretic lane. MCF12A normal breast cells were grown in the absence of hydrocortisone, (-)hyc, for 7 days, followed by repletion of the normal media (+) hyc content, as supplied by Lonza, for 7 days, labeled (-)hyc/(+)hyc, prior to assessing both FAP activity and FAP protein concentration.
Figure 8:
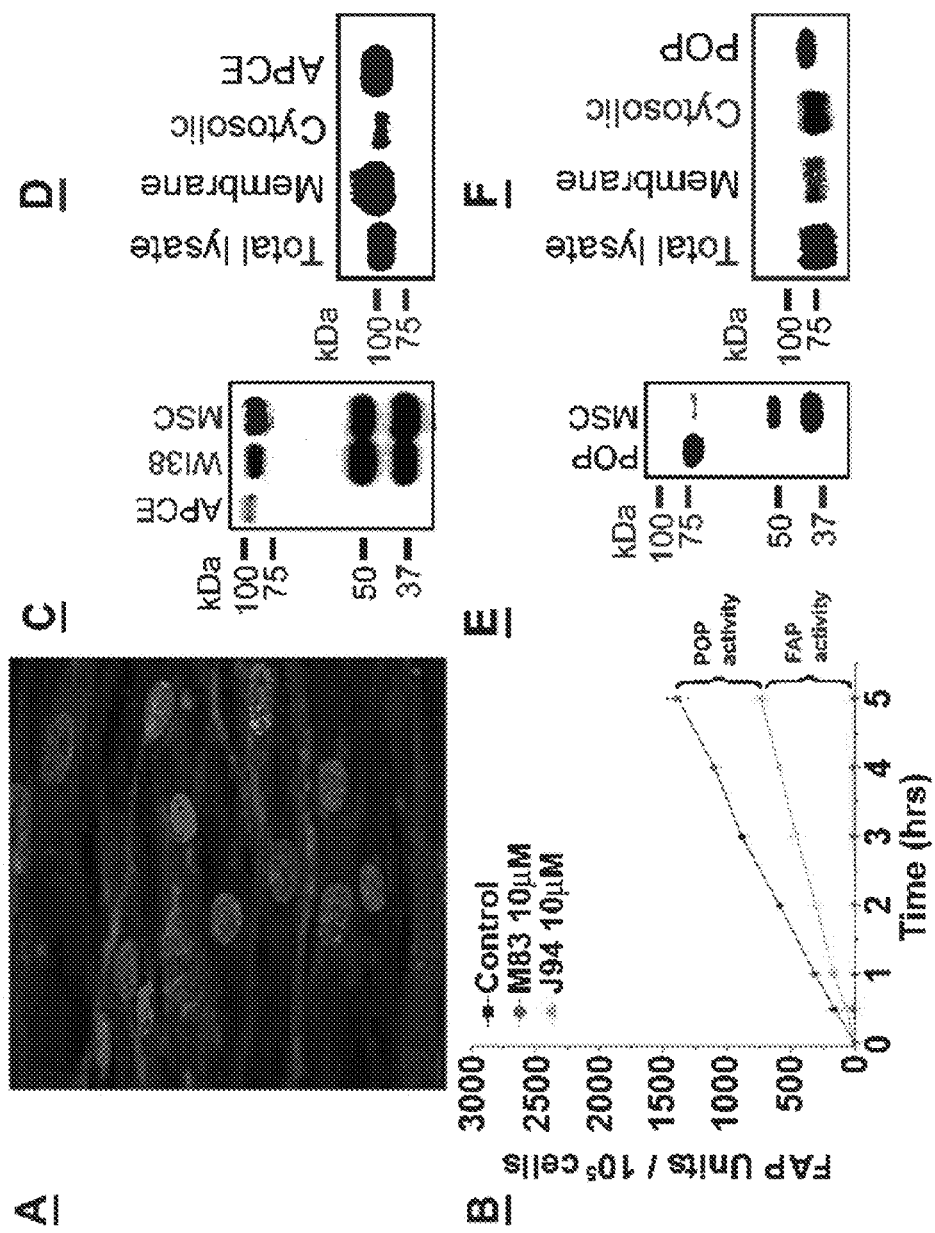
FIG. 8 shows the identification and characterization of FAP and POP in human mesenchymal stem cells (MSC). Panel A. Confocal image of permeabilized MSCs grown on glass slides and labeled with mAb F19 to FAP followed by anti-mouse-AlexaFluor 568 (red) and DAPI (green). Panel B. FAP and POP activities found on mesenchymal stem cell surfaces grown in plastic wells were measured exactly the same as described in FIGS. 1 and 4. Panel C. Immunostaining was performed as described in FIGS. 1 and 4. Panel D. Immunostaining for FAP in cell lysates and membrane and cytosolic fractions of mesenchymal stem cells was performed as described in FIG. 1. Panel E. Immunostaining for POP was performed as described in FIGS. 1 and 4. Panel F. Immunostaining for POP in cell lysates and membrane and cytosolic fractions of mesenchymal stem cells was performed as described in FIG. 1.

As shown in FIG. 7, when HMVEC-d and other selected cell types were stressed by removing hydrocortisone (hyc) from growth media, FAP became substantially over expressed as detected by Western blots of cell lysates and corresponding increases in FAP proteolytic activity. Identification of the over-expressed protein as FAP was validated by amino acid sequence determination as shown in FIG. 2. In FIG. 7A, the greatest over expression of FAP in response to omission of hydrocortisone in growth media was seen with MCF-12A normal breast cells. When hydrocortisone (hyc) was restored to concentrations used for growth of normal cells in culture, over expression of FAP by MCF-12A cells was totally reversed (FIG. 7B, compare MCF-12A (−) hyc and MCF-12A (−)hyc/(+)hyc). In contrast, removal of various growth factors (VEGF, bFGF, EGF, IGF) from growth media had no apparent effect, even after 42 days of culture.

Cancerous mesenchymal stem cells may be the best target in the search for a broadly applicable common denominator or "pan-tumor" approach for treating a large number of cancers [40, 41]. The inventors are aware of only one report showing FAP to be associated with mesenchymal stem cell membranes as evidenced by immunoselection of mesenchymal stem cells from human cryopreserved bone marrow with a FAP monoclonal antibody [42]. This prompted us to question whether mesenchymal stem cells, as the putative precursor to activated stromal fibroblasts [43], also expressed proteolytically active, membrane-bound FAP, and if so, how much relative to the activated fibroblast, and could it be readily inhibited? Confocal microscopy of permeabilized human mesenchymal cells in FIG. 8A shows most of the immunostained FAP in the cytosol, with relatively less in their membranes, which is opposite to what was observed for WI-38 fibroblasts. Western immunoblots of mesenchymal cell lysates (FIG. 8C) confirmed the large amount of FAP present and did identify POP protein as well (FIG. 8E). LC/MS/MS analysis of tryptic peptides from digestion of the ~100 kDa band in lysates of mesenchymal stem cells established the protein band as a subunit of homodimeric FAP (FIG. 2). When mesenchymal membrane and cytosolic fractions were separated and subjected to Western blotting, it was clear that FAP is abundant on membranes and is in the cytosol to a lesser extent (FIG. 8D). In contrast, the majority of POP is in the cytosol, with a lesser amount found in the membrane (FIG. 8F). Mesenchymal cells and fibroblasts had about the same amount of FAP and POP activity, which might be expected given that mesenchymal cells are believed precursors of fibroblast. Assuming mesenchymal stem cell and fibroblast membranes are impermeable to C95 substrate because of the latter's positive charge and lack of hydrophobicity, cytosolic FAP activity in live cells would not likely contribute to measurement of membrane activity.

Figure 9:
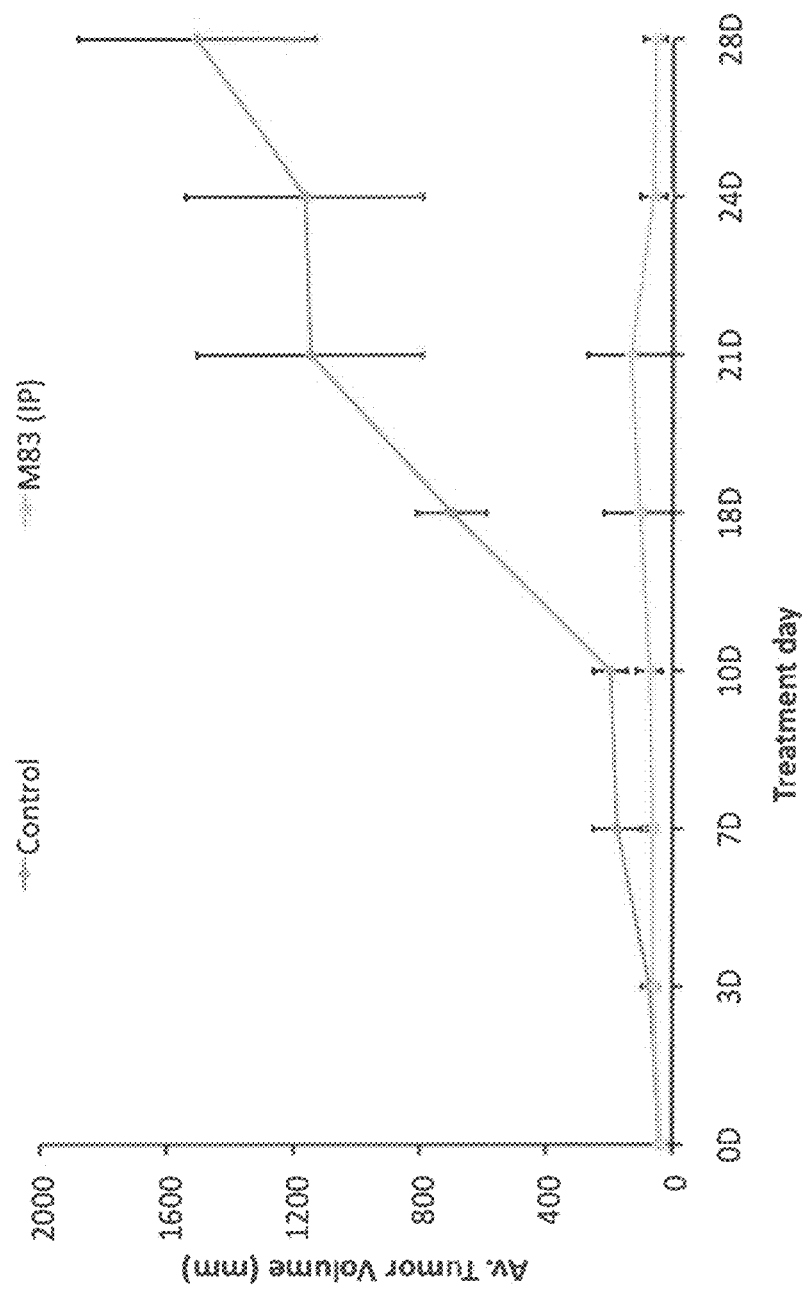
FIG. 9 is a graph showing the inhibition of lung cancer xenografts in nude mice by compound M83 over a period of 28 days.

FIG. 9 shows the inhibition of lung cancer xenografts in nude mice by compound M83. Mice were given a 50 μl injection into each hind leg consisting of human lung adenocarcinoma epithelial cells ($2 \times 10^6$ cells) suspended in Matrigel™. After ten days the tumors had grown to an estimated 40 mm³, so M83 treatment was initiated (day 0 in graph). For the M83 treatment group, mice were given a daily intraperitoneal injection of 26.5 micrograms of M83 dissolved in 20 microliters of sterile saline. The mice of the control group were given an intraperitoneal injection of 20 microliters of sterile saline. After ten days, tumors in the control group began to grow rapidly, while tumors in mice treated with M83 failed to progress and by day 28 of treatment the average tumor volume was no greater than on day zero. In addition, one of the six tumors in the M83 treatment group had completely disappeared. The treatment groups consisted of three mice each with two tumors per mouse. FIGS. 10A and B are micrographs which demonstrate that application of 50 μm of compound J94 inhibited formation of capillary-like tubes in Matrigel™.

Figure 11:
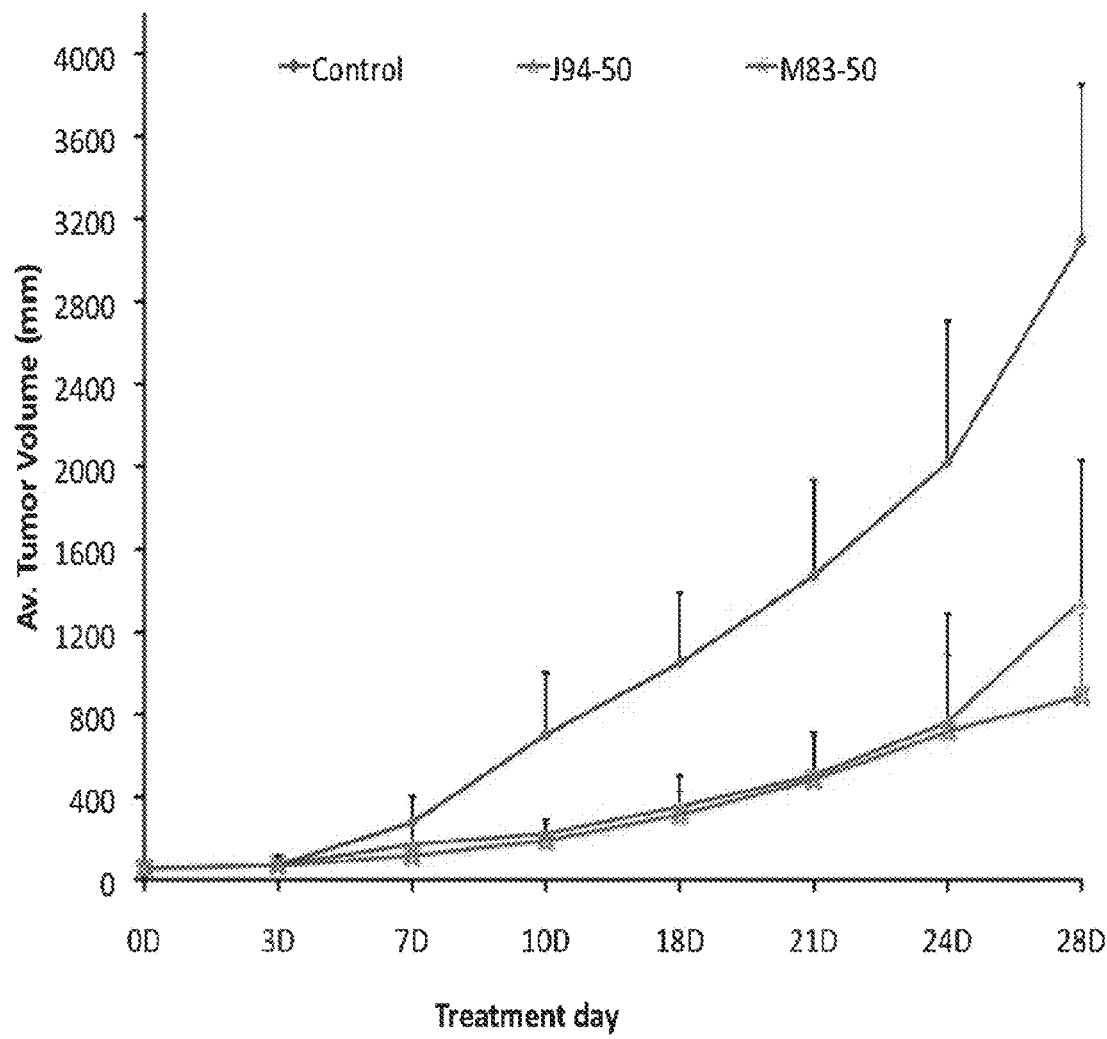
FIG. 11 is a graph showing the inhibitory effects of M83 and J94 on growth of colon cancer tumors.

FIG. 11 depicts results which show that J94 inhibitor is effective in HCT116 human colon cancer xenografts in immunodeficient mice treated with J94 or M83. Clearly during the 28-day treatment period, J94 diminished cancer growth by ~75%, while M83 was slightly more effective than this. Although not shown here, microscopy of control and treated tumor specimens by Immunohistocytochemistry confirmed the presence of FAP and POP; demonstrated thicker bundles of collagen surrounding residual tumor; widespread areas of tumor cell apoptosis within treated tumors; strong suggestions of diminished capillary vascularity within treated tumors; and lastly, raised the question of whether tumor cell autophagy might also have occurred. In every occasion of J94 or M83 treatment, xenografted human tumors, be they colon cancer or lung cancer, showed strikingly decreased rates of growth.

FAP is considered to be a potent diagnostic or therapeutic target because it is (i) over-expressed by activated stromal fibroblasts in epithelial-derived human malignancies [19-21] and (ii) absent in normal adult tissues and benign tumors [19-21]. Santos et al. [21] showed that targeted gene disruption or pharmacologic inhibition of FAP proteinase activity slowed or halted tumor growth in mouse models of endogenous lung cancer and human colon cancer. In both tumor scenarios, cancer cell proliferation decreased, collagen increased, and myofibroblast content and blood vessel density decreased, prompting the suggestion that targeting fibroblasts within the tumor microenvironment might be useful therapeutically. To date, however, studies of such relatively non-specific putative inhibitors of FAP, e.g. Glu-boroPro or Val-boroPro, show that both also inhibit physiologically important DPPIV. On a molar basis both are ~50% or less effective for inhibiting POP than FAP and, both undergo cyclization and have abbreviated survivals in vivo that detract from therapeutic potential.

Recently Kraman and associates [44] reported that absence of FAP-expressing cells in mice allowed effective vaccination strategies for immunological control of epithelial cell-derived cancer growth. In that study, direct efforts were not made to determine whether FAP proteolytic activity was necessary for immunosuppressive effects within the tumor environment. In accord with both proteolytic and non-proteolytic roles for FAP in malignant growth, Huang et al. [45] have recently suggested that FAP proteolytic function is important in extracellular matrix degradation, but that other undefined properties (possibly immunologic) of FAP may promote tumor growth. While the function of FAP proteinase activity within malignancies has been poorly understood, most efforts to assess FAP as a therapeutic target have involved inhibiting its proteinase activity. Characterizing the proteolytic activity of membrane-inserted FAP has been unusually difficult, since a physiologic or pathologic substrate has not been definitively identified. Having discovered APCE and its only known physiologic substrate, precursor $\alpha_2$-antiplasmin ($\alpha_2$AP), the inventors took advantage of APCE being essentially identical to FAP and used the amino acid sequence surrounding the scissile bond of precursor $\alpha_2$AP to design stable and highly effective water-soluble inhibitors of APCE and FAP [27]. In the process, it was discovered that a positively charged residue in the P6 or P7 position augmented the cleavage rate significantly [29, 46], and this proved useful in developing a highly effective FAP inhibitor, M83, and the fluorescent substrate C95 [27, 29]. Both manifested high affinity and good specificity for FAP; however, these properties were also directed toward another prolyl-specific serine protease family member, namely, POP, which the inventors, like others [33, 47], have found associated with selected normal and cancer cell lines.

To put the overall endopeptidase activity on cell membrane surfaces in perspective, it was reasoned that FAP and POP activities should each be quantitated. The C95 FAP and POP substrate as well as the M83 inhibitor of both FAP and POP were used in conjunction with a novel and highly specific J94 POP inhibitor, the latter having no effect on FAP, for estimating membrane-associated FAP or POP endopeptidase activity. POP cleaves selected peptides of <~30 residues. Most recently, as noted above, POP has been proposed to have a significant role in angiogenesis by cleaving a short derivative peptide from the ubiquitously tissue-distributed thymosin β4, to yield the tetrapeptide compound, acetyl-SDKP, that stimulates angiogenesis [35].

Notably, the dipeptidase proteolytic activity of either membrane-inserted or soluble DPPIV is directed only toward amino-terminal dipeptides, and as expected, DPPIV neither cleaved C95 substrate nor was it inhibited by M83 or J94. Other prolyl dipeptidases have the added negative of being cytosolic or inactive and hence are unlikely to cleave extracellular substrates or to become inhibited by water-soluble agents that must permeate the cell membrane.

The results provided herein show that activated fibroblasts, i.e., those that are (i) rapidly dividing, (ii) highly mobile, (iii) contain α-smooth muscle actin (myofibroblasts), and (iv) manifest enhanced ECM deposition, also have impressive amounts of FAP on their membranes with lesser amounts in the cytosol (FIGS. 1A and D). Cancer-associated fibroblasts are activated fibroblasts that typically help form the stromal scaffolding of metastatic epithelial-derived tumor microenvironments. Assays for FAP or POP activity in the non-serum containing media in which cells grew, or in buffer washes of those cell cultures, were always devoid of proteolytic activity, thereby supporting FAP and POP as membrane-associated proteins, with each in a conformation that allows proteolytic activity to be easily and rapidly inhibited. Subtraction of the activity specifically inhibited by the POP inhibitor J94 provided an assessment of accessible FAP proteolytic activity. Assuming equivalent recoveries of FAP from different cell types, the amount of FAP protein and FAP proteinase activity in WI-38 fibroblasts exceeded that in any other cell, except for mesenchymal stem cells. Immunoreactive FAP protein samples recovered from WI-38 fibroblasts, MDA-MB436 cancer cells, HMVEC-d deprived of hydrocortisone, or mesenchymal stem cells all had essentially identical amino acid sequences to that established for FAP. Proteolytic assays confirmed that viral-transformed VA-13 human fibroblasts lacked both membrane-associated FAP and POP activities.

Small amounts of FAP and POP activity and protein in normal breast cells, about the same amount of FAP activity in MDA-MB436 human metastatic breast cancer cells, were demonstrated; however, the latter cells contained about 6 times the amount of POP activity compared to normal breast cells. It seems reasonable that within hormonally-induced cyclical tissue responses, an occasional normal breast parenchymal cell might be induced to express a small amount of FAP and POP. HCC1419 intraluminal primary breast cancer cells contained barely detectable FAP by immunostaining, and no assayable FAP proteinase activity; POP activity was greatly reduced, but POP protein, likely intracellular, was easily demonstrable. Within a growing HCC1419 tumor, however, this does not preclude the possibility that requisite stroma within the breast cancer malignancy may express FAP and POP. The basis of abundant POP activity found on MDA-MB436 breast cancer cells (FIG. 4) remains obscure, despite such increases having been noted before in several other malignancies. Larrinaga et al. [33] reported POP on cell membranes of various human cancers, but usually in amounts not much different than those on corresponding normal cell types; however, cytosolic POP within cancers cells was regularly significantly increased beyond that in corresponding normal cells, which is in keeping with our finding for HCC1419 breast cancer cells.

Endothelial cells (HMVEC-d) grown on plastic contained a rare FAP-positive cell by immunostaining, but no FAP protein by immunoblotting or proteinase assay. However, as confluence was achieved, significant POP activity was expressed concordantly. As expected, tube formation did not occur on plastic despite endothelial cell confluency; however, POP expression continued unabated. FAP was not expressed during the 72-hr growth period (FIG. 5B). In contrast, when grown on Matrigel™, by about four hours, the HMVEC-d cells began to align progressively in tubular structures and POP expression continued to increase (FIG. 6B). Shortly after tube-like capillaries began forming, FAP activity became demonstrable (FIG. 6B). By about 18 hours, well-defined capillary-like networks dominated. These results prompted the speculation that expression of proteolytically active FAP might be synchronized with capillary growth to foster invasiveness of developing microvasculature into the ECM [37]. Aimes et al. [38] noted endothelial expression of mRNA transcripts of several serine proteases, including FAP, in association with the nature of the culture substratum and progression of angiogenesis. The finding of increasing FAP proteolytic activity demonstrates that the increased FAP mRNA is actually translated during tubule formation. Several studies have suggested that endothelial cells within the developing microvasculature of malignant tissues express FAP [8, 39, 50]. While it might be speculated that FAP's presence could result from growth of fibroblast-related pericytes that accompany neovascularization, fibroblasts were never observed in HMVEC-d cultures. These results indicate that membrane-inserted proteolytically-active FAP is synthesized and expressed by endothelial cells as they participate in angiogenesis.

As shown by immunoblotting and activity assays (FIG. 7), stress caused by removal of hydrocortisone from growth media stimulated both HMVEC-d and MCF12A normal breast cells to over-express FAP, which was directly documented as the source of proteolytic activity by its isolation and amino acid sequence (FIG. 2). Notably, replenishment of hydrocortisone returned MCF12A expression of FAP to levels before its removal (FIG. 7). Similarly, WI-38 activated fibroblasts which are ordinarily grown in the absence of hydrocortisone, showed a detectable decrease in FAP expression when hydrocortisone was added. Analogous effects with hydrocortisone have been noted before with other cells, e.g., decreased hydrocortisone in cultures of selected normal human epithelial cells was associated with increased syntheses of both urokinase and tissue plasminogen activator [51]. These data suggest that cells are capable of altering expression of FAP if they should become stressed as might occur in a rapidly expanding metastatic tumor microenvironment.

Mesenchymal stem cells give rise to progenitor adipocytes, bone cells and myocytes, and are also considered precursive to fibroblasts [43,52]. Conceivably, activated mesenchymal stem cells could arise as a consequence of epithelial-mesenchymal cell transformation [53] and represent the progenitor cell of the "tumor niche". Some propose, however, that mesenchymal stem cells originate from bone marrow, move into a selected tissue and undergo malignant transformation to produce cancer cells characteristic of that tissue [40,54]. Others consider that a precursive cancer stem cell might derive from a dormant multipotent cell unique to a specific tissue. The amounts of FAP we observed for mesenchymal stem cells by confocal microscopy and Western blotting (FIG. 8) were more than for WI-38 activated fibroblasts (FIG. 1). The multiple roles of mesenchymal cells suggest they may exist in an activated state more frequently than do fibroblasts. This may be particularly true with respect to mesenchymal cell involvement in malignancies and account for the large amount of FAP we observed in these cells.

The results provided herein allow the following conclusions: (i) FAP and POP are both expressed on the membranes of cells critical to tumor niche formation in primary tumors or metastases, namely: cancer-associated fibroblasts, mesenchymal stem cells, selected cancer cells, and endothelial cells as the latter participate in angiogenesis. (ii) In their membrane bound form, each enzyme is proteolytically active and easily accessible for efficient inhibition by a new soluble, high affinity, selective pseudo-peptide inhibitor that meets structural requirements for the respective enzyme's substrate-binding region. (iii) Endothelial cells readily express POP as they grow, and in addition, membrane-inserted proteolytically-active FAP is synthesized and expressed as tubulogenesis occurs [38,50]. (iv) FAP and POP are therapeutic targets for a large number of cancers and the two new inhibitors, M83 and J94, have use as therapeutics against commonly encountered epithelial-derived cancers and their metastatic foci.

Although the presently disclosed and claimed inventive concept(s) and the advantages thereof have been described in detail, it should be understood that various changes, substitutions and alterations can be made herein without departing from the spirit and scope of the presently disclosed and claimed inventive concept(s) as defined in the present disclosure. Moreover, the scope of the present application is not intended to be limited to the particular embodiments of the processes, compositions of matter, means, methods and steps described in the specification. As one of ordinary skill in the art will readily appreciate from the disclosure of the presently disclosed and claimed inventive concept(s), processes, compositions of matter, means, methods, or steps, presently existing or later to be developed that perform substantially the same function or achieve substantially the same result as the corresponding embodiments described herein may be utilized according to the presently disclosed and claimed inventive concept(s). Accordingly, the presently disclosed and claimed inventive concept(s) is intended to include within their scope all such processes, compositions of matter, means, methods, or steps.

TABLE 1

Cyclic Amines and Proline Analogs 4-hydroxypyrrolidine-2-carboxylic acid (cis and trans)
3-phenylpyrrolidine-2-carboxylic acid (cis and trans)
3-hydroxypyrrolidine-2-carboxylic acid (cis and trans)
4-hydroxypyrrolidine-2-carboxylic acid (cis and trans)
2-ethylthiazolidine-4-carboxylic acid (cis and trans)
2-methylthiazolidine-4-carboxylic acid (cis and trans)
2-phenylthiazolidine-4-carboxylic acid (cis and trans)
5,5-dimethylthiazolidine-4-carboxylic acid

TABLE 1-continued

Cyclic Amines and Proline Analogs thiazolidine-2-carboxylic acid (cis and trans)
thiazolidine-4-carboxylic acid (cis and trans)
azetidine-2-carboxylic acid (cis and trans)
thiazolidine-2-carboxylic acid (cis and trans)
thiazolidine-4-carboxylic acid (cis and trans)
amino-L-proline methyl ester
cyano-L-proline methyl ester
4-cyano-L-proline
3,4-dehydro-L-proline
Boronylproline
4-fluoro-L-proline
Nitrileproline
lysyl piperidide
N-(4-chlorobenzyl)4-0x0-4-(1-piperidinyl)-1,3-(s)-butane-diamine
bromocyclopentyl carboxylic acid
chlorocyclopentyl carboxylic acid
fluorocyclopentyl carboxylic acid
cis-3-methylproline
cis-3-ethylproline
cis-3-isopropylproline
cis-3-isopentanylproline
homoproline
benzyl-proline
(2-fluoro-benzyl)-proline
(3-fluoro-benzyl)-proline
(4-fluoro-benzyl)-proline
(2-chloro-benzyl)-proline
(3-chloro-benzyl)-proline
(4-chloro-benzyl)-proline
(2-bromo-benzyl)-proline
(3-bromo-benzyl)-proline
(4-bromo-benzyl)-proline
phenethyl-proline
(2-methyl-benzyl)-proline
(3-methyl-benzyl)-proline
(4-methyl-benzyl)-proline
(2-nitro-benzyl)-proline
(3-nitro-benzyl)-proline
(4-nitro-benzyl)-proline
(1-Naphthalenylmethyl)-proline
(2-Naphthalenylmethyl)-proline
(2,4-dichloro-benzyl)-proline
(3,4-dichloro-benzyl)-proline
(3,4-difluoro-benzyl)-proline
(2-trifluoromethyl-benzyl)-proline
(3-trifluoromethyl-benzyl)-proline
(4-trifluoromethyl-benzyl)-proline
(2-cyano-benzyl)-proline
(3-cyano-benzyl)-proline
(4-cyano-benzyl)-proline
(4-iodo-benzyl)-proline
(3-Phenyl-allyl)-proline
(3-Phenyl-allyl)-proline
(3-Phenyl-propyl)-proline
(4-tert-Butyl-benzyl)-proline
Benzhydryl-proline
(4-Biphenylmethyl)-proline
(4-Thiazolylmethyl)-proline
(3-Benzo[b]thiophenylmethyl)-proline
(2-Thiophenylmethyl)-proline
(5-Bromo-2-Thiophenylmethyl)-proline
(3-Thiophenylmethyl)-proline
(2-Furanylmethyl)-proline
(2-Pyridinylmethyl)-proline
(3-Pyridinylmethyl)-proline
(4-Pyridinylmethyl)-proline
Proline carbonitrile
Allyl-proline
Propynyl-proline
4-Phenyl-pyrrolidine-3-carboxylic acid
4-(2-fluoro-phenyl)-pyrrolidine-3-carboxylic acid
4-(3-fluoro-phenyl)-pyrrolidine-3-carboxylic acid
trans-4-(4-fluoro-phenyl)-pyrrolidine-3-carboxylic acid
trans-4-(2-chloro-phenyl)-pyrrolidine-3-carboxylic acid
trans-4-(3-chloro-phenyl)-pyrrolidine-3-carboxylic acid
4-(4-chloro-phenyl)-pyrrolidine-3-carboxylic acid
4-(2-bromo-phenyl)-pyrrolidine-3-carboxylic acid
4-(3-bromo-phenyl)-pyrrolidine-3-carboxylic acid
trans-4-(4-bromo-phenyl)-pyrrolidine-3-carboxylic acid
4-(2-methyl-phenyl)-pyrrolidine-3-carboxylic acid
4-(3-methyl-phenyl)-pyrrolidine-3-carboxylic acid
4-(4-methyl-phenyl)-pyrrolidine-3-carboxylic acid
4-(2-nitro-phenyl)-pyrrolidine-3-carboxylic acid
4-(3-nitro-phenyl)-pyrrolidine-3-carboxylic acid
4-(4-nitro-phenyl)-pyrrolidine-3-carboxylic acid
4-(1-naphthyl)-pyrrolidine-3-carboxylic acid
4-(2-naphthyl)-pyrrolidine-3-carboxylic acid
4-(2,5-dichloro-phenyl)-pyrrolidine-3-carboxylic acid
4-(2,3-dichloro-phenyl)-pyrrolidine-3-carboxylic acid
4-(2-trifluoromethyl-phenyl)-pyrrolidine-3-carboxylic acid
4-(3-trifluoromethyl-phenyl)-pyrrolidine-3-carboxylic acid
4-(4-trifluoromethyl-phenyl)-pyrrolidine-3-carboxylic acid
4-(2-cyano-phenyl)-pyrrolidine-3-carboxylic acid
4-(3-cyano-phenyl)-pyrrolidine-3-carboxylic acid
4-(4-cyano-phenyl)-pyrrolidine-3-carboxylic acid
4-(2-methoxy-phenyl)-pyrrolidine-3-carboxylic acid
4-(3-methoxy-phenyl)-pyrrolidine-3-carboxylic acid
4-(4-methoxy-phenyl)-pyrrolidine-3-carboxylic acid
4-(2-hydroxy-phenyl)-pyrrolidine-3-carboxylic acid
4-(3-hydroxy-phenyl)-pyrrolidine-3-carboxylic acid
4-(4-hydroxy-phenyl)-pyrrolidine-3-carboxylic acid
4-(2,3-dimethoxy-phenyl)-pyrrolidine-3-carboxylic acid
4-(3,4-dimethoxy-phenyl)-pyrrolidine-3-carboxylic acid
4-(3,5-dimethoxy-phenyl)-pyrrolidine-3-carboxylic acid
4-(2-pyridinyl)-pyrrolidine-3-carboxylic acid
4-(3-pyridinyl)-pyrrolidine-3-carboxylic acid
4-(6-methoxy-3-pyridinyl)-pyrrolidine-3-carboxylic acid
4-(4-pyridinyl)-pyrrolidine-3-carboxylic acid
4-(2-thienyl)-pyrrolidine-3-carboxylic acid
4-(3-thienyl)-pyrrolidine-3-carboxylic acid
4-(2-furanyl)-pyrrolidine-3-carboxylic acid
4-isopropyl-pyrrolidine-3-carboxylic acid
Pyrrolidides
2-nitrile pyrrolidine
Fluoropyrrolidine
Bromopyrrolidine
Chloropyrrolidine
Pyrrolidinenitriles
Piperidine
Pyrrolidone
Azetidine
pipecolic acid
Piperidide
3-carboxy-1,2,3,4-tetrahydro-isoquinoline
2-carboxy-2,3-dehydroindole
Cyclopentyls
N-substituted cyclopentyl derivatives
Cyclohexyls
N-substituted cyclohexyl derivatives
val-boroPro
glu-boroPro
Oxazolidine
and proline analogs and derivatives as defined in U.S. Pat. No. 4,428,939; 6,890,904; 4,762,821 and Published Applications 2003/0158114; 20050272703; and 2006/0287245.

TABLE 2

APCE/FAP Inhibitor Compounds

| Number | Compound |
|---|---|
| 1 | Argininyl-(8-amino-3,6-Dioxaoctanoyl)-D-Alaninyl-boroProline |
| 2 | Acetyl-Argininyl-(8-amino-3,6-Dioxaoctanoyl)-D-Alaninyl-boroProline |
| 3 | Benzoyl-Argininyl-(8-amino-3,6-Dioxaoctanoyl)-D-Alaninyl-boroProline |
| 4 | Benzyloxycarbonyl-Argininyl-(8-amino-3,6-Dioxaoctanoyl)-D-Alaninyl-boroProline |
| 5 | Succinyl-Argininyl-(8-amino-3,6-Dioxaoctanoyl)-D-Alaninyl-boroProline |
| 6 | Acetyl-β-homoArgininyl-(8-amino-3,6-Dioxaoctanoyl)-D-Alaninyl-boroProline |
| 7 | Acetyl-Lysinyl-(8-amino-3,6-Dioxaoctanoyl)-D-Alaninyl-boroProline |
| 8 | Acetyl-β-homoLysinyl-(8-amino-3,6-Dioxaoctanoyl)-D-Alaninyl-boroProline |
| 9 | Acetyl-Ornithinyl-(8-amino-3,6-Dioxaoctanoyl)-D-Alaninyl-boroProline |
| 10 | Acetyl-Diaminopropionyl-(8-amino-3,6-Dioxaoctanoyl)-D-Alaninyl-boroProline |
| 11 | Acetyl-Histidinyl-(8-amino-3,6-Dioxaoctanoyl)-D-Alaninyl-boroProline |
| 12 | Acetyl-Argininyl-(11-amino-3,6,9-Trioxaundecanoyl)-D-Alaninyl-boroProline |
| 13 | Acetyl-Argininyl-(12-amino-4,7,10-trioxadodecanoyl)-D-Alaninyl-boroProline |
| 14 | Acetyl-Argininyl-β-Alaninyl-β-Alaninyl-D-Alaninyl-boroProline |
| 15 | Acetyl-Argininyl-(6-aminohexanoyl)-D-Alaninyl-boroProline |
| 16 | Acetyl-Argininyl-(8-aminooctanoyl)-D-Alaninyl-boroProline |
| 17 | Acetyl-Argininyl-Glycinyl-Glycinyl-Glycinyl-D-Alaninyl-boroProline |
| 18 | Acetyl-Argininyl-Glycinyl-Glycinyl-Serinyl-D-Alaninyl-boroProline |
| 19 | Acetyl-Argininyl-Glutaminyl-Leucinyl-Threoninyl-Serinyl-D-Alaninyl-boroProline |
| 20 | Acetyl-Argininyl-Glycinyl-Glycinyl-boroProline |
| 21 | Acetyl-Argininyl-(8-amino-3,6-Dioxaoctanoyl)-Serinyl-Glycinyl-boroProline |
| 22 | Acetyl-Argininyl-(8-amino-3,6-Dioxaoctanoyl)-Glycinyl-boroProline |
| 23 | Acetyl-Argininyl-(8-amino-3,6-Dioxaoctanoyl)-D-Serinyl-boroProline |
| 24 | Acetyl-Argininyl-(8-amino-3,6-Dioxaoctanoyl)-D-Alaninyl-2-nitrile pyrrolidine |
| 25 | Acetyl-Argininyl-(8-amino-3,6-Dioxaoctanoyl)-D-Alaninyl-pyrrolidine-2-carbonitrile |
| 26 | Acetyl-Argininyl-(8-amino-3,6-Dioxaoctanoyl)-D-Alaninyl-prolinal |
| 27 | Acetyl-Argininyl-(8-amino-3,6-Dioxaoctanoyl)-D-Alaninyl-2-nitrile piperidine |
| 28 | Acetyl-Argininyl-(8-amino-3,6-Dioxaoctanoyl)-D-Alaninyl-2-nitrile-4-fluoro-pyrrolidine |

Amino acids or amino acid derivatives or analogs may be either L- or D-form unless specified.

TABLE 3

POP Inhibitor Compounds

| Number | Compound |
|---|---|
| 1 | Lysyl-Leucyl-Arginyl-boroProline |
| 2 | Acetyl-Lysyl-Leucyl-Arginyl-boroProline |
| 3 | Benzoyl-Lysyl-Leucyl-Arginyl-boroProline |
| 4 | Benzyloxycarbonyl-Lysyl-Leucyl-Arginyl-boroProline |
| 5 | Succinyl-Lysyl-Leucyl-Arginyl-boroProline |
| 6 | Pyrazinyl-Lysyl-Leucyl-Arginyl-boroProline |
| 7 | Acetyl-β-homoLysyl-Leucyl-Arginyl-boroProline |
| 8 | Acetyl-Diaminopropionyl-Leucyl-Arginyl-pyrrolidine-2-carbonitrile |
| 9 | Acetyl-Ornithinyl-Leucyl-Arginyl-boroProline |
| 10 | Pyrazinyl-β-homoArginyl-Leucyl-Arginyl-Prolinal |
| 11 | Acetyl-Arginyl-Leucyl-Arginyl-boroProline |
| 12 | Acetyl-Aspartyl-Leucyl-Arginyl-boroProline |
| 13 | Acetyl-Glutamyl-Leucyl-Arginyl-2-nitrile piperdine |
| 14 | Pyrazinyl-Lysyl-Isoleucyl-Arginyl-boroProline |
| 15 | Acetyl-Lysyl-Valyl-Arginyl-boroProline |
| 16 | Acetyl-Lysyl-Alanyl-Arginyl-boroProline |
| 17 | Acetyl-Lysyl-Phenylalanyl-Arginyl-2-nitrile-4-fluoro-pyrrolidine |
| 18 | Pyrazinyl-Lysyl-Threonyl-Arginyl-boroProline |
| 19 | Acetyl-Lysyl-Glycyl-Arginyl-boroProline |
| 20 | Acetyl-Lysyl-Leucyl-Lysyl-boroProline |
| 21 | Acetyl-Lysyl-Leucyl-Diaminopropionyl-pyrrolidine-2-carbonitrile |
| 22 | Pyrazinyl-Arginyl-Leucyl-Lysyl-boroProline |
| 23 | Acetyl-Lysyl-(8-amino-3,6-Dioxaoctanoyl)-Arginyl-boroProline |
| 24 | Acetyl-Argininyl-(8-amino-3,6-Dioxaoctanoyl)-Arginyl-boroProline |
| 25 | Pyrazinyl-Argininyl-(epsilon-amino-Caproyl)-Arginyl-Prolinal |
| 26 | Acetyl-Argininyl-(gamma-amino-Butyryl)-Arginyl-boroProline |
| 27 | Acetyl-Lysyl-Leucyl-Arginyl-pyrrolidine-2-carbonitrile |
| 28 | Acetyl-Lysyl-Leucyl-Arginyl-prolinal |
| 29 | Pyrazinyl-Lysyl-Leucyl-Arginyl-2-nitrile piperidine |
| 30 | Acetyl-Lysyl-Leucyl-Arginyl-2-nitrile-4-fluoro-pyrrolidine |
| 31 | Acetyl-Lysyl-Leucyl-Arginyl-4-fluoro-piperidine-2-boronic acid |
| 32 | Acetyl-Lysyl-Leucyl-Arginyl-4-fluoro prolinal |
| 33 | Acetyl-Lysyl-Leucyl-Arginyl-4,4-difluoro-piperidine-2-boronic acid |
| 34 | Acetyl-Lysyl-Leucyl-Arginyl-4,4-difluoro-pyrrolidine-2-boronic acid |
| 35 | Acetyl-Lysyl-Leucyl-Arginyl-2-nitrile-4,4-difluoro-pyrrolidine |
| 36 | Acetyl-Lysyl-Leucyl-Arginyl-2-nitrile-4,4-difluoro-piperidine |

Amino acids or amino acid derivatives or analogs may be either L- or D-form unless specified.

TABLE 4

POP Inhibitor Compounds

| Number | Compound |
|---|---|
| 1 | Lysyl-Leucyl-Lysyl-boroProline |
| 2 | Acetyl-Lysyl-Leucyl-Homolysyl-pyrrolidine-2-carbonitrile |

TABLE 4-continued

POP Inhibitor Compounds

| Number | Compound |
|---|---|
| 3 | Benzoyl-Lysyl-Leucyl-Homoarginyl-boroProline |
| 4 | Benzyloxycarbonyl-Lysyl-Leucyl-Histidyl-boroProline |
| 5 | Succinyl-Lysyl-Leucyl-Ornithyl-Prolinal |
| 6 | Pyrazinyl-Lysyl-Leucyl-Diaminobutyryl-boroProline |
| 7 | Acetyl-β-homoLysyl-Leucyl-Diaminopropionyl-boroProline |
| 8 | Acetyl-Diaminopropionyl-Leucyl-Homoarginyl-boroProline |
| 9 | Aminobenzoyl-Ornithinyl-Leucyl-Diaminobutyryl-boroProline |
| 10 | Acetyl-β-homoArginyl-Leucyl-Diaminopropionyl-2-nitrile piperdine |
| 11 | Pyrazinyl-Arginyl-Leucyl-Lysyl-boroProline |
| 12 | Benzoyl-Aspartyl-Leucyl-Homolysyl-boroProline |
| 13 | Acetyl-Glutamyl-Leucyl-Homoarginyl-2-nitrile-4-fluoro-pyrrolidine |
| 14 | Succinyl-Lysyl-Isoleucyl-Histidyl-boroProline |
| 15 | Acetyl-Lysyl-Valyl-Ornithyl-boroProline |
| 16 | Acetyl-Lysyl-Alanyl-Diaminobutyryl-pyrrolidine-2-carbonitrile |
| 17 | Aminobenzoyl-Lysyl-Phenylalanyl-Diaminopropionyl-boroProline |
| 18 | Pyrazinyl-Lysyl-Threonyl-Lysyl-Prolinal |
| 19 | Benzoyl-Lysyl-Glycyl-Homolysyl-boroProline |
| 20 | Acetyl-Lysyl-Leucyl-Homoarginyl-boroProline |
| 21 | Succinyl-Aspartyl-Leucyl-Diaminopropionyl-2-nitrile piperdine |
| 22 | Acetyl-Aspartyl-Leucyl-Lysyl-boroProline |
| 23 | Aminobenzoyl-Aspartyl-(8-amino-3,6-Dioxaoctanoyl)-Arginyl-2-nitrile-4-fluoro-pyrrolidine |
| 24 | Acetyl-Glutamyl-(8-amino-3,6-Dioxaoctanoyl)-Arginyl-boroProline |
| 25 | Benzoyl-Glutamyl-(epsilon-amino-Caproyl)-Arginyl-pyrrolidine-2-carbonitrile |
| 26 | Acetyl-Glutamyl-(gamma-amino-Butyryl)-Arginyl-boroProline |
| 27 | Succinyl-Glutamyl-Leucyl-Arginyl-pyrrolidine-2-carbonitrile |
| 28 | Pyrazinyl-Lysyl-Leucyl-Lysyl-prolinal |
| 29 | Acetyl-Lysyl-Leucyl-Histidyl-2-nitrile piperidine |
| 30 | Acetyl-Lysyl-Leucyl-Ornithyl-2-nitrile-4-fluoro-pyrrolidine |
| 31 | Acetyl-Histidyl-Leucyl-Arginyl-4-fluoro-piperidine-2-boronic acid |
| 32 | Acetyl-Histidyl-Leucyl-Arginyl-4-fluoro prolinal |
| 33 | Acetyl-Aspartyl-Leucyl-Arginyl-4,4-difluoro-piperidine-2-boronic acid |
| 34 | Acetyl-Ornithyl-Leucyl-Arginyl-4,4-difluoro-pyrrolidine-2-boronic acid |
| 35 | Acetyl-Ornithyl-Leucyl-Arginyl-2-nitrile-4,4-difluoro-pyrrolidine |
| 36 | Acetyl-Glutamyl-Leucyl-Arginyl-2-nitrile-4,4-difluoro-piperidine |

Amino acids or amino acid derivatives or analogs may be either L- or D-form unless specified.

TABLE 5

POP Inhibitor Compounds

| Number | Compound |
|---|---|
| 1 | Lysyl-Leucyl-Arginyl-boroProline |
| 2 | Acetyl-Aspartyl-Leucyl-Lysyl-boroProline |
| 3 | Benzoyl-Lysyl-Leucyl-Homolysyl-boroProline |
| 4 | Benzyloxycarbonyl-Lysyl-Leucyl-Ornithyl-pyrrolidine-2-carbonitrile |
| 5 | Succinyl-Glutamyl-Leucyl-Diaminobutyryl-boroProline |
| 6 | Pyrazinyl-Lysyl-Leucyl-Diaminopropionyl-boroProline |
| 7 | Acetyl-β-homoLysyl-Leucyl-Lysyl-boroProline |
| 8 | Aminobenzoyl-Diaminopropionyl-Leucyl-Homolysyl-Prolinal |
| 9 | Acetyl-Ornithinyl-Leucyl-Arginyl-boroProline |
| 10 | Benzoyl-β-homoArginyl-Leucyl-Arginyl-boroProline |
| 11 | Acetyl-Aspartyl-Leucyl-Histidyl-boroProline |
| 12 | Succinyl-Aspartyl-Leucyl-Arginyl-2-nitrile piperidine |
| 13 | Pyrazinyl-Glutamyl-Leucyl-Arginyl-boroProline |
| 14 | Aminobenzoyl-Lysyl-Isoleucyl-Arginyl-boroProline |
| 15 | Acetyl-Glutamyl-Valyl-Arginyl-2-nitrile-4-fluoro-pyrrolidine |
| 16 | Benzoyl-Lysyl-Alanyl-Arginyl-boroProline |
| 17 | Acetyl-Lysyl-Phenylalanyl-Arginyl-pyrrolidine-2-carbonitrile |
| 18 | Succinyl-Aspartyl-Threonyl-Arginyl-boroProline |
| 19 | Acetyl-Lysyl-Glycyl-Arginyl-boroProline |
| 20 | Aminobenzoyl-Glutamyl-Leucyl-Lysyl-Prolinal |
| 21 | Acetyl-Lysyl-Leucyl-Diaminopropionyl-boroProline |
| 22 | Benzoyl-Arginyl-Leucyl-Lysyl-boroProline |
| 23 | Pyrazinyl-Aspartyl-(8-amino-3,6-Dioxaoctanoyl)-Arginyl-2-nitrile piperidine |
| 24 | Succinyl-Argininyl-(8-amino-3,6-Dioxaoctanoyl)-Arginyl-boroProline |
| 25 | Aminobenzoyl-Argininyl-(epsilon-amino-Caproyl)-Arginyl-2-nitrile-4-fluoro-pyrrolidine |
| 26 | Succinyl-Glutamyl-(gamma-amino-Butyryl)-Arginyl-boroProline |
| 27 | Benzoyl-Lysyl-Leucyl-Arginyl-pyrrolidine-2-carbonitrile |

TABLE 5-continued

POP Inhibitor Compounds

| Number | Compound |
|---|---|
| 28 | Aminobenzoyl-Lysyl-Leucyl-Arginyl-prolinal |
| 29 | Pyrazinyl-Lysyl-Leucyl-Arginyl-2-nitrile piperidine |
| 30 | Succinyl-Lysyl-Leucyl-Arginyl-2-nitrile-4-fluoro-pyrrolidine |
| 31 | Benzoyl-Lysyl-Leucyl-Lysyl-4-fluoro-piperidine-2-boronic acid |
| 32 | Succinyl-Lysyl-Leucyl-Lysyl-4-fluoro prolinal |
| 33 | Pyrazinyl-Lysyl-Leucyl-Histidyl-4,4-difluoro-piperidine-2-boronic acid |
| 34 | Aminobenzoyl-Lysyl-Leucyl-Histidyl-4,4-difluoro-pyrrolidine-2-boronic acid |
| 35 | Benzoyl-Lysyl-Leucyl-Ornithyl-2-nitrile-4,4-difluoro-pyrrolidine |
| 36 | Pyrazinyl-Lysyl-Leucyl-Homoarginyl-2-nitrile-4,4-difluoro-piperidine |

Amino acids or amino acid derivatives or analogs may be either L- or D-form unless specified.

TABLE 6

Catalytic efficiencies of APCE/FAP, DPPIV and POP for Tic-Pro-AFC

| Prolyl peptidase | $K_m$ (μM) | $k_{cat}$ (s$^{-1}$) | $k_{cat}/K_m$ (M$^{-1}$s$^{-1}$) |
|---|---|---|---|
| APCE/FAP | 53 ± 5 | 1.19 ± 0.11 | 2.2 × 10$^4$ |
| DPPIV | 33 ± 2 | 1.49 ± 0.12 | 4.5 × 10$^4$ |
| POP | 161 ± 12 | 0.76 ± 0.01 | 4.7 × 10$^3$ |

TABLE 7

APCE/FAP, DPPIV, and POP Inhibition Constants ($K_i$) Of Various Inhibitor Compounds

| Inhibitor Compound | APCE/FAP $K_i$ (nM) | DPPIV $K_i$ (nM) | Selectivity $K_i$ (DPPIV) $K_i$ (APCE-FAP) | POP $K_i$ (nM) | Selectivity $K_i$ (POP) $K_i$ (APCE/FAP) |
|---|---|---|---|---|---|
| Ac-Gly-L-boroPro | 20.7 | 314 | 15.2 | 23.3 | 1.1 |
| Ac-Arg-peg-Gly-DL-boroPro | 3.1 | 1150 | 371 | | |
| Ac-Arg-Gly-Gly-DL-boroPro | 22.9 | 341 | 14.9 | | |
| Ac-Arg-peg-D-Ala-D-boroPro | 189 | 20480 | 108 | | |
| Ac-Arg-peg-D-Ala-L-boroPro | 5.7 | 6136 | 1076 | 7.4 | 1.3 |
| Ac-Arg-peg-D-Ala-DL(25:75%)-boroPro | 7.7 | ND | — | | |
| Ac-Arg-peg-D-Ala-DL(50:50%)-boroPro | 9.5 | 11170 | 1176 | | |
| Ac-Arg-peg-D-Ala-DL(75:25%)-boroPro | 18.3 | ND | — | | |
| Ac-Arg-peg-D-Asp-L-boroPro | 1377 | 7129 | 5.2 | 23.9 | 0.02 |
| Ac-Arg-peg-Ser-Gly-L-boroPro | 2.7 | 861 | 319 | 2.9 | 1.1 |
| Ac-Arg-peg-Gly-L-boroPro | 1.8 | 440 | 244 | 2.1 | 1.2 |
| Ac-Arg-Gly-Gly-L-boroPro | 17.2 | 322 | 18.7 | 1.6 | 0.1 |

Data represent the best-fit value ± the standard error, inhibition of APCE activity.

REFERENCES

The following references, to the extent that they provide exemplary procedural or other details supplementary to those set forth herein, are specifically incorporated herein by reference in their entireties.

1. Garin-Chesa P, Old U, Rettig W J (1990) Cell surface glycoprotein of reactive stromal fibroblasts as a potential antibody target in human epithelial cancers. Proc Natl Acad Sci USA 87:7235-7239.
2. Park J E, Lenter M C, Zimmermann R N, Garin-Chesa P, Old U, Rettig W J (1999) Fibroblast activation protein, a dual specificity serine protease expressed in reactive human tumor stromal fibroblasts. J Biol Chem 274:36505-36512.
3. Rettig W J, Garin-Chesa P, Beresford H R, Oettgen H F, Melamed M R, Old U (1988) Cell-surface glycoproteins of human sarcomas: differential expression in normal and malignant tissues and cultured cells. Proc Natl Acad Sci USA 85:3110-3114.
4. Niedermeyer J, Garin-Chesa P, Kriz M, Hilberg F, Mueller E, Bamberger U, Rettig W J, Schnapp A (2001) Expression of the fibroblast activation protein during mouse embryo development. Int J Dev Biol 45:445-447.
5. Rettig W J, Garin-Chesa P, Healey J H, Su S L, Ozer H L, Schwab M, Albino A P, Old U (1993) Regulation and heteromeric structure of the fibroblast activation protein in normal and transformed cells of mesenchymal and neuroectodermal origin. Cancer Res 53:3327-3335.
6. Acharya P S, Zukas A, Chandan V, Katzenstein A L, Pure E (2006) Fibroblast activation protein: a serine protease expressed at the remodeling interface in idiopathic pulmonary fibrosis. Hum Pathol 37:352-360.
7. Wang X M, Yao T W, Nadvi N A, Osborne B, McCaughan G W, Gorrell M D (2008) Fibroblast activation protein and chronic liver disease. Front Biosci 13:3168-3180.

8. Ge Y, Zhan F, Barlogie B, Epstein J, Shaughnessy J, Jr., Yaccoby S (2006) Fibroblast activation protein (FAP) is upregulated in myelomatous bone and supports myeloma cell survival. Br J Haematol 133:83-92.
9. Dohi O, Ohtani H, Hatori M, Sato E, Hosaka M, Nagura H, ltoi E, Kokubun S (2009) Histogenesis-specific expression of fibroblast activation protein and dipeptidylpeptidase-IV in human bone and soft tissue tumours. Histopathology 55:432-440.
10. Bauer S, Jendro M C, Wadle A, Kleber S, Stenner F, Dinser R, Reich A, Faccin E, Godde S, Dinges H, Muller-Ladner U, Renner C (2006) Fibroblast activation protein is expressed by rheumatoid myofibroblast-like synoviocytes. Arthritis Res Ther 8:R171.
11. lwasa S, Okada K, Chen W T, Jin X, Yamane T, Ooi A, Mitsumata M (2005) 'Increased expression of seprase, a membrane-type serine protease, is associated with lymph node metastasis in human colorectal cancer'. Cancer Lett 227:229-236.
12. Lee K N, Jackson K W, Christiansen V J, Lee C S, Chun J G, McKee P A (2006) Antiplasmin-cleaving enzyme is a soluble form of fibroblast activation protein. Blood 107:1397-1404.
13. Aggarwal S, Brennen W N, Kole T P, Schneider E, Topaloglu O, Yates M, Cotter R J, Denmeade S R (2008) Fibroblast activation protein peptide substrates identified from human collagen I derived gelatin cleavage sites. Biochemistry 47:1076-1086.
14. Niedermeyer J, Scanlan M J, Garin-Chesa P, Daiber C, Fiebig H H, Old U, Rettig W J, Schnapp A (1997) Mouse fibroblast activation protein: molecular cloning, alternative splicing and expression in the reactive stroma of epithelial cancers. Int J Cancer 71:383-389.
15. Christiansen V J, Jackson K W, Lee K N, McKee P A (2007) Effect of fibroblast activation protein and alpha2-antiplasmin cleaving enzyme on collagen types I, III, and IV. Arch Biochem Biophys 457:177-186.
16. Huang Y, Wang S, Kelly T (2004) Seprase promotes rapid tumor growth and increased microvessel density in a mouse model of human breast cancer. Cancer Res 64:2712-2716.
17. Cheng J D, Weiner L M (2003) Tumors and their microenvironments: tilling the soil. Commentary re: A. M. Scott et al., A Phase I dose-escalation study of sibrotuzumab in patients with advanced or metastatic fibroblast activation protein-positive cancer. Clin. Cancer Res., 9: 1639-1647, 2003. Clin Cancer Res 9:1590-1595.
18. Kalluri R, Zeisberg M (2006) Fibroblasts in cancer. Nat Rev Cancer 6:392-401.
19. Puré E (2009) The road to integrative cancer therapies: emergence of a tumor-associated fibroblast protease as a potential therapeutic target in cancer. Expert Opin Ther Targets 13:967-973.
20. Hayward S W (2010) Preclinical assessment of fibroblast activation protein as a target for antitumor therapy. Future Oncol 6:347-349.
21. Santos A M, Jung J, Aziz N, Kissil J L, Pure E (2009) Targeting fibroblast activation protein inhibits tumor stromagenesis and growth in mice. J Clin Invest 119:3613-3625.
22. Kelly T, Adams J, Bachovchin W, Barton R, Campbell S, Courts S, Kennedy C, Snow R (1993) Immunosuppressive boronic acid dipeptides: correlation between conformation and activity. J Am Chem Soc 115:12637-12638.
23. Rosenblum J S, Kozarich J W (2003) Prolyl peptidases: a serine protease subfamily with high potential for drug discovery. Curr Opin Chem Biol 7:496-504.
24. Narra K, Mullins S R, Lee H O, Strzemkowski-Brun B, Magalong K, Christiansen V J, McKee P A, Egleston B, Cohen S J, Weiner L M, Meropol N J, Cheng J D (2007) Phase II trial of single agent Val-boroPro (Talabostat) inhibiting Fibroblast Activation Protein in patients with metastatic colorectal cancer. Cancer Biol Ther 6:1691-1699.
25. Goossens F, De M, I, Vanhoof G, Scharpe S (1996) Distribution of prolyl oligopeptidase in human peripheral tissues and body fluids. Eur J Clin Chem Clin Biochem 34:17-22.
26. Liu J M, Kusinski M, Ilic V, Bignon J, Hajem N, Komorowski J, Kuzdak K, Stepien H, Wdzieczak-Bakala J (2008) Overexpression of the angiogenic tetrapeptide AcSDKP in human malignant tumors. Anticancer Res 28:2813-2817.
27. Lee K N, Jackson K W, Christiansen V J, Dolence E K, McKee P A (2011) Enhancement of fibrinolysis by inhibiting enzymatic cleavage of precursor alpha2-antiplasmin. J Thromb Haemost 9:987-996.
28. Lee K N, Jackson K W, Christiansen V J, Chung K H, McKee P A (2004) A novel plasma proteinase potentiates alpha2-antiplasmin inhibition of fibrin digestion. Blood 103:3783-3788.
29. Lee K N, Jackson K W, Terzyan S, Christiansen V J, McKee P A (2009) Using substrate specificity of antiplasmin-cleaving enzyme for fibroblast activation protein inhibitor design. Biochemistry 48:5149-5158.
30. Gorrao S S, Hemerly J P, Lima A R, Melo R L, Szeltner Z, Polgar L, Juliano M A, Juliano L (2007) Fluorescence resonance energy transfer (FRET) peptides and cyclo-retro-inverso peptides derived from bradykinin as substrates and inhibitors of prolyl oligopeptidase. Peptides 28:2146-2154.
31. Szeltner Z, Polgar L (2008) Structure, function and biological relevance of prolyl oligopeptidase. Curr Protein Pept Sci 9:96-107.
32. Scanlan M J, Raj B K, Calvo B, Garin-Chesa P, Sanz-Moncasi M P, Healey J H, Old U, Rettig W J (1994) Molecular cloning of fibroblast activation protein alpha, a member of the serine protease family selectively expressed in stromal fibroblasts of epithelial cancers. Proc Natl Acad Sci USA 91:5657-5661.
33. Larrinaga G, Perez I, Blanco L, Lopez J I, Andres L, Etxezarraga C, Santaolalla F, Zabala A, Varona A, lrazusta J (2010) Increased prolyl endopeptidase activity in human neoplasia. Regul Pept 163:102-106.
34. Busek P, Stremenova J, Sedo A (2008) Dipeptidyl peptidase-IV enzymatic activity bearing molecules in human brain tumors—good or evil? Front Biosci 13:2319-2326.
35. Liu J M, Garcia-Alvarez M C, Bignon J, Kusinski M, Kuzdak K, Riches A, Wdzieczak-Bakala J (2010) Overexpression of the natural tetrapeptide acetyl-N-ser-asp-lys-pro derived from thymosin beta4 in neoplastic diseases. Ann N Y Acad Sci 1194:53-59.
36. Myohanen T T, Tenorio-Laranga J, Jokinen B, Vazquez-Sanchez R, Moreno-Baylach M J, Garcia-Horsman J A, Mannisto P T (2011) Prolyl oligopeptidase induces angiogenesis both in vitro and in vivo in a novel regulatory manner. Br J Pharmacol 163:1666-1678.
37. Wang T, Shi W (2009) Expression of fibroblast activation proteins in corneal stromal neovascularization. Curr Eye Res 34:112-117.

38. Aimes R T, Zijlstra A, Hooper J D, Ogbourne S M, Sit M L, Fuchs S, Gotley D C, Quigley J P, Antalis T M (2003) Endothelial cell serine proteases expressed during vascular morphogenesis and angiogenesis. Thromb Haemost 89:561-572.
39. Okada K, Chen W T, Iwasa S, Jin X, Yamane T, Ooi A, Mitsumata M (2003) Seprase, a membrane-type serine protease, has different expression patterns in intestinal- and diffuse-type gastric cancer. Oncology 65:363-370.
40. Karnoub A E, Dash A B, Vo A P, Sullivan A, Brooks M W, Bell G W, Richardson A L, Polyak K, Tubo R, Weinberg R A (2007) Mesenchymal stem cells within tumour stroma promote breast cancer metastasis. Nature 449:557-563.
41. Coghlin C, Murray G I (2010) Current and emerging concepts in tumour metastasis. J Pathol 222:1-15.
42. Bae S, Park C W, Son H K, Ju H K, Paik D, Jeon C J, Koh G Y, Kim J, Kim H (2008) Fibroblast activation protein alpha identifies mesenchymal stromal cells from human bone marrow. Br J Haematol 142:827-830.
43. Emura M, Ochiai A, Horino M, Arndt W, Kamino K, Hirohashi S (2000) Development of myofibroblasts from human bone marrow mesenchymal stem cells cocultured with human colon carcinoma cells and TGF beta 1. In Vitro Cell Dev Biol Anim 36:77-80.
44. Kraman M, Bambrough P J, Arnold J N, Roberts E W, Magiera L, Jones J O, Gopinathan A, Tuveson D A, Fearon D T (2010) Suppression of antitumor immunity by stromal cells expressing fibroblast activation protein-alpha. Science 330:827-830.
45. Huang Y, Simms A E, Mazur A, Wang S, Leon N R, Jones B, Aziz N, Kelly T (2011) Fibroblast activation protein-alpha promotes tumor growth and invasion of breast cancer cells through non-enzymatic functions. Clin Exp Metastasis 6:567-579.
46. Christiansen V J, Jackson K W, Lee K N, McKee P A (2007) The effect of a single nucleotide polymorphism on human alpha 2-antiplasmin activity. Blood 109:5286-5292.
47. Duke-Cohan J S, Morimoto C, Rocker J A, Schlossman S F (1995) A novel form of dipeptidylpeptidase IV found in human serum. Isolation, characterization, and comparison with T lymphocyte membrane dipeptidylpeptidase IV (CD26). J Biol Chem 270:14107-14114.
48. Garcia-Horsman J A, Mannisto P T, Venalainen J I (2007) On the role of prolyl oligopeptidase in health and disease. Neuropeptides 41:1-24.
49. Cavallo-Medved D, Rudy D, Blum G, Bogyo M, Caglic D, Sloane B F (2009) Live-cell imaging demonstrates extracellular matrix degradation in association with active cathepsin B in caveolae of endothelial cells during tube formation. Exp Cell Res 315:1234-1246.
50. Bhati R, Patterson C, Livasy C A, Fan C, Ketelsen D, Hu Z, Reynolds E, Tanner C, Moore D T, Gabrielli F, Perou C M, Klauber-DeMore N (2008) Molecular characterization of human breast tumor vascular cells. Am J Pathol 172:1381-1390.
51. Myohanen H, Virtanen I, Vaheri A (2001) Elimination of hydrocortisone from the medium enables tissue plasminogen activator gene expression by normal and immortalized nonmalignant human epithelial cells. Biol Chem 382:1563-1573.
52. Mishra P J, Mishra P J, Humeniuk R, Medina D J, Alexe G, Mesirov J P, Ganesan S, Glod J W, Banerjee D (2008) Carcinoma-associated fibroblast-like differentiation of human mesenchymal stem cells. Cancer Res 68:4331-4339.
53. Thiery J P, Acloque H, Huang R Y, Nieto M A (2009) Epithelial-mesenchymal transitions in development and disease. Cell 139:871-890.
54. Baguley B C (2006) Tumor stem cell niches: a new functional framework for the action of anticancer drugs. Recent Pat Anticancer Drug Discov 1:121-127.
55. Momeni N, Nordstrom B M, Horstmann V, Avarseji H, Sivberg B V (2005) Alterations of prolyl endopeptidase activity in the plasma of children with autistic spectrum disorders. Bio Med Central Psychiatry 5:27.
56. Myohanen T T, Garcia-Horsman J A, Tenorio-Larang J, and Mannisto P T (2009) Issues about the Physiological Functions of Prolyl Oligopeptidase Based on Its Discordant Spatial Association with Substrates and Inconsistencies Among mRNA, Protein Levels, and Enzymatic Activity. J. Histochem and Cytochem 57(9):831-848.
57. Maes M, Goossnes F, Scharpe S, Calabrese J, Desnyder R, and Meltzer H Y (1995) Alterations in plasma prolyl endopeptidase activity in depression, mania, and schizophrenia: effects of antidepressants, mood stabilizers, and antipsychotic drugs. Psychiatry Res. 58:217-225.
58. Mannisto P T, Venalainen J, Jalkanen A, and Garcia-Horsman J A (2007) Prolyl oligopeptidaes: a potential target for the treatment of cognitive disorders. Drug News Perspect (Abstract) 20(5).

---

What is claimed is:

1. A method of reducing or inhibiting activity of prolyl oligopeptidase (POP) in at least one cell or tissue which expresses POP, comprising:
   administering to the POP-expressing cell or tissue a compound having the formula:

B-$Xaa_{1a}$-Sp-$Xaa_{2a}$-Cyc     (Formula II), wherein:
   B is a blocking group selected from the group consisting of aminobenzoyl (Abz), acetyl (Ac), benzoyl (Bz), benzyloxycarbonyl (Z), t-Butyloxycarbonyl (Boc), Furylacryloyl (Fa), Methoxysuccinyl (MeO-Suc), Pyroglutamate (Pyr), Pyrazine, Phenylalanine, a peptide consisting of 1-3 natural amino acids, and Succinyl (Suc);
   $Xaa_{1a}$ is (a) a positively-charged amino acid, (b) a negatively-charged amino acid, or (c) a positively-charged or negatively-charged amino acid modified to comprise (1) a methylene group in substitution for the carbonyl group adjacent Sp, or (2) an isostere bond between $Xaa_{1a}$ and Sp;
   Sp is a spacer molecule having a length in a range of from 0.3 nm to 2.5 nm;
   $Xaa_{2a}$ is a positively-charged amino acid; and
   Cyc is a boronyl proline, proline carbonitrile, nitrile pyrrolidone, or cyanopyrrolidine.

2. The method of claim 1, wherein in the compound, $Xaa_{1a}$ is selected from the group consisting of α,β-diaminopropionic acid; α,γ-diaminobutyric acid; ornithine; β-homoornithine; arginine; β-homoarginine; homoarginine; lysine; homolysine; β-homolysine; histidine; aspartic acid; and glutamic acid.

3. The method of claim 1, wherein in the compound, $Xaa_{1a}$ is selected from the group consisting of aspartic acid and glutamic acid.

4. The method of claim 1, wherein in the compound, $Xaa_{2a}$ is selected from the group consisting of α,β-diaminopropionic acid; α,γ-diaminobutyric acid; ornithine; β-homoornithine; arginine; β-homoarginine; homoarginine; lysine; homolysine; β-homolysine; and histidine.

5. The method of claim 1, wherein in the compound, Sp is selected from the group consisting of γ-aminobutyric acid; ε-aminocaproic acid; 8-amino-3,6-dioxaoctanoic acid; 11-amino-3,6,9-trioxaundecanoic acid; 14-amino-3,6,9,12-tetraoxatetradecanoic acid; α-aminobutyric acid; 5-aminopentanoic acid; 6-aminohexanoic acid; 7-aminoheptanoic acid; 8-aminooctanoic acid; 3-(aminooxy)acetic acid; β-alanine; glycine; alanine; threonine; tryptophan; tyrosine; methionine; leucine; isoleucine; valine; serine; proline; ethylene glycol; PEG$_n$ (wherein n=1-6); propylene glycol; PPG$_n$ (wherein n=1-6); amino-PEG$_n$-carboxy group (wherein n=1-6); amino-PPG$_n$-carboxy (wherein n=1-6); and combinations thereof.

6. The method of claim 1, wherein in the compound, Sp is leucine, isoleucine, valine, or alanine.

7. The method of claim 1, wherein in the compound, Sp has a length in a range of from 0.6 nm to 1.75 nm.

8. The method of claim 1, wherein in the compound, B is an acetyl, pyroglutamate, or succinyl; Xaa$_{1a}$ is lysine; Sp is at least one of leucine, isoleucine, valine, or alanine; Xaa$_{2a}$ is arginine; and Cyc is a boronyl proline or cyanopyrrolidine.

9. The method of claim 1, wherein the compound further comprises a single amino acid or a peptide of 2 to 10 amino acids which extends from Cyc in the C-terminal direction.

10. The method of claim 1, wherein the at least one POP-expressing cell or tissue is a cancer cell and/or an activated fibroblast cell.

11. A method of reducing or inhibiting activity of prolyl oligopeptidase (POP) in a subject suffering from a disorder for which the reduction or inhibition of POP provides a therapeutically-effective benefit, comprising:
administering to a subject in need of such therapy a compound having the formula:

B-Xaa$_{1a}$-Sp-Xaa$_{2a}$-Cyc    (Formula II), wherein:
B is a blocking group selected from the group consisting of aminobenzoyl (Abz), acetyl (Ac), benzoyl (Bz), benzyloxycarbonyl (Z), t-Butyloxycarbonyl (Boc), Furylacryloyl (Fa), Methoxysuccinyl (MeO-Suc), Pyroglutamate (Pyr), Pyrazine, Phenylalanine, a peptide consisting of 1-3 natural amino acids, and Succinyl (Suc);
Xaa$_{1a}$ is (a) a positively-charged amino acid, (b) a negatively-charged amino acid, or (c) a positively-charged or negatively-charged amino acid modified to comprise (1) a methylene group in substitution for the carbonyl group adjacent Sp, or (2) an isostere bond between Xaa$_{1a}$ and Sp;
Sp is a spacer molecule having a length in a range of from 0.3 nm to 2.5 nm;
Xaa$_{2a}$ is a positively-charged amino acid; and
Cyc is a boronyl proline, proline carbonitrile, nitrile pyrrolidone, or cyanopyrrolidine.

12. The method of claim 11, wherein the disorder for which the reduction or inhibition of POP provides a therapeutically-effective benefit is at least one of angiogenesis and cancer.

13. The method of claim 11, wherein in the compound, Xaa$_{1a}$ is selected from the group consisting of α,β-diaminopropionic acid; α,γ-diaminobutyric acid; ornithine; β-homoornithine; arginine; β-homoarginine; homoarginine; lysine; homolysine; β-homolysine; histidine; aspartic acid; and glutamic acid.

14. The method of claim 11, wherein in the compound, Xaa$_{1a}$ is selected from the group consisting of aspartic acid and glutamic acid.

15. The method of claim 11, wherein in the compound, Xaa$_{2a}$ is selected from the group consisting of α,β-diaminopropionic acid; α,γ-diaminobutyric acid; ornithine; β-homoornithine; arginine; β-homoarginine; homoarginine; lysine; homolysine; β-homolysine; and histidine.

16. The method of claim 11, wherein in the compound, Sp is selected from the group consisting of γ-aminobutyric acid; ε-aminocaproic acid; 8-amino-3,6-dioxaoctanoic acid; 11-amino-3,6,9-trioxaundecanoic acid; 14-amino-3,6,9,12-tetraoxatetradecanoic acid; α-aminobutyric acid; 5-aminopentanoic acid; 6-aminohexanoic acid; 7-aminoheptanoic acid; 8-aminooctanoic acid; 3-(aminooxy)acetic acid; β-alanine; glycine; alanine; threonine; tryptophan; tyrosine; methionine; leucine; isoleucine; valine; serine; proline; ethylene glycol; PEG$_n$ (wherein n=1-6); propylene glycol; PPG$_n$ (wherein n=1-6); amino-PEG$_n$-carboxy group (wherein n=1-6); amino-PPG$_n$-carboxy (wherein n=1-6); and combinations thereof.

17. The method of claim 11, wherein in the compound, Sp is leucine, isoleucine, valine, or alanine.

18. The method of claim 11, wherein in the compound, Sp has a length in a range of from 0.6 nm to 1.75 nm.

19. The method of claim 11, wherein in the compound, B is an acetyl, pyroglutamate, or succinyl; Xaa$_{1a}$ is lysine; Sp is at least one of leucine, isoleucine, valine, or alanine; Xaa$_{2a}$ is arginine; and Cyc is a boronyl proline or cyanopyrrolidine.

20. The method of claim 11, wherein the compound further comprises a single amino acid or a peptide of 2 to 10 amino acids which extends from Cyc in the C-terminal direction.

* * * * *

UNITED STATES PATENT AND TRADEMARK OFFICE
CERTIFICATE OF CORRECTION

PATENT NO. : 10,155,789 B2
APPLICATION NO. : 15/602709
DATED : December 18, 2018
INVENTOR(S) : Patrick A. McKee et al.

It is certified that error appears in the above-identified patent and that said Letters Patent is hereby corrected as shown below:

In the Specification
Column 10, Line 34: Delete "Glade" and replace with -- clade --
Column 26, Line 5: After "spongiosum," delete "squarrous" and replace with -- squarnous --
Column 31, Line 65-66: Delete "lobenguane" and replace with -- Iobenguane --
Column 31, Line 66: Delete "lodoantipyrine" and replace with -- Iodoantipyrine --
Column 31, Line 67: Delete "lodocholesterol" and replace with -- Iodocholesterol --
Column 31, Line 67: Delete "lodohippurate" and replace with -- Iodohippurate --
Column 31, Line 67 – Column 32, Line 1: Delete "lodohippurate" and replace with -- Iodohippurate --
Column 32, Line 1: Delete "lodohippurate Sodium I 131," and replace with -- Iodohippurate Sodium I 131, --
Column 32, Line 2: Delete "lofetamine" and replace with -- Iofetamine --
Column 32, Line 3: Delete "lomethin I 125, lomethinI 131," and replace with -- Iomethin I 125, Iomethin I 131, --
Column 32, Line 4: Delete "lotyrosine" and replace with -- Iotyrosine --
Column 45, Line 30: Delete "lsotyping" and replace with -- Isotyping --
Column 48, Line 1: Delete "Glade" and replace with -- clade --
Column 61, Line 61: Delete "Old U," and replace with -- Old L J, --
Column 61, Line 67: Delete "Old U," and replace with -- Old L J, --
Column 62, Line 20: Delete "Old U" and replace with -- Old L J --
Column 62, Line 56: Delete "Old U" and replace with -- Old L J --
Column 63, Line 6: Delete "ltoi E," and replace with -- Itoi E, --
Column 63, Line 15: Delete "lwasa" and replace with -- Iwasa --
Column 63, Line 31: Delete "Old U," and replace with -- Old L J, --
Column 64, Line 42: Delete "Old U," and replace with -- Old L J, --
Column 64, Line 48: Delete "lrazusta" and replace with -- Irazusta --

Signed and Sealed this
Nineteenth Day of March, 2019

Andrei Iancu
*Director of the United States Patent and Trademark Office*